United States Patent
Gant et al.

(10) Patent No.: US 7,598,273 B2
(45) Date of Patent: Oct. 6, 2009

(54) INHIBITORS OF THE GASTRIC H+, K+-ATPASE WITH ENHANCED THERAPEUTIC PROPERTIES

(75) Inventors: Thomas G. Gant, Carlsbad, CA (US); Sepehr Sarshar, Cardiff by the Sea, CA (US)

(73) Assignee: Auspex Pharmaceuticals, Inc, Vista, CA (US)

( * ) Notice: Subject to any disclaimer, the term of this patent is extended or adjusted under 35 U.S.C. 154(b) by 346 days.

(21) Appl. No.: 11/544,407

(22) Filed: Oct. 4, 2006

(65) Prior Publication Data

US 2007/0082929 A1 Apr. 12, 2007

Related U.S. Application Data

(60) Provisional application No. 60/724,160, filed on Oct. 6, 2005, provisional application No. 60/741,316, filed on Dec. 1, 2005.

(51) Int. Cl.
*A61K 31/4439* (2006.01)
*C07D 401/12* (2006.01)
(52) U.S. Cl. .................... 514/338; 546/273.7
(58) Field of Classification Search .............. 546/273.7; 514/338
See application file for complete search history.

(56) References Cited

U.S. PATENT DOCUMENTS

| | | | |
|---|---|---|---|
| 4,628,098 A | 12/1986 | Nohara | |
| 4,758,579 A | 7/1988 | Kohl | |
| 5,013,743 A | 5/1991 | Iwahi | |
| 5,026,560 A | 6/1991 | Makino | |
| 5,045,321 A | 9/1991 | Makino | |
| 5,093,132 A | 3/1992 | Makino | |
| 5,433,959 A | 7/1995 | Makino | |
| 5,464,632 A | 11/1995 | Cousin et al. | |
| 5,690,960 A | 11/1997 | Bengtsson et al. | |
| 5,714,504 A | 2/1998 | Lindberg et al. | |
| 5,840,737 A | 11/1998 | Phillips | |
| 5,877,192 A | 3/1999 | Lindberg | |
| 5,900,424 A | 5/1999 | Kallstrum et al. | |
| 5,997,903 A | 12/1999 | Dietrich | |
| 6,123,962 A | 9/2000 | Makino | |
| 6,143,771 A | 11/2000 | Lindberg | |
| 6,147,103 A | 11/2000 | Anousis et al. | |
| 6,150,380 A | 11/2000 | Lovqvist et al. | |
| 6,166,213 A | 12/2000 | Anousis et al. | |
| 6,191,148 B1 | 2/2001 | Anousis et al. | |
| 6,328,994 B1 | 12/2001 | Shimizu | |
| 6,369,085 B1 | 4/2002 | Cotton et al. | |
| 6,428,810 B1 | 8/2002 | Bergstrand et al. | |
| 6,462,058 B1 | 10/2002 | Fujishima et al. | |
| 6,489,346 B1 | 12/2002 | Phillips | |
| 6,645,988 B2 | 11/2003 | Phillips | |
| 6,664,276 B2 | 12/2003 | Fujishima et al. | |
| 6,699,885 B2 | 3/2004 | Phillips | |
| 6,749,864 B2 | 6/2004 | Makino | |
| 6,780,881 B2 | 8/2004 | Linder | |
| 6,780,882 B2 | 8/2004 | Phillips | |
| 6,818,200 B2 | 11/2004 | Foster | |
| 6,875,872 B1 | 4/2005 | Lindberg et al. | |
| 6,939,971 B2 | 9/2005 | Fujishima et al. | |
| 7,285,668 B2 | 10/2007 | Hashimoto et al. | |
| 7,351,723 B2 | 4/2008 | Linder et al. | |
| 7,396,841 B2 | 7/2008 | Doen et al. | |
| 7,399,485 B1 | 7/2008 | Shimizu et al. | |
| 7,399,772 B2 | 7/2008 | Phillips | |
| 7,411,070 B2 | 8/2008 | Cotton et al. | |
| 7,431,942 B2 | 10/2008 | Shimizu et al. | |
| 2002/0013372 A1 | 1/2002 | Ekins | |
| 2002/0094995 A1 | 7/2002 | Foster | |
| 2004/0253180 A1 | 12/2004 | Foster et al. | |
| 2007/0082929 A1 | 4/2007 | Gant et al. | |
| 2007/0281894 A1 | 12/2007 | Gant et al. | |
| 2008/0033011 A1 | 2/2008 | Tung | |
| 2008/0146610 A1 | 6/2008 | Kohl et al. | |
| 2008/0255200 A1 | 10/2008 | Gant et al. | |
| 2008/0261983 A1 | 10/2008 | Persichetti et al. | |

FOREIGN PATENT DOCUMENTS

| | | |
|---|---|---|
| EP | 0005129 A1 | 10/1979 |
| WO | WO 9526325 | 10/1995 |
| WO | WO-2007-012650 A1 | 2/2007 |
| WO | WO-2007-012651 A1 | 2/2007 |
| WO | WO 2007023135 A1 | 3/2007 |
| WO | WO 2007039464 A1 | 4/2007 |
| WO | WO 2007041630 A1 | 4/2007 |
| WO | WO 2007143507 A2 | 12/2007 |
| WO | WO 2008035195 A1 | 3/2008 |
| WO | WO 2008114123 A1 | 9/2008 |
| WO | WO 2008127640 A2 | 10/2008 |
| WO | WO 2008130863 A2 | 10/2008 |
| WO | WO 2008131259 A1 | 10/2008 |

(Continued)

OTHER PUBLICATIONS

Balant et al., "Metabolic Consdierations, etc.," Burger's Medicinal Chemistry, 5 ed, 1, Wollf ed. NY: John Wiley & Sons, 1995, 949-982.*

(Continued)

*Primary Examiner*—Patricia L Morris
(74) *Attorney, Agent, or Firm*—Dennis A. Bennett; Michael Sertic

(57) ABSTRACT

Chemical syntheses and medical uses of novel inhibitors of the gastric H+, K+-ATPase for the treatment and/or management of duodenal ulcers, heartburn, acid reflux, other conditions mediated by gastric acid secretion and/or psoriasis are described.

Formula 1

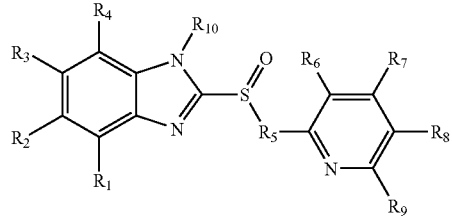

12 Claims, No Drawings

OTHER PUBLICATIONS

Vippagunta et al., "Crystalline Solid", Advanced Drug Delivery Reviews 48 (2001) 3-26.*

Guillory (in Brittain ed.), "Polymorphism, etc.," NY: Marcel Dekker, Inc., 1999, 1-2, 183-226.*

Tonini et al., "Novel therapeutic strategies in acid-related disorders," Exp. Op. Ther. Patents 13(5):639-649 (2003).

Crowe, A. M.; The Preparation of Carbon-14-, Sulfur-35-, and Carbon-13-Labeled Forms of Omeprazole. Journal of Labelled Compounds and Radiopharmaceuticals (1986), 23(1), 21-33; Smith Kline and French Res. Ltd., The Frythe/Welwyn/Hertfordshire, UK.

Kushner, D. J et al.; Pharmacological Uses and Perspectives of Heavy Water and Deuterated Compounds, Canadian Journal of Physiology and Pharmacology (1999), 77(2), 79-88; Department of Botany, University of Toronto, Toronto, ON, Can.

Gant, Thomas G. et al; Substituted Benzimidazoles; not yet published; U.S. Appl. No. 11/818,970, filed Apr. 11, 2007.

Gant, Thomas G. et al; Substituted Benzimidazoles; not yet published; U.S. Appl. No. 12/082,470, filed Apr. 11, 2008.

Wang, Haiyong et al.; Preparation of 8-Deuterium-substituted Omeprazole Sodium in situ; Institute of Radiation Medicine, Academy of Military Medical Sciences, Beijing 10085.

TLC PharmaChem; Omeprazole-d3; CAS No. 73590-58-6; TLC ID/catalog No: O-021; website: http://www.tlcpharmachem.com/tlc/tlc_item.php?upc=O-021&li=le_21&sub=A.

Bauer, LA; et al.; Influence of long-term infusions on lidocaine kinetics; Clin. Pharmacol. Ther. 31(4), 433-437 (1982).

Drug Report for Omeprazole, Thomson Investigational Drug Database; downloaded Jan. 25, 2009.

Borgstrom, L et al; Comparative Pharmacokinetics of Unlabeled and Deuterium-Labeled Terbutaline: Demonstration of a Small Isotope Effect; J Pharm Sci, 77(11) 952-4 (1988).

Browne, TR; Chapter 2. Isotope Effect: Implications for pharmaceutical investigations; Stable isotopes in pharmaceutical research; Elsevier; Amsterdam, 1997.

Browne, TR et al.; Pharmacokinetic equivalence of stable-isotope-labeled and unlabeled drugs. Phenobarbital in man; J Clin Pharmacol, 22, 309-15 (1982).

Burn, AGL et al.; Pharmacokinetics of Lidocaine and Bupivacaine and stbel isotope labelled analogues: a study in healthy volunteers; Biopharma & Drug Disp, 9 85-95 (1988).

Elison, C. et al.; Effect of deuteration of N-CH3 Group on Potency and enzymatic N-demethylation of morphine; Science, 134(3485) 1078-9 (1961).

Farmer, PB et al.; Synthesis, metabolism, and antitumor activity of deuterated analogues of 1-(2-chloroethyl)-3-cyclohexyl-1-nitrosourea; J Med Chem, 21(6) 514-520 (1978).

Fisher, MB et al.; The complexities inherent in attempts to decrease drug clearance by blocking sites of CYP-mediated metabolism; Curr Opin in Drug Disc & Develop 9(1) 101-109 (2006).

Foster, AB; Deuterium isotope effects in studies of drug metabolism; Trends in Pharma Sci, 524-527 (1984).

Helfenbein, J et al; Isotopic Effect Study of Propofol Deuteration on the Metabolism, Activity, and Toxicity of the Anesthetic; J Med Chem, 45, 5806-5808 (2002).

Lee, H. et al; Deuterium magic angle spinning studies of substrates bound to cytochrome P450; Biochem. 38 10808-13 (1999).

Mamada, K. et al.; Pharmacokinetic equivalence of deuterium-labeled and unlabeled phenytoin; Drug Metab Disp. 14 (4) 509-11 (1986).

Nelson, SD. et al.; The use of deuterium isotope effects to probe the active site properties, mechanism, of cytochrome P450-catalyzed reactions, and mechanisms of metabolically dependent toxicity; Drug Metab Disp. 31(12) 1481-98 (2003).

Nelson, SD et al.; Primary and B-Secondary Deuterium Isotope Effects in N-Deethylation reactions; J Med Chem. 18(11) 1062-1065 (1975).

Pohl, LR et al.; Determination of Toxic Pathways of Metabolism by Deuterium Substitution; Drug Metab Rev. 15(7) 1335-51 (1984-5).

Rampe, D. et al.; Deuterated analogs of Verapamil and Nifedipine. Synthesis and biological activity; Eur J Med Chem. 28 259-263 (1993).

Medical Isotopes, Inc.; Lansoprazole-d4, catalog No. D11327 website: http://www.medicalisotopes.com/Product_Details.asp?find=26952.

TLC PharmaChem; Pantoprazole-d3; CAS No. 102625-70-7 TLC ID# (catalog No.): P-013 website: http://www.tlcpharmachem.com/tlc/tlc_item.php?upc=P-013&li=le_21&sub=P.

* cited by examiner

INHIBITORS OF THE GASTRIC H+, K+-ATPASE WITH ENHANCED THERAPEUTIC PROPERTIES

CROSS-REFERENCE TO RELATED APPLICATIONS

This application claims priority to U.S. Provisional Application Nos. 60/724,160, entitled "INHIBITORS OF THE GASTRIC H+, K+-ATPASE WITH ENHANCED THERAPEUTIC PROPERTIES", filed Oct. 6, 2005; and 60/741,316, entitled "INHIBITORS OF THE GASTRIC H+, K+-ATPASE WITH ENHANCED THERAPEUTIC PROPERTIES, filed Dec. 1, 2005, both of which are incorporated by reference in their entireties.

BACKGROUND OF THE INVENTION

1. Field of the Invention

The present invention is directed to inhibitors of the gastric H+, K+-ATPase and pharmaceutically acceptable salts and prodrugs thereof, the chemical synthesis thereof, and the medical use of such compounds for the treatment and/or management of duodenal ulcers, heartburn, acid reflux, other conditions mediated by gastric acid secretion and/or psoriasis.

2. Description of the Related Art

In an attempt to breakdown or to help solubilize chemicals and nutrients that have been absorbed into the blood, the human body expresses various enzymes (e.g. the cytochrome $P_{450}$ enzymes or CYPs, esterases, proteases, reductases, dehydrogenases, and the like) that react with the chemicals and nutrients to produce novel intermediates or metabolites. Some of the most common metabolic reactions of pharmaceutical compounds involve the oxidation of a carbon-hydrogen (C—H) bond to either a carbon-oxygen (C—O) or carbon-carbon (C—C) π-bond. The resultant metabolites may be stable or unstable under physiological conditions, and can have substantially different pharmacokinetic, pharmacodynamic, acute and long-term toxicity profiles relative to the parent compounds. For most drugs, such oxidations are generally rapid and ultimately lead to administration of multiple or high daily doses. There is therefore an obvious and immediate need for improvements of such drugs.

Chemical kinetics is the study of reaction rates. The activation energy $E_{act}$ in chemistry is the energy that must be supplied to a system in order to initiate a particular chemical process. In other words, this is the minimum energy required for a specific chemical reaction to take place. A reaction will occur between two properly oriented molecules if they possess a minimum requisite energy. During the approach, the outer shell electrons of each molecule will induce repulsion. Overcoming this repulsion requires an input of energy (i.e. the activation energy), which results from the heat of the system; i.e. the translational, vibrational, and rotational energy of each molecule. If sufficient energy is available, the molecules may attain the proximity and orientation necessary to cause a rearrangement of bonds to form new substances.

The relationship between the activation energy and the rate of reaction may be quantified by the Arrhenius equation which states that the fraction of molecules that have enough energy to overcome an energy barrier—those with energy at least equal to the activation energy, $E_{act}$—depends exponentially on the ratio of the activation to thermal energy $k=Ae^{-E_{act}/RT}$. In this equation, RT is the average amount of thermal energy that molecules possess at a certain temperature T, where R is the molar gas constant, k is the rate constant for the reaction and A (the frequency factor) is a constant specific to each reaction that depends on the probability that the molecules will collide with the correct orientation.

The transition state in a reaction is a short lived state (on the order of $10^{-14}$ sec) along the reaction pathway during which the original bonds have stretched to their limit. By definition, the activation energy $E_{act}$ for a reaction is the energy required to reach the transition state of that reaction. Reactions that involve multiple steps will necessarily have a number of transition states, and in these instances, the activation energy for the reaction is equal to the energy difference between the reactants and the most unstable transition state. Once the transition state is reached, the molecules can either revert, thus reforming the original reactants, or the new bonds form giving rise to the products. This dichotomy is possible because both pathways, forward and reverse, result in the release of energy. A catalyst facilitates a reaction process by lowering the activation energy leading to a transition state. Enzymes are examples of biological catalysts that reduce the energy necessary to achieve a particular transition state.

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) is two-fold more massive than hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e. the step with the highest transition state energy), then substituting a deuterium for that hydrogen will cause a decrease in the reaction rate and the process will slow down. This phenomenon is known as the deuterium Kinetic Isotope Effect (DKIE) and can range from 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small size of a hydrogen atom, and occurs because transition states involving a proton can sometimes form in the absence of the required activation energy. A deuterium is larger and statistically has a much lower probability of undergoing this phenomenon. Substitution of tritium for hydrogen results in yet a stronger bond than deuterium and gives numerically larger isotope effects.

Discovered in 1932 by Urey, deuterium (D) is a stable and non-radioactive isotope of hydrogen. It was the first isotope to be separated from its element in pure form and is twice as massive as hydrogen, and makes up about 0.02% of the total mass of hydrogen (in this usage meaning all isotopes) on earth. When two deuteriums bond with one oxygen, deuterium oxide ($D_2O$ or "heavy water") is formed. $D_2O$ looks and tastes like $H_2O$ but it has different physical properties. It boils at 101.41° C. and freezes at 3.79° C. Its heat capacity, heat of fusion, heat of vaporization, and entropy are all higher than $H_2O$. It is also more viscous and is not as powerful a solvent as $H_2O$.

Tritium (T) is a radioactive isotope of hydrogen, used in research, fusion reactors, neutron generators and radiopharmaceuticals. Mixing tritium with a phosphor provides a continuous light source, a technique that is commonly used in wristwatches, compasses, rifle sights and exit signs. It was discovered by Rutherford, Oliphant and Harteck in 1934 and is produced naturally in the upper atmosphere when cosmic rays react with $H_2$ molecules. Tritium is a hydrogen atom that has 2 neutrons in the nucleus and has an atomic weight close to 3. It occurs naturally in the environment in very low concentrations, most commonly found as $T_2O$, a colorless and odorless liquid. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk.

When pure $D_2O$ is given to rodents, it is readily absorbed and reaches an equilibrium level that is usually about eighty percent of the concentration that is consumed by the animals. The quantity of deuterium required to induce toxicity is extremely high. When 0 to as much as 15% of the body water has been replaced by $D_2O$, animals are healthy but are unable to gain weight as fast as the control (untreated) group. Between 15 to 20% $D_2O$, the animals become excitable. At 20 to 25%, the animals are so excitable that they go into frequent convulsions when stimulated. Skin lesions, ulcers on the paws and muzzles, and necrosis of the tails appear. The animals also become very aggressive; males becoming almost unmanageable. At 30%, the animals refuse to eat and become comatose. Their body weight drops sharply and their metabolic rates drop far below normal, with death occurring at 30 to 35% replacement. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles, has been demonstrated previously with some classes of drugs. For example, DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching which may even give rise to an oxidative intermediate with a faster off-rate from an activating Phase I enzyme (e.g. cytochrome $P_{450}$ 3A4). The concept of metabolic switching asserts that xenogens, when sequestered by Phase I enzymes, may bind transiently and re-bind in a variety of conformations prior to the chemical reaction (e.g. oxidation). This claim is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity. Such pitfalls are non-obvious and have not been heretofore sufficiently predictable a priori for any drug class.

Omeprazole (PRILOSEC®) is an inhibitor of the gastric $H^+$, $K^+$-ATPase. This class of drugs includes, among others, esomeprazole, lansoprazole, pantoprazole, rabeprazole, leminoprazole, ilaprazole, nepaprazole, saviprazole and tenatoprazole. The mechanism of action of these drugs has been extensively studied, and it is postulated that they react transiently with a critical cysteine in the gastric $H^+$, $K^+$-ATPase ("gastric $H^+$ pump"). Omeprazole has been shown to degrade to inactive and less active metabolites as part of its metabolic clearance from systemic circulation. This degradation is so rapid that the producer of omeprazole (AstraZeneca) undertook a full development/clinical program to develop and market its successor (i.e. esomeprazole (NEXIUM®)), a homochiral analog of omeprazole with a very similar pharmacodynamic, pharmacokinetic and toxicological profile. The only noticeable difference resides in the fact that the half-life of esomeprazole in human plasma is 20% higher than that of omeprazole. Clinical advantages of esomeprazole versus omeprazole are unclear. "[AstraZeneca's] conclusion that [esomeprazole] has been shown to provide a significant clinical advantage over omeprazole in the first-line treatment of patients with acid-related disorders is not supported by data." (Center for Drug Evaluation and Research, application number 21-153/21-154 for Esomeprazole Magnesium (Nexium), MEDICAL OFFICER'S REVIEW, Section X, Summary of Benefits vs Risks). The benefits of extending the half-lives of this class have been supported in theory by all researchers in this field but clearly a 20% improvement is not sufficient to affect a clinical advantage. An approach with far greater potential to improve clinical response is needed.

Human clinical studies have also shown that

Esomeprazole is extensively metabolized in the liver by the cytochrome $P_{450}$ (CYP) enzyme system. The metabolites of esomeprazole lack antisecretory activity. The major part of esomeprazole's metabolism is dependent upon the CYP2C19 isoenzyme which forms the hydroxy- and desmethyl metabolites. The remaining amount is dependent on CYP3A4 which forms the sulphone metabolite. CYP2C19 isoenzyme exhibits polymorphism in the metabolism of esomeprazole, since some 3% of Caucasians and 15-20% of Asians lack CYP2C19 and are termed poor metabolizers. At steady state, the ratio of Area Under the Curve (AUC) in Poor metabolizers to AUC in the rest of the population (i.e. extensive metabolizers) is approximately 2.

(Center for Drug Evaluation and Research, application number 21-153/21-154, Final Printed Labeling for Esomeprazole Magnesium (Nexium), FDA Approval Labeling Feb. 14, 2001).

There is therefore an immediate need for improvements in the development of gastric $H^+$, $K^+$-ATPase modulators.

SUMMARY OF THE INVENTION

Disclosed herein are compounds of Formula 1:

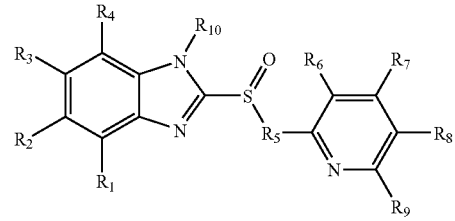

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt, solvate, or prodrug thereof wherein:

$R_1$, $R_4$, $R_9$ and $R_{10}$ are independently selected from the group consisting of hydrogen, and deuterium;

$R_2$, $R_3$, $R_6$, and $R_8$ are independently selected from the group consisting of hydrogen, deuterium, $C_1$-$C_6$ alkyl, and $C_1$-$C_6$ alkyloxy;

$R_5$ is selected from the group consisting of —$CH_2$—, —CHD— and —$CD_2$—;

$R_7$ is selected from the group consisting of hydrogen, deuterium, —$NO_2$, $C_1$-$C_6$ alkyl, and $C_1$-$C_6$ alkyloxy;

provided that compounds of Formula 1 contain at least one deuterium atom, and provided that deuterium enrichment in compounds of Formula 1 is at least about 1%.

Also disclosed herein are pharmaceutical compositions comprising a compound according to Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, with a pharmaceutically acceptable carrier.

Further, disclosed herein are methods of eliciting, modulating and/or regulating the gastric $H^+$, $K^+$-ATPase.

In addition, disclosed herein are methods of treating and/or managing a mammalian subject having, suspected of having, or being prone to a disease or condition involving duodenal ulcers, other conditions mediated by gastric acid secretion and/or psoriasis.

DETAILED DESCRIPTION OF THE INVENTION

Certain gastric $H^+$, $K^+$-ATPase modulators are known in the art. The structures of some of the known modulators are

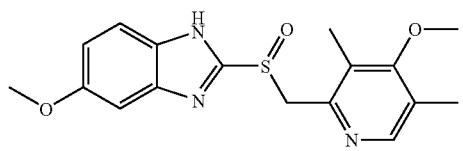

Omeprazole ("Prilosec")

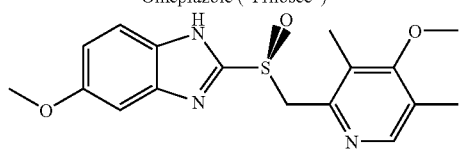

Esomeprazole ("Nexium")

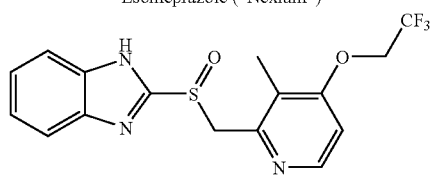

Lansoprazole ("Takepron")

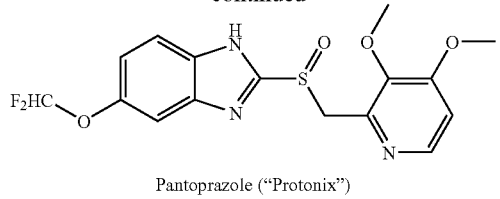

Pantoprazole ("Protonix")

The carbon-hydrogen bonds of these gastric $H^+$, $K^+$-ATPase modulators contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation produce a detectable Kinetic Isotope Effect (KIE) that could affect the pharmacokinetic, pharmacologic and/or toxicologic parameters of these gastric $H^+$, $K^+$-ATPase modulators relative to compounds having naturally occurring levels of deuterium. Aspects of the present invention disclosed herein describe a novel approach to designing and synthesizing new analogs of these gastric $H^+$, $K^+$-ATPase modulators through chemical modifications and derivations of the carbon-hydrogen bonds of the modulators and/or of the chemical precursors used to synthesize said modulators. Suitable modifications of certain carbon-hydrogen bonds into carbon-deuterium bonds may generate novel gastric $H^+$, $K^+$-ATPase modulators with unexpected and non-obvious improvements of pharmacological, pharmacokinetic and toxicological properties in comparison to the non-isotopically enriched gastric $H^+$, $K^+$-ATPase modulators. This invention relies on the judicious and successful application of chemical kinetics to drug design. Deuterium incorporation levels in the compounds of the invention are significantly higher than the naturally-occurring levels and are sufficient to induce at least one substantial improvement as described herein.

Information has come to light that enables the judicious use of deuterium in solving the PK and PD shortcomings for gastric $H^+$, $K^+$-ATPase modulators. For example, the (S)-isomer of omeprazole is rapidly oxidized at the benzimidazole methoxy group to a metabolite with little or no antisecretory activity. The (R)-isomer of omeprazole is rapidly oxidized to the 5-hydroxymethyl-pyridyl metabolite that also has little or no antisecretory activity. The toxicity of these metabolites is unknown. Furthermore, because these oxidations take place via polymorphically expressed CYP2C19, and because an inhibition of CYP2C19 ensues, the prevention of such oxidative destruction decreases interpatient variability, decreases drug-drug interactions, increases $T_{1/2}$, decreases the necessary $C_{max}$, and improves several other Absorption, Distribution, Metabolism, Excretion, and toxicological (ADMET) parameters. This affords many reasonable strategies: deuteration to protect sites in the (S)-isomer, deuteration to protect sites in the (R)-isomer, or deuteration to protect sites in each as applied to the racemic material. Furthermore, sites other than those mentioned above are deuterated when metabolic switching dictates that this is necessary. All of the other compounds of this invention have similar considerations with regard to the DKIE application.

The deuterated analogs of this invention have the potential to uniquely maintain the beneficial aspects of the non-isotopically enriched drugs while substantially increasing the half-life ($T_{1/2}$), lowering the maximum plasma concentration ($C_{max}$) of the minimum efficacious dose (MED), lowering the efficacious dose and thus decreasing the non-mechanismrelated toxicity, and/or lowering the probability of drug-drug interactions. These drugs also have strong potential to reduce the cost-of-goods (COG) owing to the ready availability of inexpensive sources of deuterated reagents combined with previously mentioned potential for lowering the therapeutic dose.

Thus, in one aspect, there are provided herein compounds having the structural Formula 1:

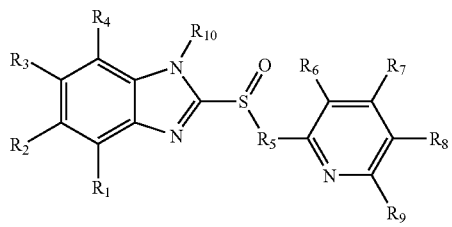

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt, solvate, or prodrug thereof, wherein:

$R_1$, $R_4$, $R_9$ and $R_{10}$ are independently selected from the group consisting of hydrogen, and deuterium;

$R_2$, $R_3$, $R_6$, and $R_8$ are independently selected from the group consisting of hydrogen, deuterium, $C_1$-$C_6$ alkyl, and $C_1$-$C_6$ alkyloxy;

$R_5$ is selected from the group consisting of —$CH_2$—, —CHD— and —$CD_2$—;

$R_7$ is selected from the group consisting of hydrogen, deuterium, —$NO_2$, $C_1$-$C_6$ alkyl, $C_1$-$C_6$ alkyloxy, and $C_1$-$C_6$ alkoxy($C_1$-$C_6$)alkyloxy;

provided that compounds of Formula 1 contain at least one deuterium atom, and provided that deuterium enrichment in compounds of Formula 1 is at least about 1%.

Compounds of this invention have the potential to uniquely maintain the beneficial aspects of non-isotopically enriched gastric $H^+$, $K^+$-ATPase modulators while substantially altering the half-life ($T_{1/2}$), lowering the maximum plasma concentration ($C_{max}$) of the minimum efficacious dose (MED), lowering the efficacious dose and thus decreasing non-mechanism-related toxicities, and/or lowering the probability of drug-drug interactions. These drugs also have potential to reduce the cost-of-goods (COG) due to a potential for lowering the therapeutic dose when compared to the non-isotopically enriched gastric $H^+$, $K^+$-ATPase modulators. In sum, many aspects of ADMET of the non-isotopically enriched gastric $H^+$, $K^+$-ATPase modulators are substantially improved by this invention.

Agents in the present invention will expose patients to a maximum of 0.000005% $D_2O$ (can also be expressed as 0.00001% DHO). This quantity is a small fraction of the naturally occurring background levels of $D_2O$ (or DHO) in circulation. Even this minute exposure would require complete metabolism of every drug-incorporated C-D bond, and yet this C-D metabolism is precisely the phenomenon that can be eliminated or diminished through creative incorporation. Recall the levels of $D_2O$ shown to cause toxicity in animals (vide supra). The safety factor is thus extraordinary for this approach.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%. In some embodiments, the deuterium enrichment in the compounds of the present invention is greater than 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

"Isotopic enrichment" refers to the percentage of incorporation of a less prevalent isotope of an element at a given site on the molecule instead of the more prevalent isotope of the element. "Non-isotopically enriched" refers to a molecule in which the percentage of the various isotopes is substantially the same as the naturally occurring percentages.

In certain embodiments, the compound of Formula 1 contains about 60% or more by weight of the (−)-enantiomer of the compound and about 40% or less by weight of (+)-enantiomer of the compound. In some embodiments, the compound of Formula 1 contains about 70% or more by weight of the (−)-enantiomer of the compound and about 30% or less by weight of (+)-enantiomer of the compound. In some embodiments, the compound of Formula 1 contains about 80% or more by weight of the (−)-enantiomer of the compound and about 20% or less by weight of (+)-enantiomer of the compound. In some embodiments, the compound of Formula 1 contains about 90% or more by weight of the (−)-enantiomer of the compound and about 10% or less by weight of the (+)-enantiomer of the compound. In some embodiments, the compound of Formula 1 contains about 95% or more by weight of the (−)-enantiomer of the compound and about 5% or less by weight of (+)-enantiomer of the compound. In some embodiments, the compound of Formula 1 contains about 99% or more by weight of the (−)-enantiomer of the compound and about 1% or less by weight of (+)-enantiomer of the compound.

In certain other embodiments, the compound of Formula 1 contains about 60% or more by weight of the (+)-enantiomer of the compound and about 40% or less by weight of (−)-enantiomer of the compound. In some embodiments, the compound of Formula 1 contains about 70% or more by weight of the (+)-enantiomer of the compound and about 30% or less by weight of (−)-enantiomer of the compound. In some embodiments, the compound of Formula 1 contains about 80% or more by weight of the (+)-enantiomer of the compound and about 20% or less by weight of (−)-enantiomer of the compound. In some embodiments, the compound of Formula 1 contains about 90% or more by weight of the (+)-enantiomer of the compound and about 10% or less by weight of the (−)-enantiomer of the compound. In some embodiments, the compound of Formula 1 contains about 95% or more by weight of the (+)-enantiomer of the compound and about 5% or less by weight of (−)-enantiomer of the compound. In some embodiments, the compound of Formula 1 contains about 99% or more by weight of the (+)-enantiomer of the compound and about 1% or less by weight of (−)-enantiomer of the compound.

In some embodiments, the alkyl is selected from the group consisting of methyl, ethyl, n-propyl, iso-propyl, n-butyl, sec-butyl, iso-butyl, and tert-butyl. In certain embodiments the alkyloxy is selected from the group consisting of methoxy, ethoxy, n-propoxy, iso-propoxy, n-butoxy, sec-butoxy, iso-butoxy, and tert-butoxy.

In certain embodiments, $R_1$ is hydrogen. In other embodiments, $R_2$ is hydrogen. In some embodiments, $R_3$ is hydrogen. In other embodiments, $R_4$ is hydrogen. In still other embodiments, $R_6$ is hydrogen. In yet other embodiments, $R_7$ is hydrogen. In yet other embodiments, $R_8$ is hydrogen. In still other embodiments, $R_9$ is hydrogen. In still other embodiments, $R_{10}$ is hydrogen.

In certain embodiments, $R_1$ is deuterium. In other embodiments, $R_2$ is deuterium. In some embodiments, $R_3$ is deuterium. In other embodiments, $R_4$ is deuterium. In still other embodiments, $R_6$ is deuterium. In yet other embodiments, $R_7$ is deuterium. In yet other embodiments, $R_8$ is deuterium. In still other embodiments, $R_9$ is deuterium. In still other embodiments, $R_{10}$ is deuterium.

In further embodiments, $R_2$ is a $C_{1-6}$ alkyloxy, wherein any one or more of the hydrogen atoms on the alkoxy group can be substituted by deuterium. In some of these embodiments, $R_2$ is selected from the group consisting of —$OCH_3$, —$OCD_3$, —$OCHF_2$, and —$OCDF_2$. In other embodiments, $R_2$ is —$OCD_3$ or —$OCDF_2$.

In other embodiments, $R_5$ is —$CH_2$—, —CHD— or —$CD_2$—;

In yet other embodiments, $R_6$ is a $C_{1-6}$ alkyloxy, wherein any one or more of the hydrogen atoms on the alkoxy group can be substituted by deuterium. In some of these embodiments, $R_6$ is —$OCH_3$, or —$OCD_3$;

In still other embodiments, $R_6$ is a $C_{1-6}$ alkyl, wherein any one or more of the hydrogen atoms on the alkyl group can be substituted by deuterium. In some of these embodiments, $R_6$ is —$CH_3$, or —$CD_3$;

In other embodiments, $R_7$ is a $C_{1-6}$ alkyloxy, wherein any one or more of the hydrogen atoms on the alkoxy group can be substituted by deuterium. In some of these embodiments, $R_7$ is selected from the group consisting of —$OCH_3$, —$OCD_3$, —$OCH_2CF_3$, —$OCD_2CF_3$, and —$O(CH_2)_3OCH_3$ wherein any one or more of the hydrogen atoms in —$O(CH_2)_3OCH_3$ can be substituted by deuterium.

In other embodiments, $R_8$ is a $C_{1-6}$ alkyl wherein any one or more of the hydrogen atoms on the alkyl group can be substituted by deuterium. In some of these embodiments, $R_8$ is —$CH_3$, or —$CD_3$;

In yet other embodiments, $R_8$ is a $C_{1-6}$ alkyloxy wherein any one or more of the hydrogen atoms on the alkoxy group can be substituted by deuterium.

In certain embodiments, $R_1$ is not hydrogen. In other embodiments, $R_2$ is not hydrogen. In some embodiments, $R_3$ is not hydrogen. In other embodiments, $R_4$ is not hydrogen. In still other embodiments, $R_6$ is not hydrogen. In yet other embodiments, $R_7$ is not hydrogen. In yet other embodiments, $R_8$ is not hydrogen. In still other embodiments, $R_9$ is not hydrogen. In still other embodiments, $R_{10}$ is not hydrogen.

In certain embodiments, $R_1$ is not deuterium. In other embodiments, $R_2$ is not deuterium. In some embodiments, $R_3$ is not deuterium. In other embodiments, $R_4$ is not deuterium. In still other embodiments, $R_6$ is not deuterium. In yet other embodiments, $R_7$ is not deuterium. In yet other embodiments, $R_8$ is not deuterium. In still other embodiments, $R_9$ is not deuterium. In still other embodiments, $R_{10}$ is not deuterium.

In further embodiments, $R_2$ is not a $C_{1-6}$ alkyloxy. In some of these embodiments, $R_2$ is not —$OCH_3$, —$OCD_3$, —$OCHF_2$, or —$OCDF_2$. In other embodiments, $R_2$ is not —$OCD_3$ or —$OCDF_2$.

In other embodiments, $R_5$ is not —$CH_2$, —CHD or —$CD_2$;

In yet other embodiments, $R_6$ is not a $C_{1-6}$ alkyloxy. In some of these embodiments, $R_6$ is not —$OCH_3$, or —$OCD_3$;

In still other embodiments, $R_6$ is not a $C_{1-6}$ alkyl. In some of these embodiments, $R_6$ is not —$CH_3$, or —$CD_3$;

In other embodiments, $R_7$ is not a $C_{1-6}$ alkyloxy. In some of these embodiments, $R_7$ is not —$OCH_3$, —$OCD_3$, —$OCH_2CF_3$, —$OCD_2CF_3$, or —$O(CH_2)_3OCH_3$ wherein any of the hydrogen atoms in —$O(CH_2)_3OCH_3$ can be substituted by a deuterium.

In other embodiments, $R_8$ is not a $C_{1-6}$ alkyl. In some of these embodiments, $R_8$ is not —$CH_3$, or —$CD_3$;

In yet other embodiments, $R_8$ is not a $C_{1-6}$ alkyloxy.

In another embodiment of the invention, there are provided pharmaceutical compositions comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, for enteral, intravenous infusion, oral, parenteral, topical or ocular administration.

In yet another embodiment of the invention, there are provided pharmaceutical compositions comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, for the treatment of conditions involving the gastric $H^+$, $K^+$-ATPase, duodenal ulcers, other conditions mediated by gastric acid secretion, or psoriasis.

In another embodiment of the invention, there are provided methods of modulating the activity of the gastric $H^+$, $K^+$-ATPase, with one or more of the compounds or compositions of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof.

In still another embodiment of the invention, there are provided methods of treating a mammalian subject, particularly a human, suspected of having, or being prone to a disease or condition involving the gastric $H^+$, $K^+$-ATPase, gastric ulcers, duodenal ulcers, esophageal ulcers, other conditions mediated by gastric acid secretion, or psoriasis.

In some embodiments, the administering step in the above methods comprises administering the compound of the invention in some composition, i.e., a single tablet, pill, or capsule, or a single solution for intravenous injection, or a single drinkable solution, or a single dragee formulation or patch, wherein the amount administered is about 0.5 milligram to 80 milligram total daily dose.

In another embodiment of the invention, there are provided methods for treatment of gastric acid related diseases by inhibition of gastric acid secretion comprising administering to a mammalian subject in need of treatment a therapeutically effective amount of a gastric $H^+$, $K^+$-ATPase inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, so as to affect decreased inter-individual variation in plasma levels of said compound or a metabolite thereof during treatment of gastric acid related diseases as compared to the non-isotopically enriched compound.

In some embodiments, the inter-individual variation in plasma levels of the compounds of the invention, or metabolites thereof, is decreased by greater than about 5%, as compared to the non-isotopically enriched compounds. In other embodiments, the inter-individual variation in plasma levels of the compounds of the invention, or metabolites thereof, is decreased by greater than about 10%, as compared to the non-isotopically enriched compounds. In other embodiments, the inter-individual variation in plasma levels of the compounds of the invention, or metabolites thereof, is decreased by greater than about 20%, as compared to the non-isotopically enriched compounds. In other embodiments, the inter-individual variation in plasma levels of the compounds of the invention, or metabolites thereof, is decreased by greater than about 30%, as compared to the non-isotopically enriched compounds. In other embodiments, the inter-individual variation in plasma levels of the compounds of the invention, or metabolites thereof, is decreased by greater than about 40%, as compared to the non-isotopically enriched compounds. In other embodiments, the inter-individual variation in plasma levels of the compounds of the invention, or metabolites thereof, is decreased by greater than about 50%, as compared to the non-isotopically enriched compounds. Plasma levels of the compounds of the invention, or metabolites thereof, are measured by the methods of Li et al *Rapid Communications in Mass Spectrometry* 2005, 19(14), 1943-1950, which is hereby incorporated by reference in its entirety.

In another embodiment of the invention, there are provided methods for treatment of gastric acid related diseases by inhibition of gastric acid secretion comprising administering to a mammalian subject in need of treatment a therapeutically effective amount of a gastric $H^+$, $K^+$-ATPase inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, so as to affect increased average plasma levels of said compound or decreased average plasma levels of at least one metabolite of said compound per dosage unit as compared to the non-isotopically enriched compound.

In some embodiments, the average plasma levels of the compounds of the invention are increased by greater than about 5%, as compared to the non-isotopically enriched compounds. In other embodiments, the average plasma levels of the compounds of the invention are increased by greater than about 10%, as compared to the non-isotopically enriched compounds. In other embodiments, the average plasma levels of the compounds of the invention are increased by greater than about 20%, as compared to the non-isotopically enriched compounds. In other embodiments, the average plasma levels of the compounds of the invention are increased by greater than about 30%, as compared to the non-isotopically enriched compounds. In other embodiments, the average plasma levels of the compounds of the invention are increased by greater than about 40%, as compared to the non-isotopically enriched compounds. In other embodiments, the average plasma levels of the compounds of the invention are increased by greater than about 50%, as compared to the non-isotopically enriched compounds.

In some embodiments, the average plasma levels of a metabolite of the compounds of the invention are decreased by greater than about 5%, as compared to the non-isotopically enriched compounds. In other embodiments, the average plasma levels of a metabolite of the compounds of the invention are decreased by greater than about 10%, as compared to the non-isotopically enriched compounds. In other embodiments, the average plasma levels of a metabolite of the compounds of the invention are decreased by greater than about 20%, as compared to the non-isotopically enriched compounds. In other embodiments, the average plasma levels of a metabolite of the compounds of the invention are decreased by greater than about 30%, as compared to the non-isotopically enriched compounds. In other embodiments, the average plasma levels of a metabolite of the compounds of the invention are decreased by greater than about 40%, as compared to the non-isotopically enriched compounds. In other embodiments, the average plasma levels of a metabolite of the compounds of the invention are decreased by greater than about 50%, as compared to the non-isotopically enriched compounds.

Plasma levels of the compounds of the invention, or metabolites thereof, are measured by the methods of Li et al *Rapid Communications in Mass Spectrometry* 2005, 19(14), 1943-1950.

In another embodiment of the invention, there are provided methods for treatment of gastric acid related diseases by inhibition of gastric acid secretion comprising administering to a mammalian subject in need of treatment a therapeutically effective amount of a gastric $H^+$, $K^+$-ATPase inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, so as to affect a less pronounced increase in gastrin levels in mammalian subjects during treatment of gastric acid related diseases as compared to the non-isotopically enriched compound.

In another embodiment of the invention, there are provided methods for treatment of gastric acid related diseases by inhibition of gastric acid secretion comprising administering to a mammalian subject in need of treatment a therapeutically effective amount of a gastric $H^+$, $K^+$-ATPase inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, so as to affect a decreased inhibition of at least one cytochrome $P_{450}$ isoform in mammalian subjects during treatment of gastric acid related diseases as compared to the non-isotopically enriched compound. Examples of cytochrome $P_{450}$ isoforms in mammalian subjects include CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51 and the like.

In some embodiments, the decrease in inhibition of the cytochrome $P_{450}$ isoform by compounds of the invention is greater than about 5%, as compared to the non-isotopically enriched compounds. In other embodiments, the decrease in inhibition of the cytochrome $P_{450}$ isoform by compounds of the invention is greater than about 10%, as compared to the non-isotopically enriched compounds. In other embodiments, the decrease in inhibition of the cytochrome $P_{450}$ isoform by compounds of the invention is greater than about 20%, as compared to the non-isotopically enriched compounds. In other embodiments, the decrease in inhibition of the cytochrome $P_{450}$ isoform by compounds of the invention is greater than about 30%, as compared to the non-isotopically enriched compounds. In other embodiments, the decrease in inhibition of the cytochrome $P_{450}$ isoform by compounds of the invention is greater than about 40%, as compared to the non-isotopically enriched compounds. In other embodiments, the decrease in inhibition of the cytochrome $P_{450}$ isoform by compounds of the invention is greater than about 50%, as compared to the non-isotopically enriched compounds.

The inhibition of the cytochrome $P_{450}$ isoform is measured by the methods of Ko et al *British Journal of Clinical Pharmacology* 2000, 49(4), 343-351, which is hereby incorporated by reference in its entirety.

In another embodiment of the invention, there are provided methods for treatment of gastric acid related diseases by inhibition of gastric acid secretion comprising administering to a mammalian subject in need of treatment a therapeutically effective amount of a gastric $H^+$, $K^+$-ATPase inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, so as to affect an improved antisecretory effect during the treatment of gastric related diseases as compared to the non-isotopically enriched compound.

In another embodiment of the invention, there are provided methods for treatment of gastric acid related diseases by inhibition of gastric acid secretion comprising administering to a mammalian subject in need of treatment a therapeutically effective amount of a gastric $H^+$, $K^+$-ATPase inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, so as to affect an improved clinical effect (e.g., accelerated rate of healing and accelerated rate of symptom relief) during the treatment of gastric related diseases as compared to the non-isotopically enriched compound.

In another embodiment of the invention, there are provided oral multiple unit tablet pharmaceutical compositions comprising two components A and B, wherein component A comprises one or more antibacterial agent with similar or different activities, such as for example amoxicillin, clarithromycin, metronidazole, and the like, and a combination thereof, and component B comprises at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, in the form of pellets covered with an enteric coating polymer layer with mechanical properties such that the acid resistance of the enteric coated pellets is not significantly affected by compression of the pellets with the other tablet components during tableting, wherein component A is separated from component B by the enteric coating layer covering component B.

In still another embodiment of the invention, there are provided effervescent dosage forms comprising two components A and B, wherein, component A is one or more effervescent excipients, and component B is made up of a mixture comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, a beta blocking agent, such as for example atenolol, metoprolol, propranolol and the like, and optionally one or more pharmaceutically acceptable excipients.

In still another embodiment of the invention, there are provided oral multiple unit tablet pharmaceutical compositions comprising three components A, B and C, wherein component A comprises at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, in the form of pellets covered with an enteric coating polymer layer with mechanical properties such that the acid resistance of the enteric coated pellets is not significantly affected by compression of the pellets with the other tablet components during tableting, component B consisting of at least one Non Steroidal Anti-inflammatory Drug (NSAID), such as for example, Naproxen (Aleve), Ibuprofen (Motrin), Indomethacin (Indocin), Nabumetone (Relafen), and the like, and optional component C consisting of one or more pharmaceutically acceptable excipients, wherein component B is separated from component A by the enteric coating layer covering component A.

In yet another embodiment of the invention, there are provided methods for the treatment of a bacterial infection caused or mediated by *Helicobacter pylori*, comprising simultaneously, separately or sequentially administering to a mammalian subject in need, an effective amount of an Nitric Oxide releasing Non Steroidal Anti-inflammatory Drug (NSAID) and at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof.

In another embodiment of the invention, there are provided extended release pharmaceutical dosage forms comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, a hydrophilic or hydrophobic matrix, a water-soluble separating layer, an enteric coating layer, and optionally one or more pharmaceutically acceptable excipients.

In still another embodiment of the invention, there are provided enteric coated pharmaceutical dosage forms comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, a disruptable semi-permeable membrane and one or more swellable substances, wherein the dosage form has an instant inhibitor-releasing part and at least one delayed inhibitor-releasing part, and is capable of giving a discontinuous release of the compound in the form of at least two consecutive pulses separated in time from 0.1 up to 24 hours.

In still another embodiment of the invention, there are provided stable pharmaceutical dosage forms for oral administration to mammalian subjects which comprises at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, and optionally one or more pharmaceutical adjuvants, enclosed in an intermediate reactive layer comprising a gastric juice-resistant polymeric layered material partially neutralized with alkali and having cation exchange capacity and a gastric juice-resistant outer layer.

In yet another embodiment of the invention, there are provided compounds according to formula 1 having one of the following structures:

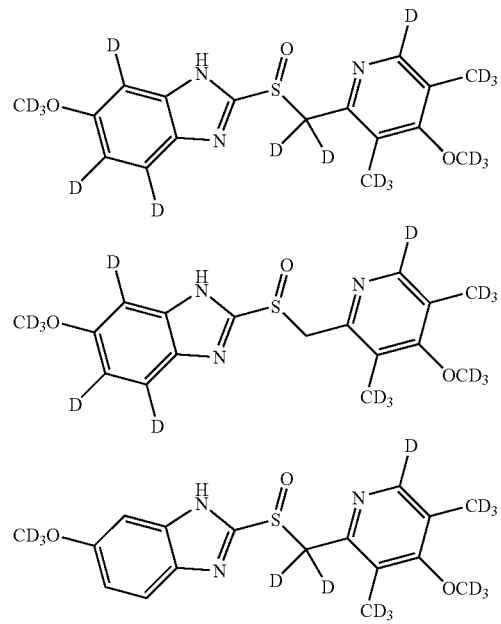

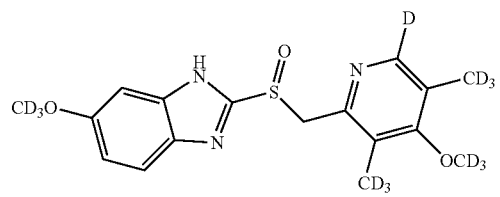
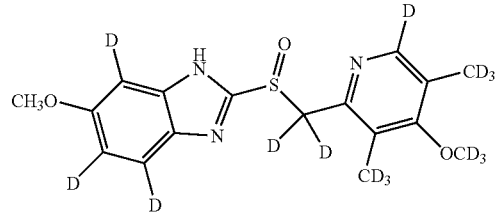
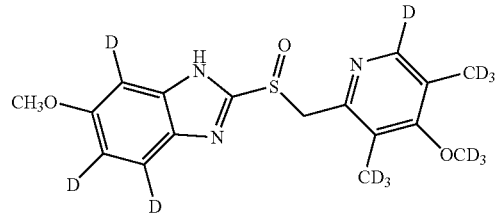
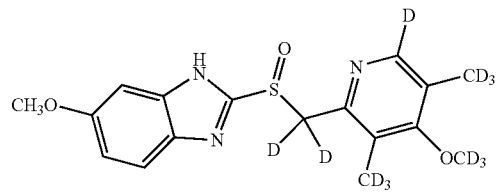
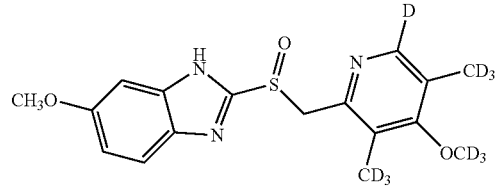
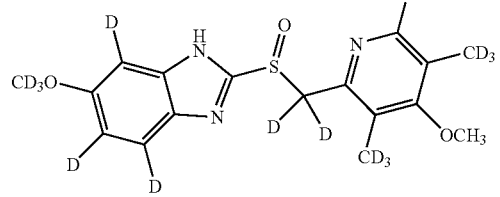
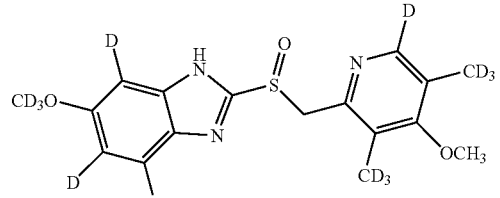
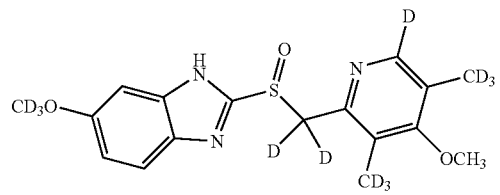
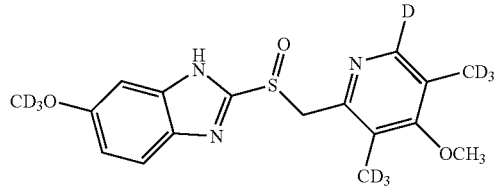
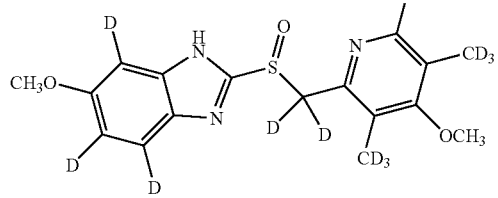
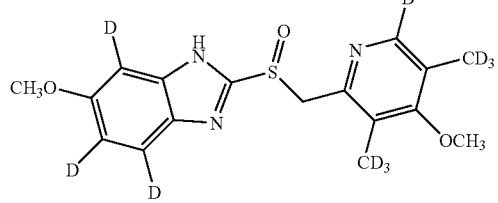
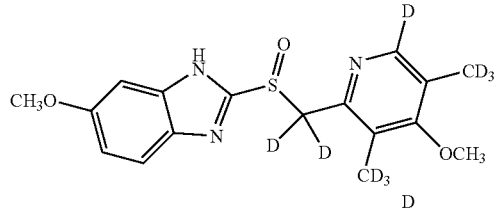
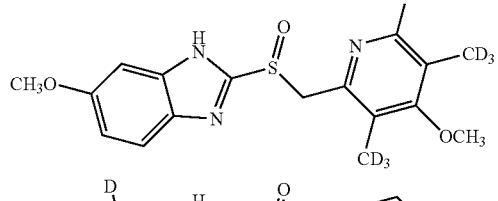
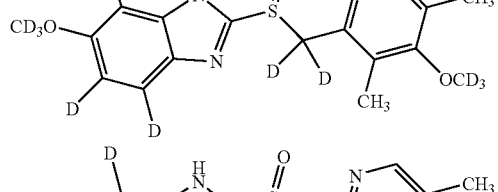
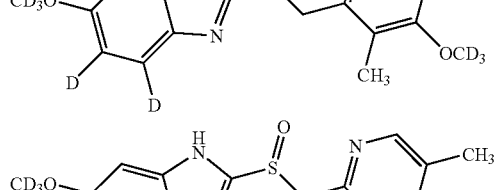
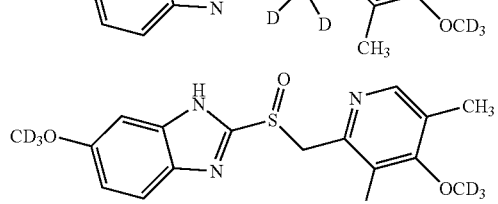

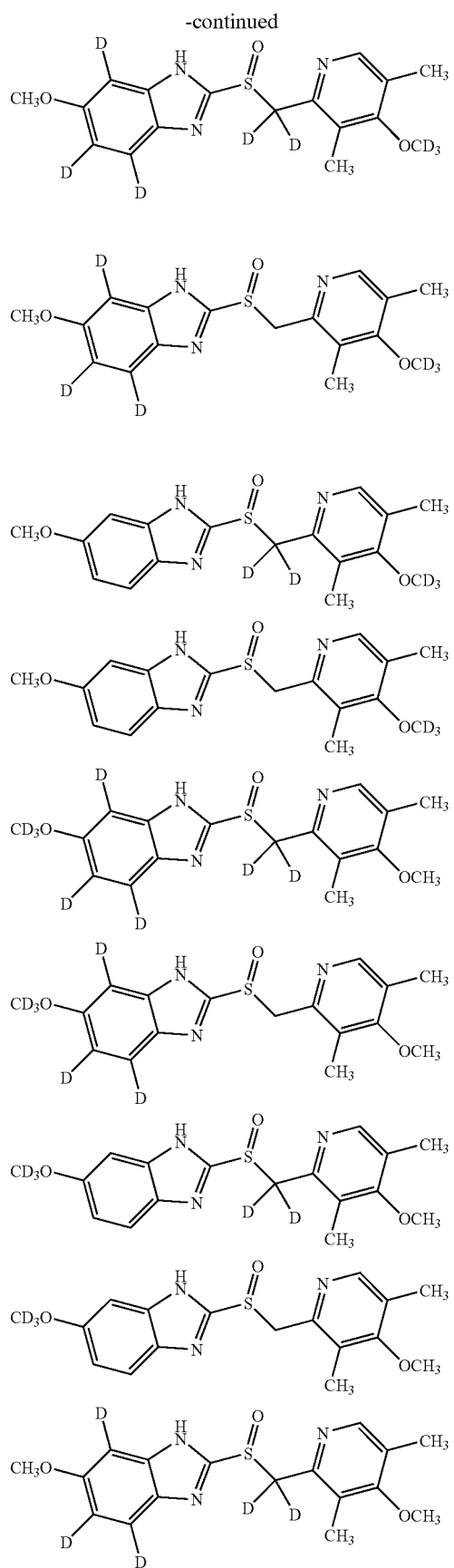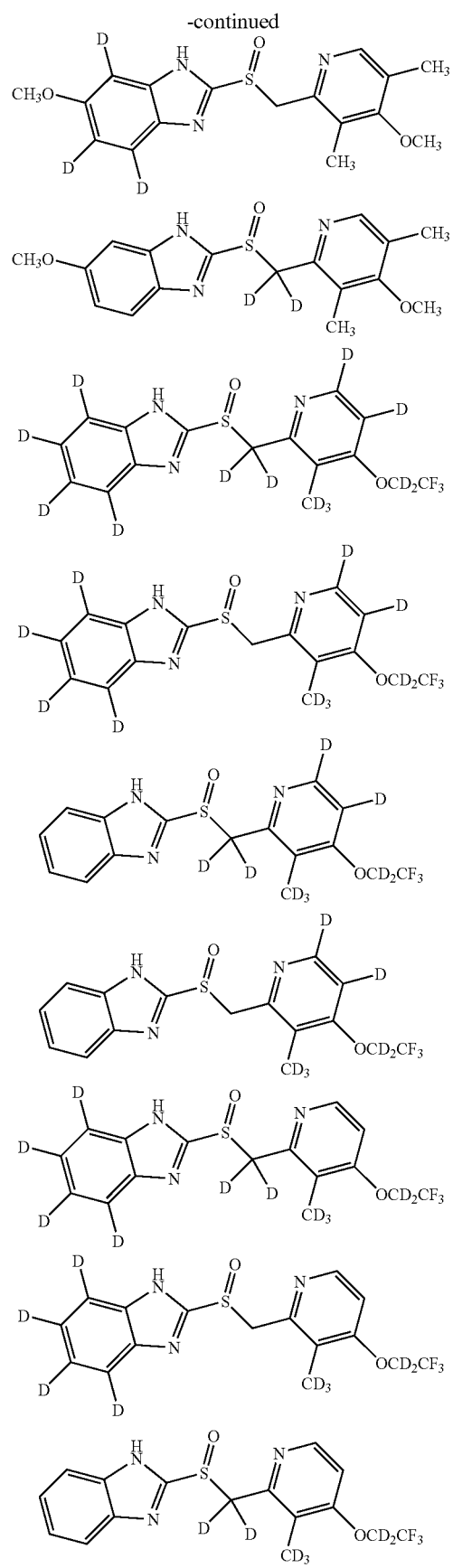

-continued
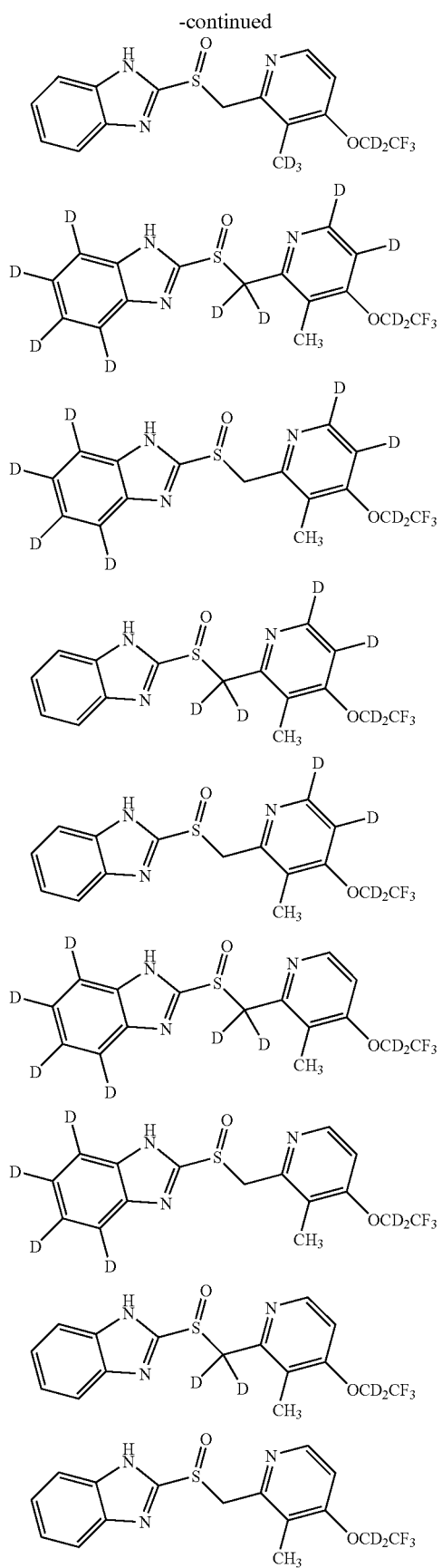
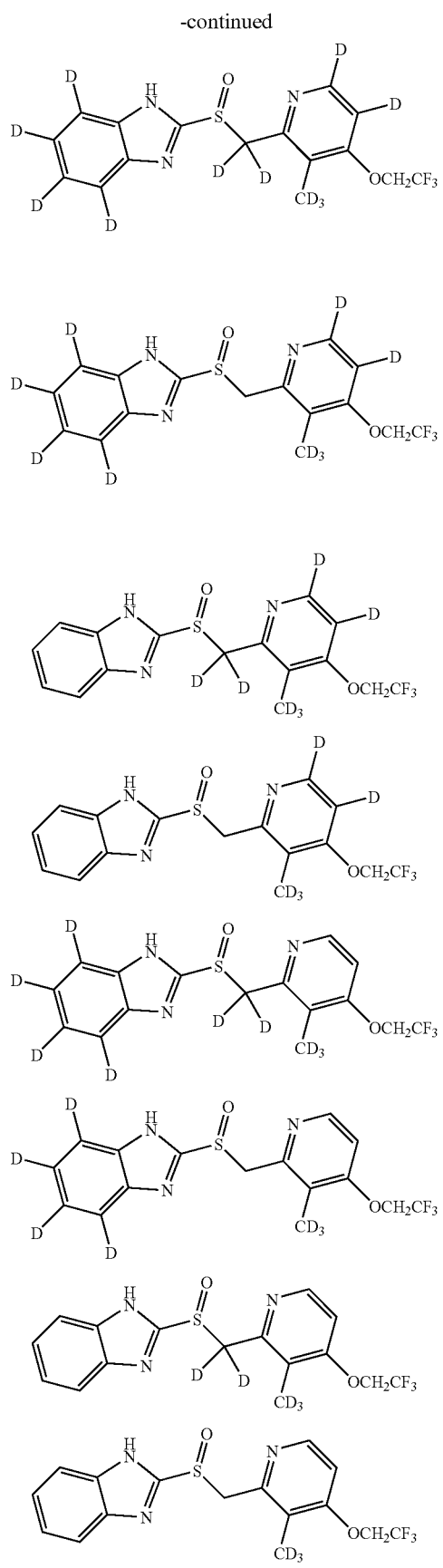

-continued
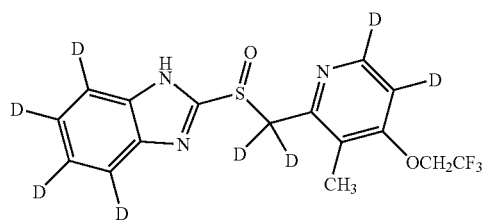
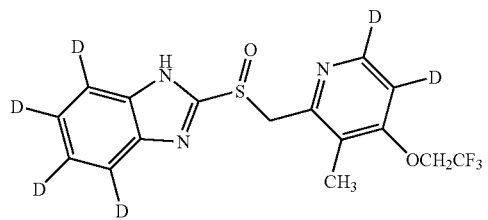
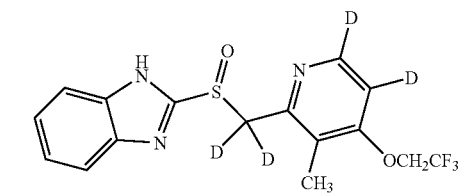
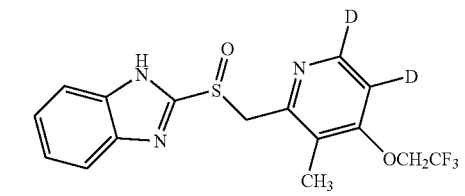
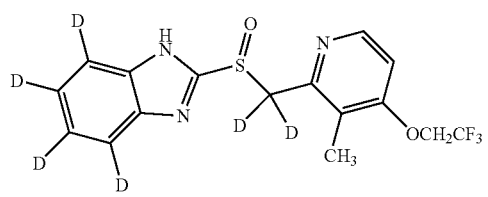
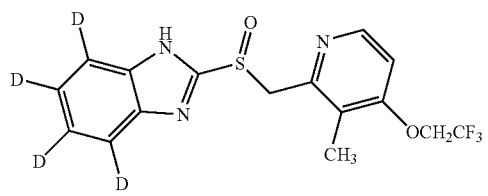
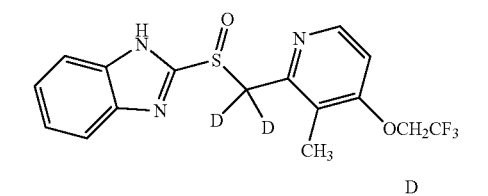
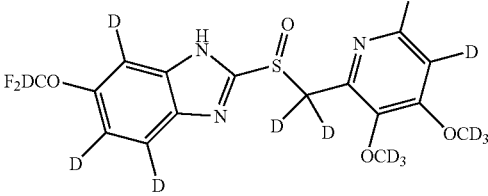
-continued
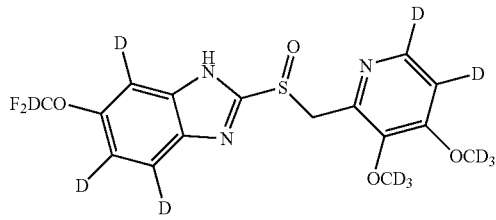
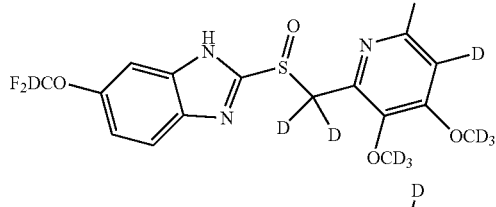
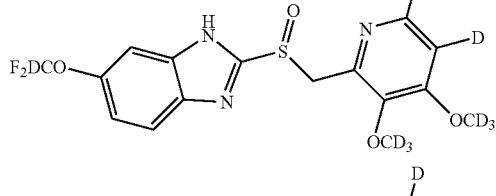
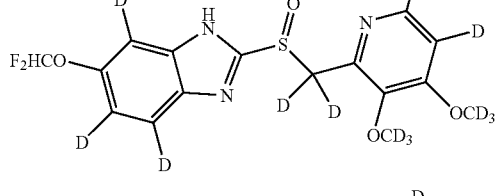
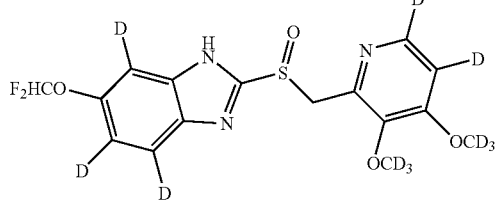
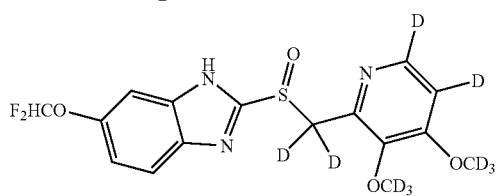
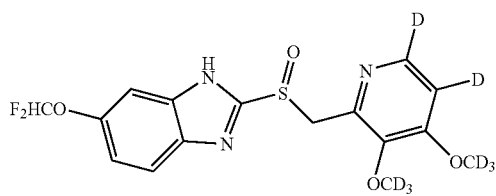
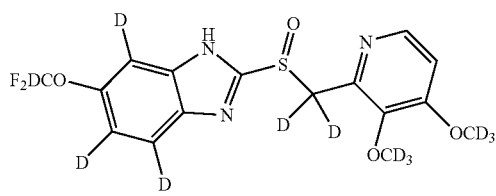

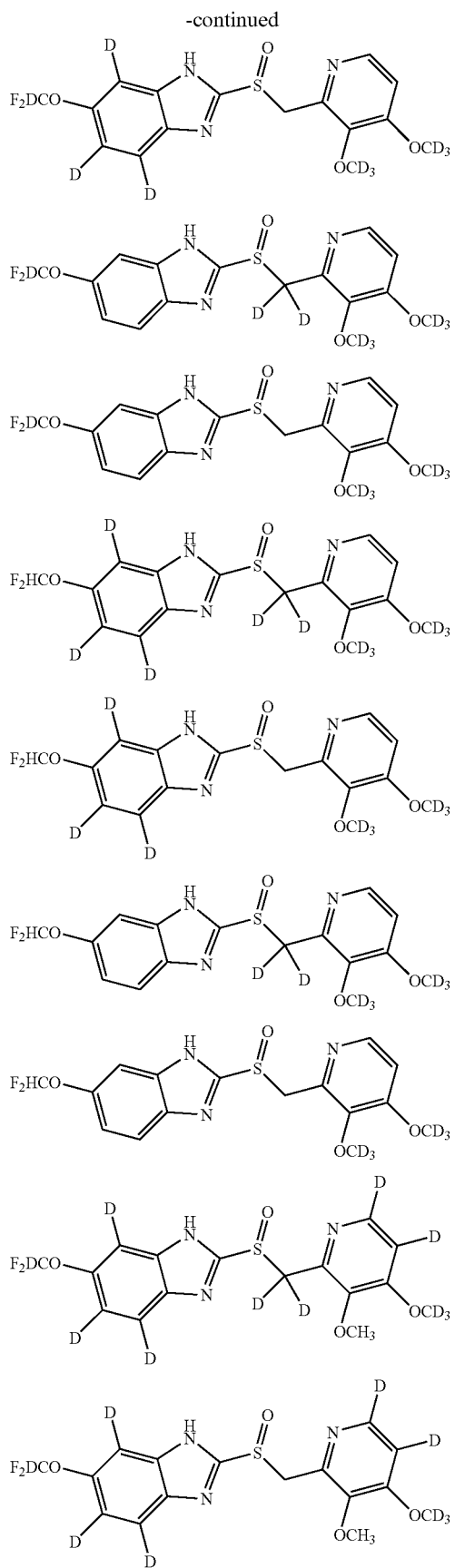
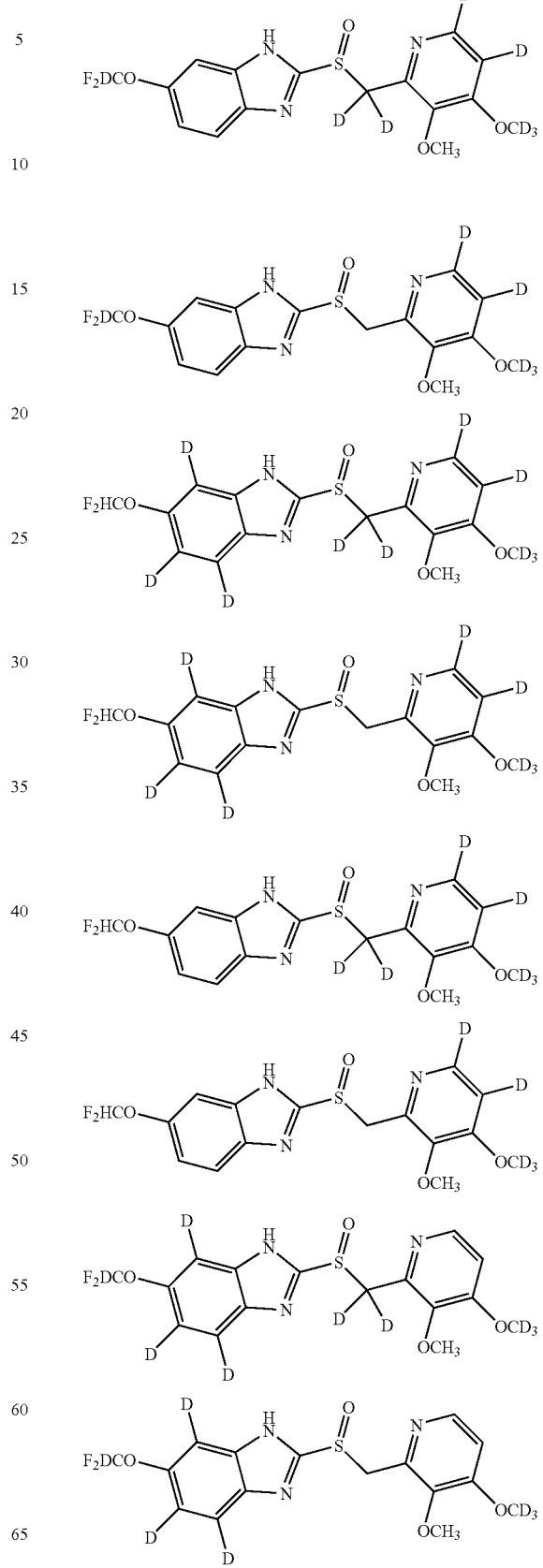

-continued
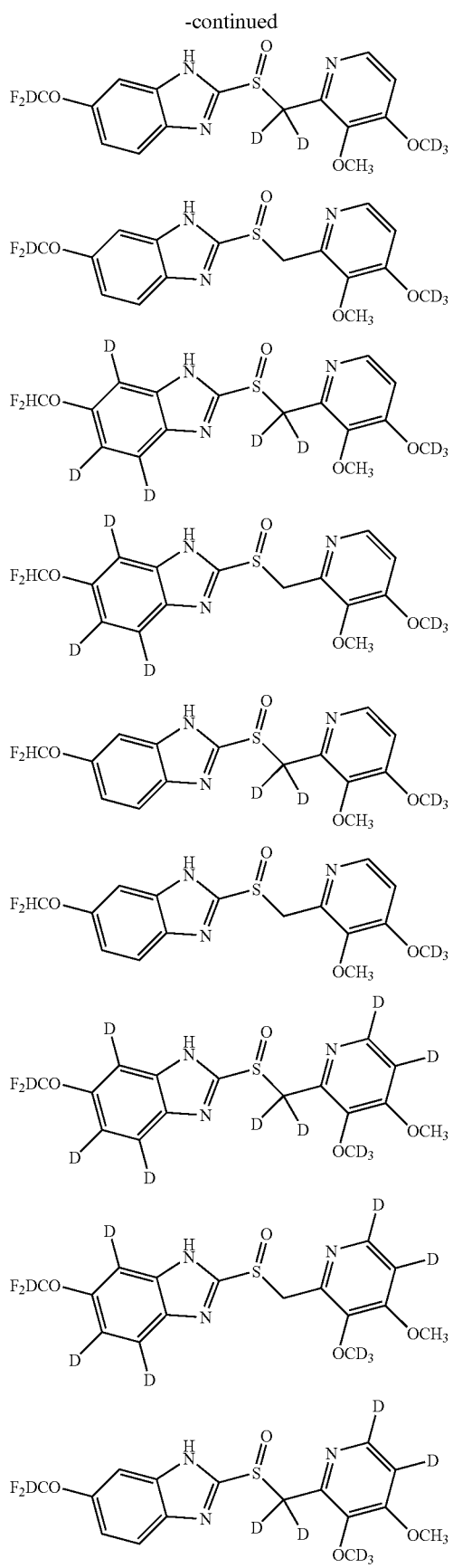
-continued
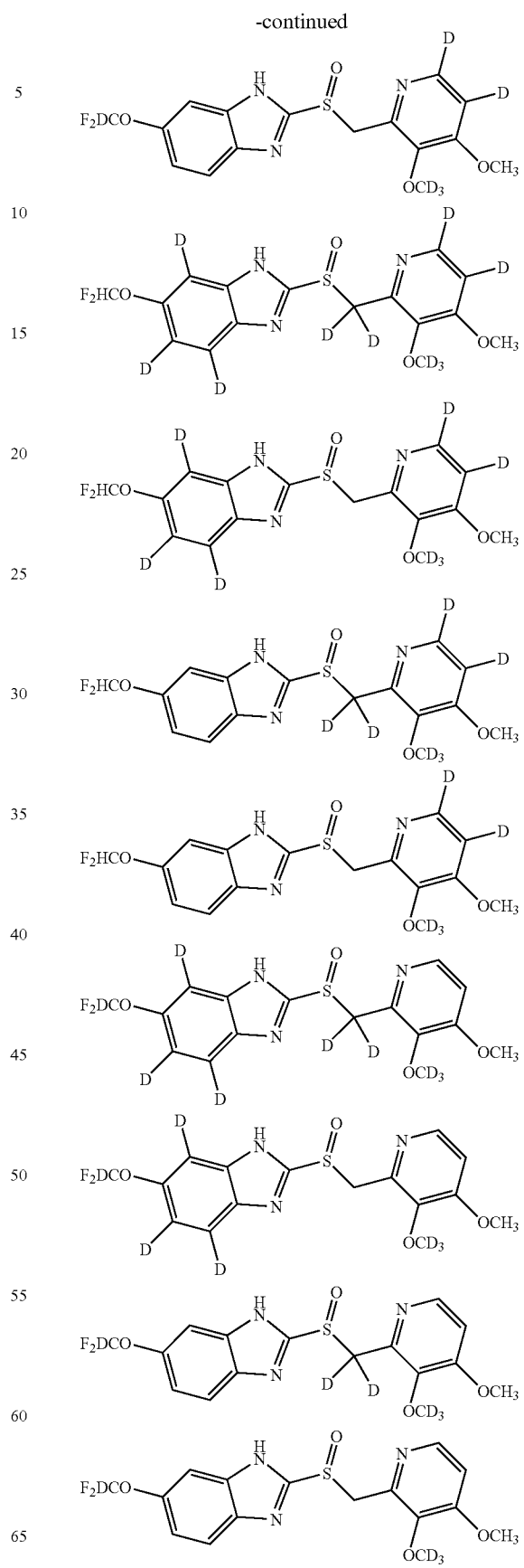

-continued

-continued
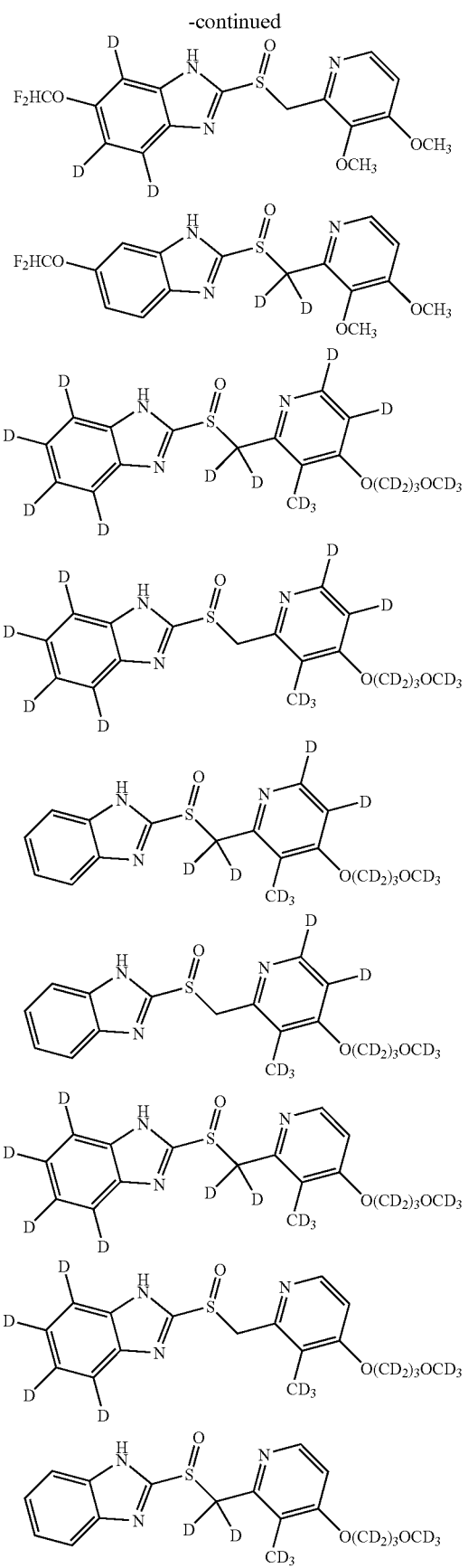
-continued
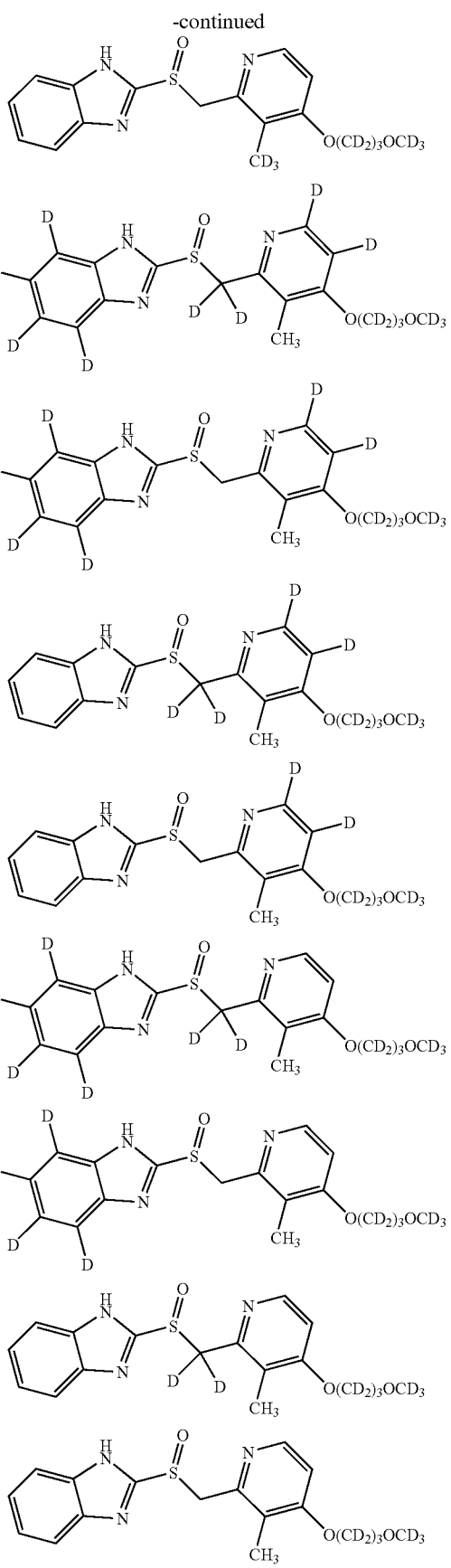

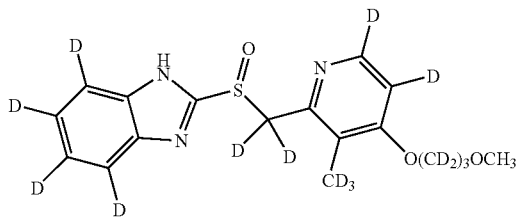
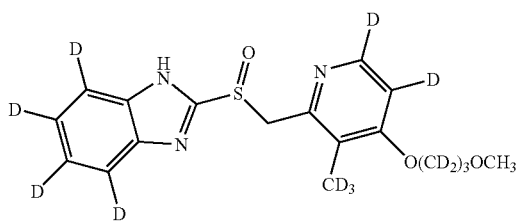
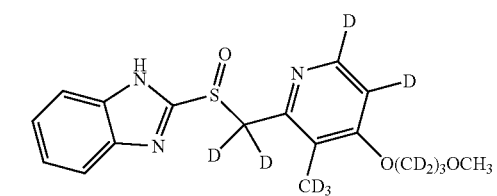
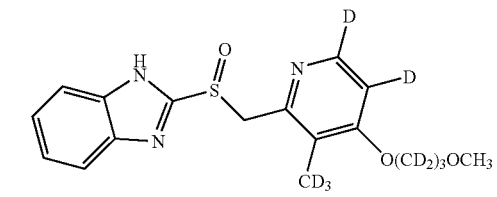
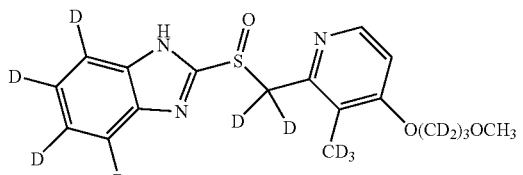
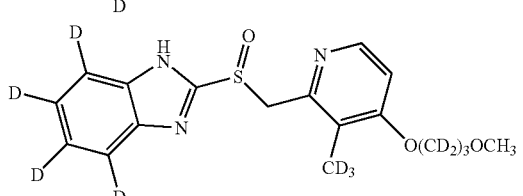
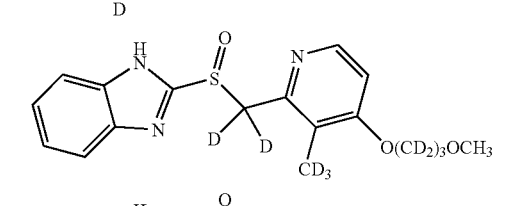
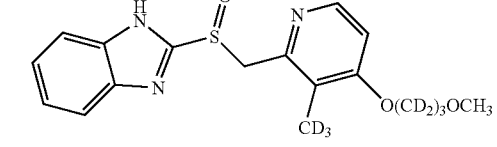
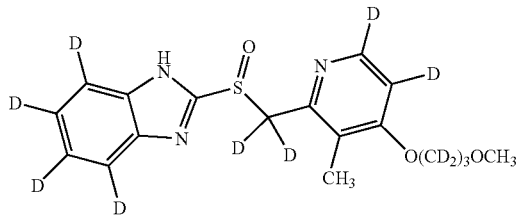
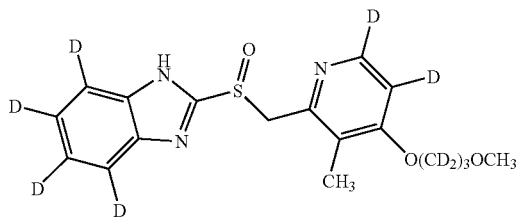
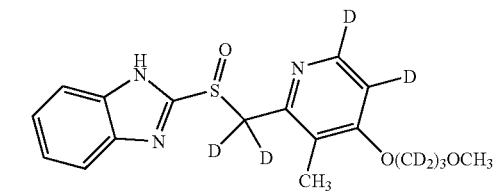
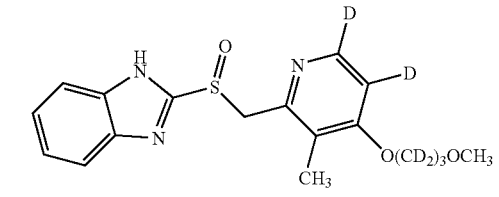
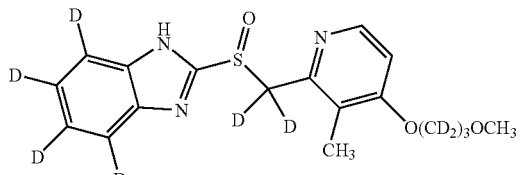
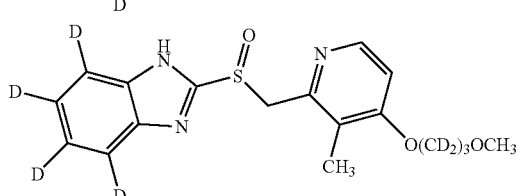
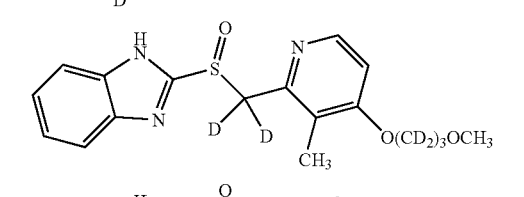
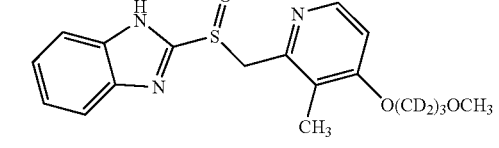

-continued
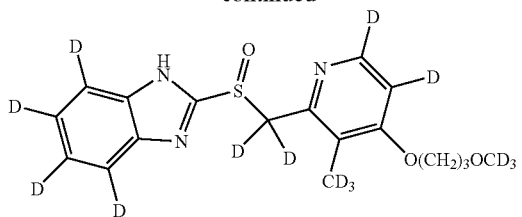
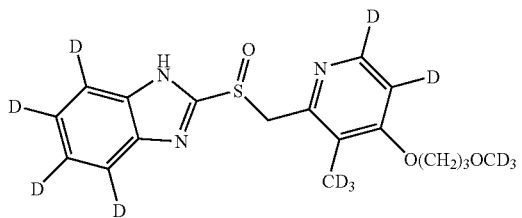
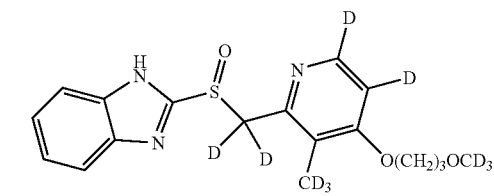
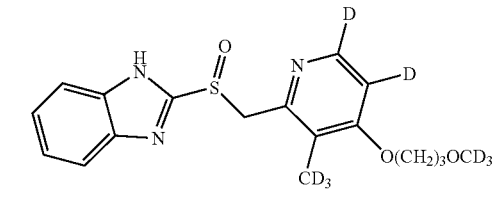
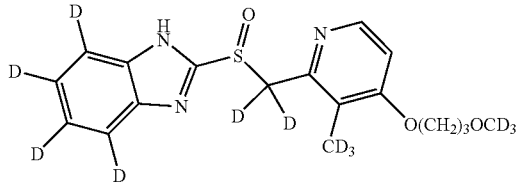
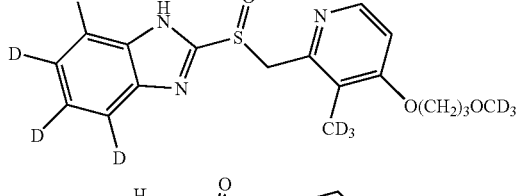
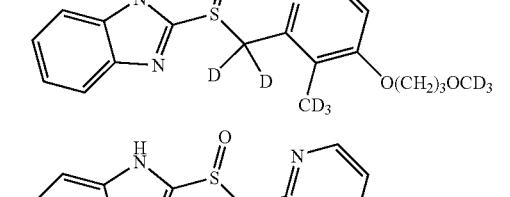
-continued
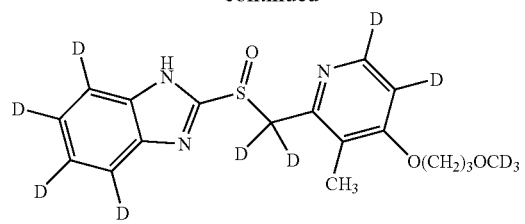
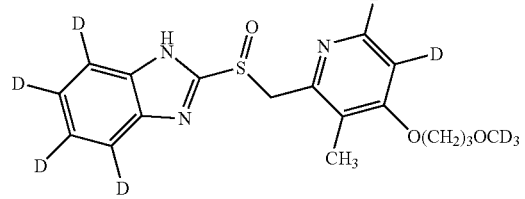
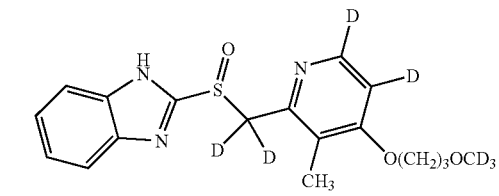
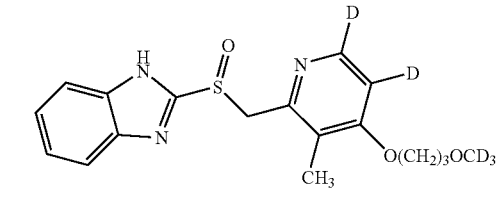
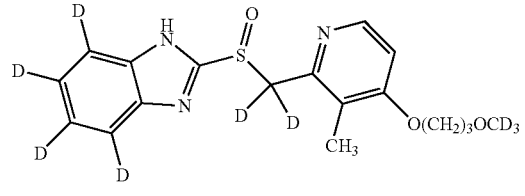
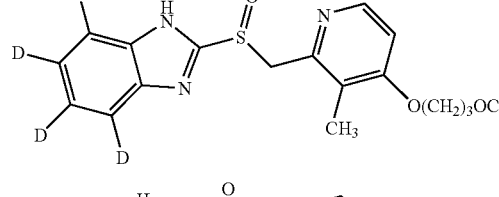
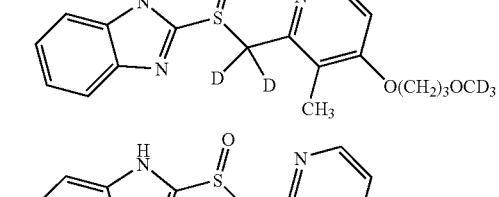

37
-continued
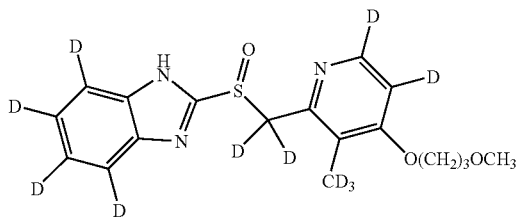
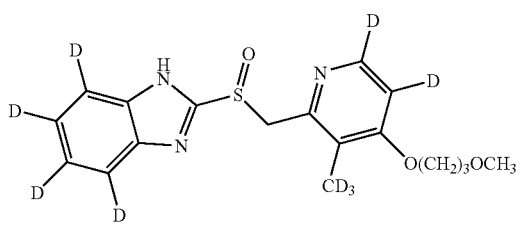
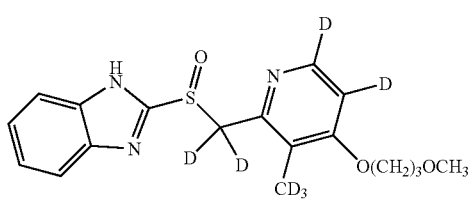
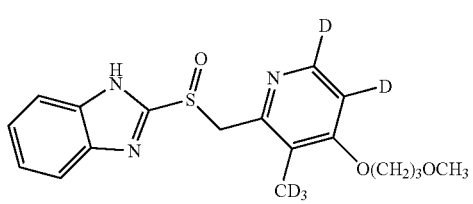
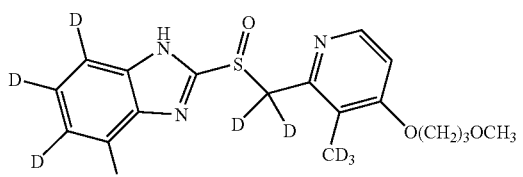
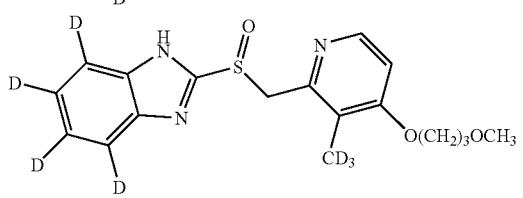
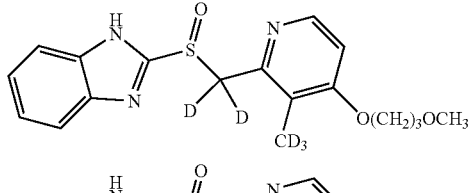
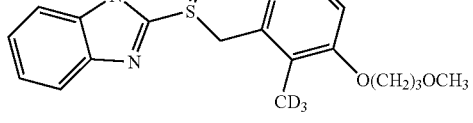
38
-continued
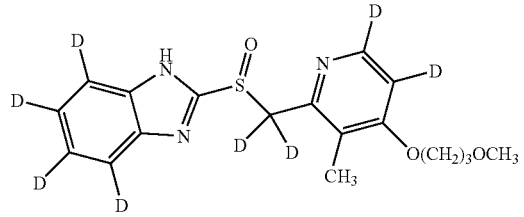
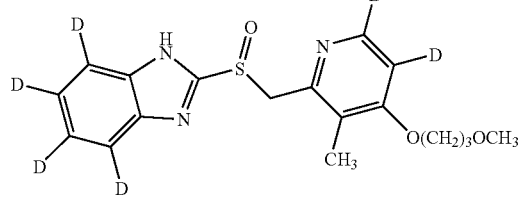
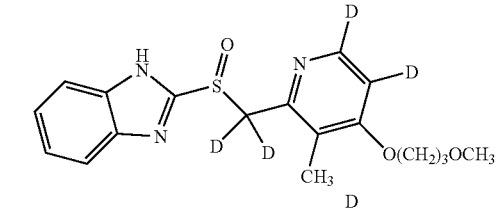
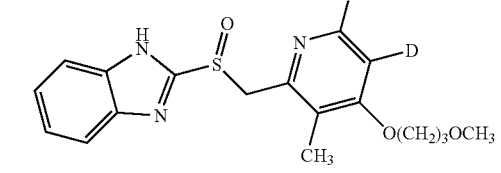
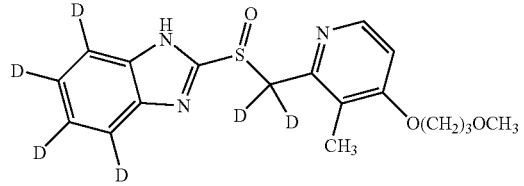
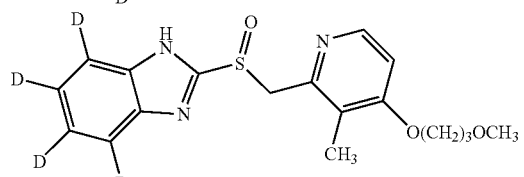
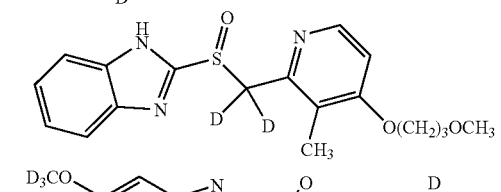
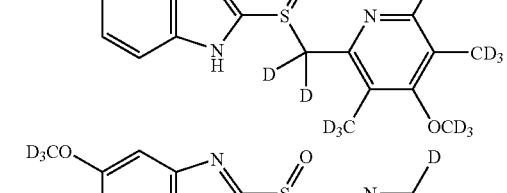
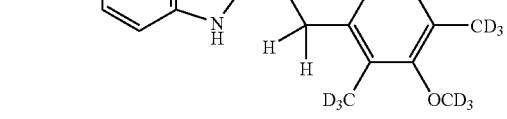

-continued

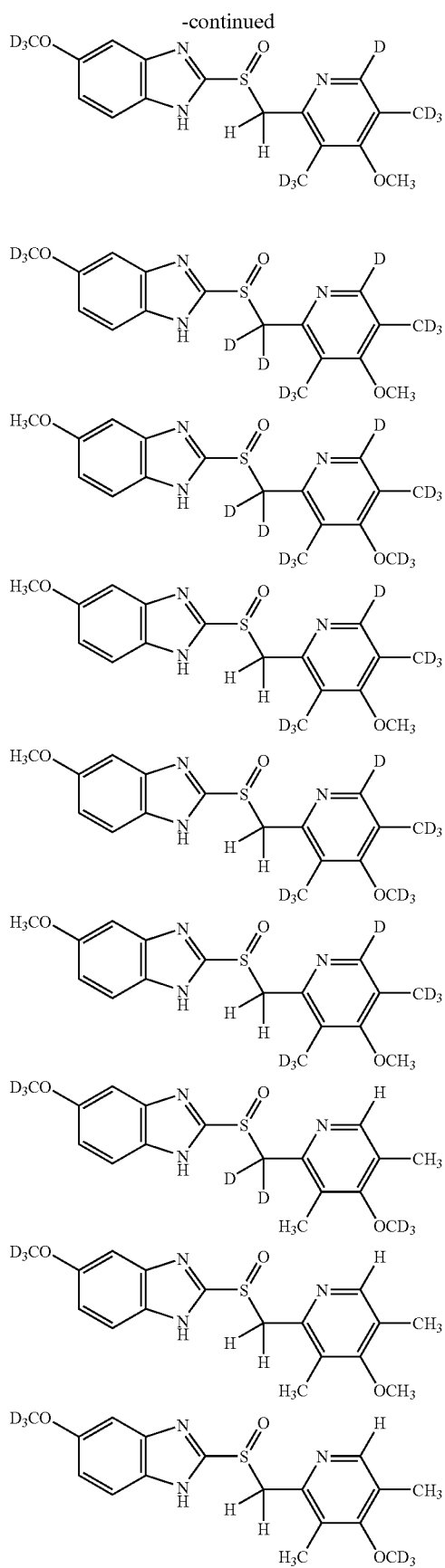
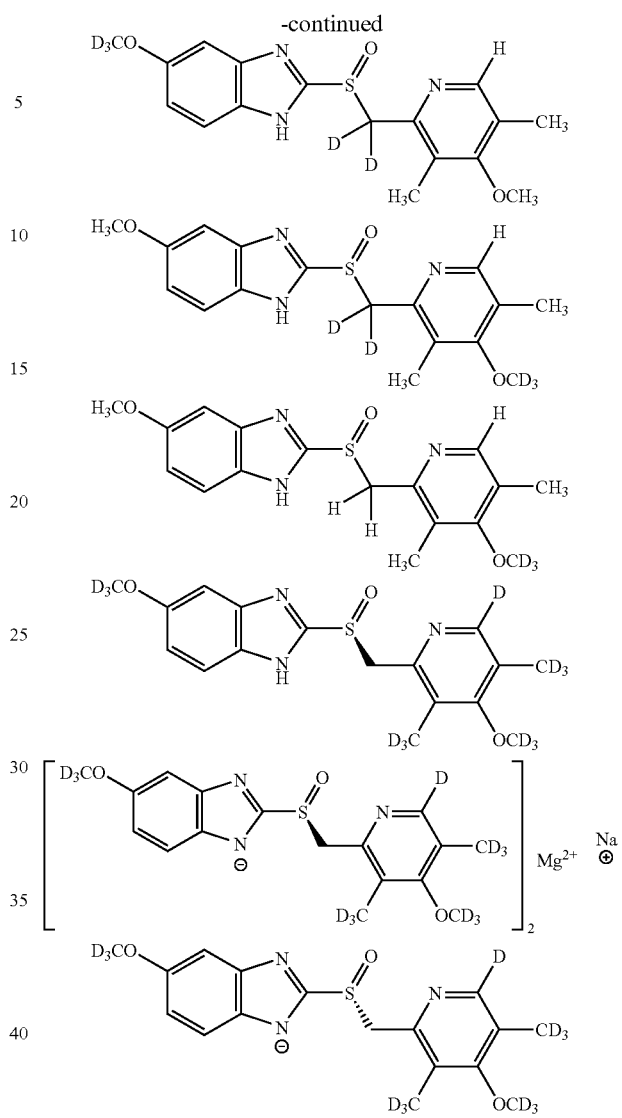

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt, solvate, or prodrug thereof.

The present invention is intended to include all isotopes of all atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopes of sulfur include $^{32}S$, $^{33}S$, $^{34}S$, and $^{36}S$. Isotopes of nitrogen include $^{14}N$ and $^{15}N$. Isotopes of oxygen include $^{16}O$, $^{17}O$, and $^{18}O$.

Isotopic hydrogen can be introduced into organic molecules by synthetic techniques that employ deuterated reagents whereby incorporation rates are pre-determined and/or by exchange techniques wherein incorporation rates are determined by equilibrium conditions and maybe highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. In addition, the molecule being labeled may be changed, depending upon the severity of the synthetic reaction employed. Exchange techniques, on the other hand, may yield lower tritium or deuterium incorporation, often with the isotope being distributed over many sites on the molecule, but offer the advantage that they do not require separate synthetic steps and are less likely to disrupt the structure of the molecule being labeled.

Unless otherwise indicated, when a substituent is deemed to be "optionally substituted," it is meant that the substituent is a group that may be substituted with one or more group(s) individually and independently selected from the group consisting of hydrogen, deuterium, alkyl, cycloalkyl, aryl, heteroaryl, heterocyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art examples of which may be found in references such as Greene and Wuts, Protective Groups in Organic Synthesis, 3$^{rd}$ Ed., John Wiley & Sons, New York, N.Y., 1999, which is incorporated by reference herein in its entirety.

The compounds according to this invention may occur as any reasonable tautomer as recognized by one skilled in the art or a mixture of such tautomers. The term "tautomer" or "tautomerism" refers to one of two or more structural isomers that exist in equilibrium and are readily converted from one isomeric form to another. Examples include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention. The following example of tautomerism is provided for reference:

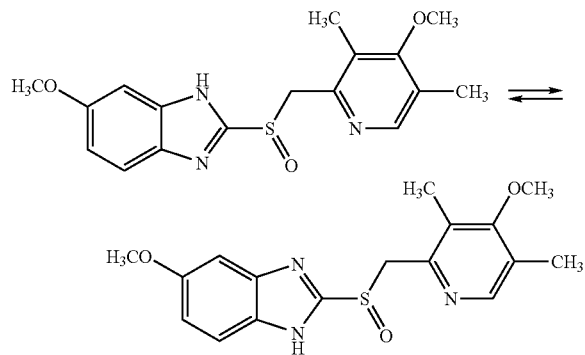

The compounds according to this invention may contain one or more asymmetric atoms and can thus occur as racemates and racemic mixtures, single enantiomers, diastereomeric mixtures or individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical atoms and therefore include various stereoisomers. All such isomeric forms of these compounds are expressly included in the present invention.

Each stereogenic carbon or sulfur may be of R or S configuration; Although the specific compounds exemplified in this application may be depicted in a particular configuration, compounds having the opposite stereochemistry at any given chiral center or mixtures thereof are also envisioned. When chiral centers are found in the derivatives of this invention, it is to be understood that this invention encompasses all possible stereoisomers.

The terms "optically pure compound" or "optically pure isomer" refers to a single stereoisomer of a chiral compound regardless of the configuration of the said compound.

The term "substantially homogeneous" refers to collections of molecules wherein at least about 80%, preferably at least about 90% and more preferably at least about 95% of the molecules are a single compound or a single stereoisomer thereof, or to collections of molecules wherein at least about 80%, preferably at least about 90% and more preferably at least about 95% of the molecules are fully substituted (e.g., deuterated) at the positions stated.

As used herein, the term "attached" signifies a stable covalent bond, certain preferred points of attachment being apparent to those skilled in the art.

The terms "optional" or "optionally" refer to occurrence or non-occurrence of the subsequently described event or circumstance, and that the description includes instances where said event or circumstance occurs and instances where it does not. For example, the sentence "optionally substituted alkyl group" means that the alkyl group may or may not be substituted and the description includes both a substituted and an unsubstituted alkyl group.

The term "effective amount" of a compound refers a sufficient amount of the compound that provides a desired effect but with no—or acceptable—toxicity. This amount may vary from subject to subject, depending on the species, age, and physical condition of the subject, the severity of the disease that is being treated, the particular compound used, its mode of administration, and the like. A suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

When used in conjunction with a compound of this invention, the terms "elicit", "eliciting," "modulator", "modulate", "modulating", "regulator", "regulate" or "regulating" the activity refer to a compound that can act as an inhibitor, or an antagonist of a particular enzyme or receptor, such as for example the gastric $H^+$, $K^+$-ATPase and the like.

The terms "drug", "therapeutic agent" and "chemotherapeutic agent", refer to a compound or compounds and pharmaceutically acceptable compositions thereof that are administered to mammalian subjects as prophylactic or remedy in the treatment of a disease or medical condition. Such compounds may be administered to the subject via oral formulation, inhalation, ocular application, transdermal formulation or by injection.

The term "subject" refers to an animal, preferably a mammal, and most preferably a human, who is the object of treatment, observation or experiment. The mammal may be selected from the group consisting of mice, rats, hamsters, gerbils, rabbits, guinea pigs, dogs, cats, sheep, goats, cows, horses, giraffes, platypuses, primates, such as monkeys, chimpanzees, and apes, and humans.

The term "therapeutically effective amount" is used to indicate an amount of an active compound, or pharmaceutical agent, that elicits the biological or medicinal response indicated. This response may occur in a tissue, system (animal including human) that is being sought by a researcher, veterinarian, medical doctor or other clinician.

The terms "treating," "treatment," "therapeutic," or "therapy" do not necessarily mean total loss of nociception. Any alleviation of any undesired signs or symptoms of a disease, such as inhibition of the gastric $H^+$, $K^+$-ATPase, duodenal ulcers and other conditions mediated by gastric acid secretion, or a subset of these conditions, to any extent can be considered treatment or therapy. Furthermore, treatment may include acts that may worsen the patient's overall feeling of well-being or appearance.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, Lithium perchlorate, copper (II) trifluoromethanesulfonate, copper (II) tetrafluoroborate and the like. Certain Lewis acids may have optically pure ligands attached to the electron acceptor atom, as set forth in Corey, E. J. Angewandte Chemie, International Edition (2002), 41(10), 1650-1667; Aspinall, H. C. Chemical Reviews (Washington, D.C., United States) (2002), 102(6), 1807-1850; Groger, H. Chemistry—A European Journal (2001), 7(24), 5246-5251; Davies, H. M. L. Chemtracts (2001), 14(11), 642-645; Wan, Y. Chemtracts (2001), 14(11), 610-615; Kim, Y. H. Accounts of Chemical Research (2001), 34(12), 955-962; Seebach, D. Angewandte Chemie, International Edition (2001), 40(1), 92-138; Blaser, H. U. Applied Catalysis, A: General (2001), 221(1-2), 119-143; Yet, L. Angewandte Chemie, International Edition (2001), 40(5), 875-877; Jorgensen, K. A. Angewandte Chemie, International Edition (2000), 39(20), 3558-3588; Dias, L. C. Current Organic Chemistry (2000), 4(3), 305-342; Spindler, F. Enantiomer (1999), 4(6), 557-568; Fodor, K. Enantiomer (1999), 4(6), 497-511; Shimizu, K. D.; Comprehensive Asymmetric Catalysis I-III (1999), 3, 1389-1399; Kagan, H. B. Comprehensive Asymmetric Catalysis I-III (1999), 1, 9-30; Mikami, K. Lewis Acid Reagents (1999), 93-136 and all references cited therein. Such Lewis acids may be used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, acetyl chloride, succinic anhydride, diketene, diallyl carbonate, carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell or an attraction for an electron-rich reactant and as such would be obvious to one of ordinary skill and knowledge in the art. The definition of "electrophile" includes but is not limited to: hydronium, acylium, Lewis acids, such as for example, Boron trifluoride and the like, halogens, such as for example $Br_2$ and the like, carbocations, such as for example tert-butyl cation and the like, diazomethane, trimethylsilyldiazomethane, alkyl halides, such as for example methyl iodide, trideuteromethyl iodide ($CD_3I$), benzyl bromide and the like, alkyl triflates, such as for example methyl triflate and the like, alkyl sulfonates, such as for example ethyl toluenesulfonate, butyl methanesulfonate, dimethylsulfate, hexadeuterodimethylsulfate (($CD_3$)$_2SO_4$) and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-toluenesulfonyl chloride and the like, silyl halides, such as for example trimethylsilyl chloride, tert-butyldimethylsilyl chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "leaving group" (LG) refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, methanesulfonate, tolylsulfonate, trifluoromethanesulfonate, acetate, trichloroacetate, benzoate and the like.

The term "oxidant" refers to any reagent that will increase the oxidation state of an atom, such as for example, hydrogen, carbon, nitrogen, sulfur, phosphorus and the like in the starting material by either adding an oxygen to this atom or removing an electron from this atom and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "reducing reagent" refers to any reagent that will decrease the oxidation state of an atom in the starting material by either adding a hydrogen to this atom, or adding an electron to this atom, or by removing an oxygen from this atom and as such would be obvious to one of ordinary skill and knowledge in the art. The definition of "reducing reagent" includes but is not limited to: borane-dimethyl sulfide complex, 9-borabicyclo[3.3.1.]nonane (9-BBN), catechol borane, lithium borohydride, lithium borodeuteride, sodium borohydride, sodium borodeuteride, sodium borohydride-methanol complex, potassium borohydride, sodium hydroxyborohydride, lithium triethylborohydride, lithium n-butylborohydride, sodium cyanoborohydride, sodium cyanoborodeuteride, calcium (II) borohydride, lithium aluminum hydride, lithium aluminum deuteride, diisobutylAluminum hydride, n-butyl-diisobutylaluminum hydride, Sodium bis-methoxyethoxyAluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl) carbodiimide (EDCI), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbomene-2,3-dicarboximido)-1,1,3,3-tetramethyluronium tetrafluoroborate (TNTU), O-(N-succinimidyl)-1,1, 3,3-tetramethyluronium tetrafluoroborate (TSTU), tetramethylfluoroformamidinium hexafluorophosphate and the like.

The term "removable protecting group" or "protecting group" refers to any group which when bound to a functionality, such as the oxygen atom of a hydroxyl or carboxyl group or the Nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:

a) Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl) ethoxymethyl, enthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like;

b) Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (trityl), α-naphthyldiphenylmethyl, (4-methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris (levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,I] fluorenylmethyl)-4,4'-dimethoxytrityl, 9-anthryl, 9-(9-phenyl)xanthenyl, 9-(9-phenyl-10-oxo)anthryl and the like;

c) Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

d) —C(O)$R_{20}$, where $R_{20}$ is selected from the group consisting of alkyl, substituted alkyl, aryl and more specifically $R_{20}$=hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like;

e) —C(O)O$R_{20}$, where $R_{20}$ is selected from the group consisting of alkyl, substituted alkyl, aryl and more specifically $R_{20}$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenyl-ethyl, 2-(4-nitrophenyl)ethyl, 2-(2,4-dinitrophenyl)ethyl, 2-cyano-1-phenylethyl, thiobenzyl, 4-ethoxy-1-naphthyl and the like. Other examples of hydroxyl protecting groups are given in Greene and Wutts, above.

The definition of "amino protecting group" includes but is not limited to:

a) 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxy-benzyl, m-chloro-p-acyloxybenzyl, p-(dihydroxyboryl)benzyl, 5-benzisoxazolylmethyl, 2-(trifluoromethyl)-6-chromonytmethyl, m-nitrophenyl, 3,5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzene-sulfonyl, N-2,6-dimethyl-4-methoxybenzenesulfonyl, N-pentamethylbenzenesulfonyl, N-2,3,5,6-tetramethyl-4-methoxybenzenesulfonyl and the like;

b) —C(O)O$R_{20}$, where $R_{20}$ is selected from the group consisting of alkyl, substituted alkyl, aryl and more specifically $R_{20}$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10,10-dioxo-10,10,10, 10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethyl-ethyl, 2-[(2-nitrophenyl)dithio]-1-phenylethyl, tert-butyl, 1-adamantyl, 2-adamantyl, Vinyl, allyl, 1-Isopropylallyl, cinnamyl. 4-nitrocinnamyl, 3-(3-pyridyl)prop-2-enyl, 8-quinolyl, N-Hydroxypiperidinyl, alkyldithio, benzyl, p-methoxybenzyl, p-nitrobenzyl, p-bromobenzyl. p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-Iodoethyl, isobomyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like. Other examples of amino protecting groups are given in Greene and Wutts, above.

The definition of "carboxyl protecting group" includes but is not limited to:

2-N-(morpholino)ethyl, choline, methyl, methoxyethyl, 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl. α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-Sulfobenzyl, 4-azidomethoxybenzyl, 4-{a/-[1-(4,4-dimethyl-2,6-dioxocyclohexylidene)-3-methylbutyl]amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like. Other examples of carboxyl protecting groups are given in Greene and Wutts, above.

The definition of "thiol protecting group" includes but is not limited to:

a) Alkyl, benzyl, 4-methoxybenzyl, 2-hydroxybenzyl, 4-hydroxybenzyl, 2-acetoxybenzyl, 4-acetoxybenzyl, 4-nitrobenzyl, 2,4,6-trimethylbenzyl, 2,4,6-trimethoxybenzyl, 4-picolyl, 2-quinolinylmethyl, 2-picolyl n-oxide, 9-anthrylmethyl, 9-fluorenylmethyl, xanthenyl, ferrocenylmethyl and the like;

b) Diphenylmethyl, bis(4-methoxyphenyl)methyl, 5-dibenzosuberyl, triphenylmethyl, diphenyl-4-pyridylmethyl, phenyl, 2,4-dinitrophenyl, tert-butyl, 1-adamantyl and the like;

c) Methoxymethyl, isobutoxymethyl, benzyloxymethyl, 2-tetrahydropyranyl, benzylthiomethyl, phenylthiomethyl, acetamidomethyl, trimethylacetamidomethyl, benzamidomethyl, allyloxycarbonylaminomethyl, phenylacetamidomethyl, phthalimidomethyl, acetyl, carboxy-, cyanomethyl and the like;

d) (2-nitro-1-phenyl)ethyl, 2-(2,4-dinitrophenyl)ethyl, 2-(4'-pyridyl)ethyl, 2-cyanoethyl, 2-(trimethylsilyl)ethyl, 2,2-bis(carboethoxy)ethyl, 1-(3-nitrophenyl)-2-benzoylethyl, 2-phenylsulfonylethyl, 1-(4-methylphenylsulfonyl)-2-methylpro4-2-yl and the like;

e) Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

f) Benzoyl, trifluoroacetyl, N-[[(4-biphenylyl)isopropoxy]carbonyl]-N-methyl-γ-aminothiobutyrate, N-(t-butoxycarbonyl)-N-methyl-γ-aminothiobutyrate and the like;

g) 2,2,2-Trichloroethoxycarbonyl, tert-butoxycarbonyl, benzyloxycarbonyl, 4-methoxybenzyloxycarbonyl and the like;

h) N-(Ethylamino)carbonyl, N-(methoxymethylamino)carbonyl and the like;

i) Ethylthio, tert-butylthio, phenylthio, substituted phenylthio and the like;

j) (Dimethylphosphino)thioyl, (diphenylphosphino)thioyl and the like;

k) Sulfonate, alkyloxycarbonylthio, benzyloxycarbonylthio, 3-nitro-2-pyridinethio and the like;

l) Tricarbonyl[1,2,3,4,5-η]-2,4-cyclohexadien-1-yl]-iron (1+) and the like. Other examples of thiol protecting groups are given in Greene and Wutts, above.

The term "amino acid" refers to any of the naturally occurring amino acids, as well as synthetic analogs and derivatives thereof. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like. One of skill in the art will appreciate that the term "amino acid" can also include beta-, gamma-, delta-, omega-amino acids, and the like. Unnatural amino acids are also known in the art, as set forth in, Natchus, M. G. Organic Synthesis: Theory and Applications (2001), 5, 89-196; Ager, D. J. Current Opinion in Drug Discovery & Development (2001), 4(6), 800; Reginato, G. Recent Research Developments in Organic Chemistry (2000), 4(Pt. 1), 351-359; Dougherty, D. A. Current Opinion in Chemical Biology (2000), 4(6), 645-652; Lesley, S. A. Drugs and the Pharmaceutical Sciences (2000), 101(Peptide and Protein Drug Analysis), 191-205; Pojitkov, A. E. Journal of Molecular Catalysis B: Enzymatic (2000), 10(1-3), 47-55; Ager, D. J. Speciality Chemicals (1999), 19(1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group. The particular protecting group employed is not critical.

The term "prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of .beta.-Lactam antibiotics," Pharm. Biotech. 11, 345-365; Gaignault et al. (1996) "Designing Prodrugs and Bioprecursors I. Carrier Prodrugs," Pract. Med. Chem. 671-696; Asghamejad, "Improving Oral Drug Transport", in Transport Processes in Pharmaceutical Systems, G. L. Amidon, P. 1. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3): 183-209 (1999); Browne, "Fosphenytoin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8(1): 1-38 (1992); Fleisher et al. "Improved oral drug delivery: solubility limitations overcome by the use of prodrugs", Adv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989).

In light of the purposes described for the present invention, all references to reagents ordinarily containing hydrogens, hydrides, or protons may include partially or fully deuterated versions (containing deuterium, deuteride, or deuteronium) as required to affect transformation to the improved drug substances outlined herein.

The term "halogen", "halide" or "halo" includes fluorine, chlorine, bromine, and iodine.

The terms "alkyl" and "substituted alkyl" are interchangeable and include substituted, optionally substituted and unsubstituted $C_1$-$C_{10}$ straight chain saturated aliphatic hydrocarbon groups, substituted, optionally substituted and unsubstituted $C_2$-$C_{10}$ straight chain unsaturated aliphatic hydrocarbon groups, substituted, optionally substituted and unsubstituted $C_2$-$C_{10}$ branched saturated aliphatic hydrocarbon groups, substituted and unsubstituted $C_2$-$C_{10}$ branched unsaturated aliphatic hydrocarbon groups, substituted, optionally substituted and unsubstituted $C_3$-$C_8$ cyclic saturated aliphatic hydrocarbon groups, substituted, optionally substituted and unsubstituted $C_5$-$C_8$ cyclic unsaturated aliphatic hydrocarbon groups having the specified number of carbon atoms. For example, the definition of "alkyl" shall include but is not limited to: methyl (Me), trideuteromethyl (—$CD_3$), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group consisting of hydrogen, deuterium, halogen, —OH, —SH, —$NH_2$, —CN, —$NO_2$, =O, =$CH_2$, trihalomethyl, carbamoyl, aryl$C_{0-10}$alkyl, heteroaryl$C_{0-10}$alkyl, $C_{1-10}$alkyloxy, aryl$C_{0-10}$alkyloxy, $C_{1-10}$alkylthio, aryl$C_{0-10}$alkylthio, $C_{1-10}$alkylamino, aryl$C_{0-10}$alkylamino, N-aryl-N—$C_{0-10}$alkylamino, $C_{1-10}$alkylcarbonyl, aryl$C_{0-10}$alkylcarbonyl, $C_{1-10}$alkylcarboxy, aryl$C_{0-10}$alkylcarboxy, $C_{1-10}$alkylcarbonylamino, aryl$C_{0-10}$alkylcarbonylamino, tetrahydrofuryl, morpholinyl, piperazinyl, hydroxypyronyl, —$C_{0-10}$alkylCOOR$_{21}$ and —$C_{0-10}$alkylCONR$_{22}$R$_{23}$ wherein R$_{21}$, R$_{22}$ and R$_{23}$ are independently selected from the group consisting of hydrogen, deuterium, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined herein.

In light of the purposes described for the present invention, all references to "alkyl" groups or any groups ordinarily containing C—H bonds may include partially or fully deuterated versions as required to affect the improvements outlined herein.

The term "alkyloxy" (e.g. methoxy, ethoxy, propyloxy, allyloxy, cyclohexyloxy) represents a substituted or unsubstituted alkyl group as defined above having the indicated number of carbon atoms attached through an oxygen bridge. The term "alkyloxyalkyl" represents an alkyloxy group attached through an alkyl or substituted alkyl group as defined above having the indicated number of carbon atoms.

The term "alkyloxycarbonyl" (e.g. methoxycarbonyl, ethoxycarbonyl, tert-butoxycarbonyl, allyloxycarbonyl) represents a substituted or unsubstituted alkyloxy group as defined above having the indicated number of carbon atoms attached through a carbonyl bridge.

The term "alkylthio" (e.g. methylthio, ethylthio, propylthio, cyclohexenylthio and the like) represents a substituted or unsubstituted alkyl group as defined above having the indicated number of carbon atoms attached through a sulfur bridge. The term "alkylthioalkyl" represents an alkylthio group attached through an alkyl or substituted alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, and the like) represents one or two substituted or unsubstituted alkyl groups as defined above having the indicated number of carbon atoms attached through an amine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylaminoalkyl" represents an alkylamino group attached through a substituted or unsubstituted alkyl group as defined above having the indicated number of carbon atoms.

The term "alkylhydrazino" (e.g. methylhydrazino, diethylhydrazino, butylhydrazino, (2-cyclopentyl)propylhydrazino, cyclohexanehydrazino, and the like) represents one or two substituted or unsubstituted alkyl groups as defined above having the indicated number of carbon atoms attached through a nitrogen atom of a hydrazine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylhydrazinoalkyl" represents an alkylhydrazino group attached through a substituted or unsubstituted alkyl group as defined above having the indicated number of carbon atoms.

The term "alkylcarbonyl" (e.g. cyclooctylcarbonyl, pentylcarbonyl, 3-hexenylcarbonyl and the like) represents a substituted or unsubstituted alkyl group as defined above having the indicated number of carbon atoms attached through a carbonyl group. The term "alkylcarbonylalkyl" represents an alkylcarbonyl group attached through a substituted or unsubstituted alkyl group as defined above having the indicated number of carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl and the like) represents an alkylcarbonyl group as defined above wherein the carbonyl is in turn attached through the nitrogen atom of an amino group. The nitrogen group may itself be substituted with a substituted or unsubstituted alkyl or aryl group. The term "alkylcarbonylaminoalkyl" represents an alkylcarbonylamino group attached through a substituted or unsubstituted alkyl group as defined above having the indicated number of carbon atoms.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, or polysubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphthyl and the like). The aryl substituents are independently selected from the group consisting of hydrogen, deuterium, halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from the group consisting of hydrogen, deuterium, alkyl, aryl or R$_{22}$ and R$_{23}$ are taken together with the nitrogen to which they are attached forming a saturated cyclic or unsaturated cyclic system containing 3 to 8 carbon atoms with at least one substituent as defined above.

The definition of "aryl" includes but is not limited to phenyl, pentadeuterophenyl, biphenyl, naphthyl, dihydronaphthyl, tetrahydronaphthyl, indenyl, indanyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through a substituted or unsubstituted alkyl group as defined above having the indicated number of carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl) propylcarbonyl, (2-chloronaphthyl)pentenyl-carbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of carbon atoms attached through an oxygen bridge. The term "aryloxyalkyl" represents an aryloxy group attached through a substituted or unsubstituted alkyl group as defined above having the indicated number of carbon atoms.

The term "aryloxycarbonyl" (e.g. phenoxycarbonyl, naphthoxycarbonyl) represents a substituted or unsubstituted aryloxy group as defined above having the indicated number of carbon atoms attached through a carbonyl bridge.

The term "arylthio" (e.g. phenylthio, naphthylthio, 3-bromophenylthio, and the like) represents an aryl or substituted aryl group as defined above having the indicated number of carbon atoms attached through a sulfur bridge. The term "arylthioalkyl" represents an arylthio group attached through a substituted or unsubstituted alkyl group as defined above having the indicated number of carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of carbon atoms attached through an amine bridge. The term "arylaminoalkyl" represents an arylamino group attached through a substituted or unsubstituted alkyl group as defined above having the indicated number of carbon atoms. The term "arylalkylamino" represents an aryl group attached through an alkylamino group as defined above having the indicated number of carbon atoms. The term "N-aryl-N-alkylamino" (e.g. N-phenyl-N-methylamino, N-naphthyl-N-butylamino, and the like) represents one aryl and one a substituted or unsubstituted alkyl group as defined above having the indicated number of carbon atoms independently attached through an amine bridge.

The term "arylhydrazino" (e.g. phenylhydrazino, naphthylhydrazino, 4-methoxyphenylhydrazino, and the like) represents one or two aryl groups as defined above having the indicated number of carbon atoms attached through a hydrazine bridge. The term "arylhydrazinoalkyl" represents an arylhydrazino group attached through a substituted or unsubstituted alkyl group as defined above having the indicated number of carbon atoms. The term "arylalkylhydrazino" represents an aryl group attached through an alkylhydrazino group as defined above having the indicated number of carbon atoms. The term "N-aryl-N-alkylhydrazino" (e.g. N-phenyl-N-methylhydrazino, N-naphthyl-N-butylhydrazino, and the like) represents one aryl and one a substituted or unsubstituted alkyl group as defined above having the indicated number of carbon atoms independently attached through an amine atom of a hydrazine bridge.

The term "arylcarboxy" (e.g. phenylcarboxy, naphthylcarboxy, 3-fluorophenylcarboxy and the like) represents an arylcarbonyl group as defined above wherein the carbonyl is in turn attached through an oxygen bridge. The term "arylcarboxyalkyl" represents an arylcarboxy group attached through a substituted or unsubstituted alkyl group as defined above having the indicated number of carbon atoms.

The term "arylcarbonylamino" (e.g. phenylcarbonylamino, naphthylcarbonylamino, 2-methylphenylcarbonylamino and the like) represents an arylcarbonyl group as defined above wherein the carbonyl is in turn attached through the nitrogen atom of an amino group. The nitrogen group may itself be substituted with a substituted or unsubstituted alkyl or aryl group. The term "arylcarbonylaminoalkyl" represents an arylcarbonylamino group attached through a substituted or unsubstituted alkyl group as defined above having the indicated number of carbon atoms. The Nitrogen group may itself be substituted with a substituted or unsubstituted alkyl or aryl group.

The term "arylcarbonylhydrazino" (e.g. phenylcarbonylhydrazino, naphthylcarbonylhydrazino, and the like) represents an arylcarbonyl group as defined above wherein the carbonyl is in turn attached through the Nitrogen atom of a hydrazino group.

The terms "heteroaryl", "heterocycle" or "heterocyclic" refers to a monovalent unsaturated group having a single ring or multiple condensed rings, from 1 to 13 carbon atoms and from 1 to 10 hetero atoms selected from the group consisting of nitrogen, sulfur, and oxygen, within the ring. The heteroaryl groups in this invention can be optionally substituted with 1 to 10 substituents selected from the group consisting of: hydrogen, deuterium, halogen, —OH, —SH, —CN, —NO$_2$, trihalomethyl, hydroxypyronyl, $C_{1-10}$alkyl, aryl$C_{0-10}$ alkyl, $C_{0-10}$alkyloxy$C_{0-10}$alkyl, aryl$C_{0-10}$alkyloxy$C_{0-10}$ alkyl, $C_{0-10}$alkylthio$C_{0-10}$alkyl, aryl$C_{0-10}$alkylthio$C_{0-10}$ alkyl, $C_{0-10}$alkylamino$C_{0-10}$alkyl, aryl$C_{0-10}$alkylamino$C_{0-10}$ alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$ alkyl, $C_{1-10}$alkylcarboxy$C_{0-10}$alkyl, aryl$C_{0-10}$alkylcarboxy$C_{0-10}$ alkyl, $C_{1-10}$alkylcarbonylamino$C_{0-10}$alkyl, aryl$C_{0-10}$ alkylcarbonylamino$C_{0-10}$alkyl, —$C_{0-10}$alkylCOOR$_{21}$, and —$C_{0-10}$ alkylCONR$_{22}$R$_{23}$ wherein R$_{21}$, R$_{22}$ and R$_{23}$ are independently selected from the group consisting of hydrogen, deuterium, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, deuterobenzimidazolyl, dideuterobenzimidazolyl, trideuterobenzimidazolyl, tetradeuterobenzimidazolyl, pyridyl, deuteropyridyl, dideuteropyridyl, trideuteropyridyl, tetradeuteropyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4]triazolyl-3-carboxylic acid amide, 2,6-diamino-N6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, 5-methoxy-1H-benzoimidazolyl, 3-ethylpyridyl, 5-methyl-2-phenyl-oxazolyl, 5-methyl-2-thiophen-2-yl-oxazolyl, 2-furan-2-yl-5-methyl-oxazolyl, 3-methyl-3H-quinazolin-4-one, 4-methyl-2H-phthalazin-1-one, 2-ethyl-6-methyl-3H-pyrimidin-4-one, 5-methoxy-3-methyl-3H-imidazo[4,5-b]pyridine and the like. For the purposes of this application, the terms "heteroaryl", "heterocycle" or "heterocyclic" do not include carbohydrate rings (i.e. mono- or oligosaccharides).

The term "saturated heterocyclic" represents an unsubstituted, mono-, and polysubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl, DBU, and the like).

The saturated heterocyclic substituents are independently selected from the group consisting of halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyl oxy$C_{0-10}$alkyl, $C_{0-10}$alkylthio$C_{0-10}$alkyl, aryl$C_{0-10}$alkylthio $C_{0-10}$alkyl, $C_{0-10}$alkylamino$C_{0-10}$alkyl, aryl$C_{0-10}$alkylamino $C_{0-10}$alkyl, N-aryl-N—$C_{0-10}$alkylamino$C_{0-10}$alkyl, $C_{0-10}$alkylcarbonyl$C_{0-10}$alkyl, aryl$C_{0-10}$alkylcarbonyl$C_{0-10}$ alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$ alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from the group consisting of hydrogen, deuterium, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of saturated heterocyclic includes but is not limited to pyrazolidinyl, piperidinyl, 1,4-dioxanyl, morpholinyl, 1,4-dithienyl, thiomorpholinyl, piperazinyl, quinuclidinyl, and the like.

The term "alpha-beta-unsaturated carbonyl" refers to a molecule that has a carbonyl group directly attached to a double or triple bonded carbon and which would be obvious to one of ordinary skill and knowledge in the art. The definition of alpha-beta-unsaturated carbonyl includes but is not limited to acrolein, methyl vinyl ketone, and the like.

The term "acetal" refers to a molecule that contains a carbon atom $C_1$ that is directly attached to a hydrogen atom ($H_1$), a substituted carbon atom ($C_2$) and two oxygen atoms ($O_1$ and $O_2$). These oxygen atoms are in turn attached to other substituted carbon atoms ($C_3$ and $C_4$), which would be obvious to one of ordinary skill and knowledge in the art of acetal includes but is not limited to 1,1-dimethoxypropane, 1,1-bis-allyloxybutane and the like.

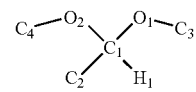

The term "cyclic acetal" refers to an acetal as defined above where $C_3$ and $C_4$, together with the oxygen atoms to which they are attached, combine thru an alkyl bridge to form a 5- to 10-membered ring, which would be obvious to one of ordinary skill and knowledge in the art. The definition of cyclic acetal includes but is not limited to 2-methyl-[1,3]dioxolane, 2-ethyl-[1,3]dioxane, 2-phenyl-[1,3]dioxane, 2-phenyl-hexahydro-pyrano[3,2-d][1,3]dioxine and the like.

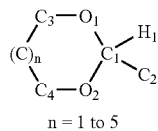

n = 1 to 5

The term "ketal" refers to a molecule that contains a carbon atom $C_1$ that is directly attached to two substituted carbon atom ($C_2$ and $C_3$) and two oxygen atoms ($O_1$ and $O_2$. These oxygen atoms are in turn attached to other substituted carbon atoms ($C_4$ and $C_5$), which would be obvious to one of ordinary skill and knowledge in the art. The definition of acetal includes but is not limited to 2,2-dimethoxy-butane, 3,3-diethoxy-pentane and the like.

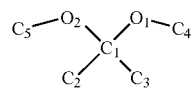

The term "cyclic ketal" refers to a ketal as defined above where $C_4$ and $C_5$, together with the oxygen atoms to which they are attached, combine thru an alkyl bridge to form a 5- to 10-membered ring, which would be obvious to one of ordinary skill and knowledge in the art. The definition of cyclic acetal includes but is not limited to 2,2,4,5-tetramethyl-[1,3] dioxolane, 2,2-diethyl-[1,3]dioxepane, 2,2-dimethyl-hexahydro-pyrano[3,2-d][1,3]dioxine and the like.

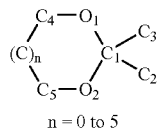

n = 0 to 5

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines a solution, typically one that is aqueous or partially aqueous, that dissolves chemical compounds of interest and may stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "gastric related diseases" defines a medical or physiological condition that includes, but is not limited to, peptic ulcer, duodenal ulcer, stomach ulcer, gastric ulcer, chronic gastritis, gastro-esophageal reflux disease, GERD, heartburn, acid reflux, reflux esophagitis, indigestion, non-ulcer dyspepsia, functional dyspepsia, dyspepsia caused by structural or biochemical disease, biliary tract disease, gastroparesis, pancreatitis, carbohydrate malabsorption, including but not limited to lactose, sorbitol, fructose, and mannitol malabsorption, infiltrative diseases of the stomach, Crohn's disease, sarcoidosis, ischemic bowel disease, inflammatory bowel disease, diverticulitis, *Helicobacter* infections, *Helicobacter pylori* infections, intestinal parasites including but not limited to *giardia* species and *strongyloides* species, abdominal cancer, gastric cancer, esophageal cancer, pancreatic cancer, adenocarcinoma of the antrum and adenocarcinoma of the body of the stomach.

In one embodiment, the present invention provides a process for preparing a compound of formula 3 wherein $R_{11}$, and $R_{14}$ are independently selected from the group consisting of hydrogen and deuterium; $R_{12}$ and $R_{13}$ are independently selected from the group consisting of —CH$_3$, —CDH$_2$, —CD$_2$H, and —CD$_3$. Such a process can be performed, for example, by contacting compound of formula 2 with deuterium oxide under conditions suitable to form a compound of formula 3, as set forth below:

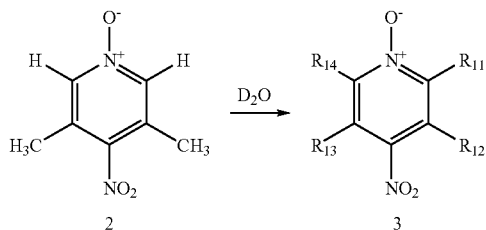

Compound of formula 2 may be prepared by known processes. Compound 2 is typically contacted with deuterium oxide in the presence of a catalyst. Catalysts contemplated for use in the practice of this particular invention process are typically sodium carbonate, potassium carbonate, DBU and the like. Solvents contemplated for use in the practice of this particular invention process are typically polar solvents, such as for example, 1,4-dioxane, acetone, acetonitrile, dimethyl formamide, dimethyl acetamide, N-methylpyrrolidine, dimethyl sulfoxide and the like, or any suitable mixtures thereof. The process is typically carried out at a temperature in the range of about 0° C. up to about 500° C., for 0.01 to 240 hours, at a pH in the range of about 1 up to about 14, at a pressure in the range of about 1 mBar up to about 350 Bar.

In certain embodiments, Compound 2 is typically contacted with deuterium oxide in the presence of a catalyst, with or without another solvent. Catalysts contemplated for use in the practice of this particular invention process are typically sodium carbonate, potassium carbonate, DBU and the like. Solvents contemplated for use in the practice of this particular invention process are typically polar solvents, such as for example, 1,4-dioxane, acetone, acetonitrile, dimethyl formamide, dimethyl acetamide, N-methylpyrrolidine, dimethyl sulfoxide and the like, or any suitable mixtures thereof. The process is typically carried out in the presence of focused microwave radiation using a quartz reactor at a pressure in the range of about 1 Bar to about 25 Bar, a power setting in the range of about 1 W per liter of solvent to about 900 W per liter of solvent, at a temperature in the range of about 0° C. up to about 500° C., for 0.01 to 5 hours, at a pH in the range of about 1 up to about 14.

In another embodiment, the present invention provides a process for preparing a compound of formula 5 wherein $R_{14}$ is hydrogen or deuterium, $R_{12}$, $R_{13}$ and $R_{15}$ are independently selected from the group consisting of —$CH_3$, —$CDH_2$, —$CD_2H$, and —$CD_3$. Such a process can be performed, for example, by contacting compound of formula 4 with deuterium oxide under conditions suitable to form a compound of formula 5, as set forth below:

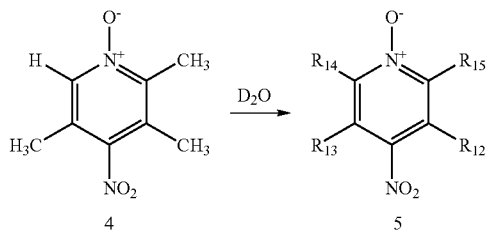

Compound of formula 4 may be prepared by known processes. Compound 4 is typically contacted with deuterium oxide in the presence of a catalyst. Catalysts contemplated for use in the practice of this particular invention process are typically sodium carbonate, potassium carbonate, DBU and the like. Solvents contemplated for use in the practice of this particular invention process are typically polar solvents, such as for example, 1,4-dioxane, acetone, acetonitrile, dimethyl formamide, dimethyl acetamide, N-methylpyrrolidine, dimethyl sulfoxide and the like, or any suitable mixtures thereof. The process is typically carried out at a temperature in the range of about 0° C. up to about 500° C., for 0.01 to 240 hours, at a pH in the range of about 1 up to about 14, and at a pressure in the range of about 1 mBar up to about 350 Bar.

In certain embodiments, Compound 4 is typically contacted with Deuterium oxide in the presence of a catalyst, with or without another solvent. Catalysts contemplated for use in the practice of this particular invention process are typically Sodium carbonate, Potassium carbonate, DBU and the like. Solvents contemplated for use in the practice of this particular invention process are typically polar solvents, such as for example, 1,4-dioxane, acetone, acetonitrile, dimethyl formamide, dimethyl acetamide, N-methylpyrrolidine, dimethyl sulfoxide and the like, or any suitable mixtures thereof. The process is typically carried out in the presence of focused microwave radiation using a quartz reactor at a pressure in the range of about 1 Bar to about 25 Bar, a power setting in the range of about 1 W per liter of solvent to about 900 W per liter of solvent, at a temperature in the range of about 0° C. up to about 500° C., for 0.01 to 5 hours, at a pH in the range of about 1 up to about 14.

Before the present compounds, compositions and methods are disclosed and described, it is to be understood that aspects of the present invention are not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It is also noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds; reference to "a pharmaceutical carrier" includes mixtures of two or more such carriers, and the like.

Certain pharmaceutically acceptable salts of the invention are prepared by treating the novel compounds of the invention with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, Aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water or $D_2O$, alone or in combination with an inert, water-miscible organic solvent, at a temperature of from about 0° C. to about 100° C., preferably at room temperature. The molar ratio of compounds of structural Formula 1 to base used is chosen to provide the ratio desired for any particular salts. For preparing, for example, the ammonium salts of the starting material, compounds of Formula 1 can be treated with approximately one equivalent of the pharmaceutically acceptable base to yield a neutral salt.

When Calcium salts are prepared, approximately one-half a molar equivalent of base is used to yield a neutral salt, while for Aluminum salts, approximately one-third a molar equivalent of base will be used.

The compounds of the invention may be conveniently formulated into pharmaceutical compositions composed of one or more of the compounds together with a pharmaceutically acceptable carrier as described in Remington's Pharmaceutical Sciences, latest edition, by E. W. Martin (Mack Publ. Co., Easton Pa.).

The compounds of the invention may be administered orally, parenterally (e.g., intravenously), by intramuscular injection, by intraperitoneal injection, topically, transdermally, or the like, although oral or topical administration is typically preferred. The amount of active compound administered will, of course, be dependent on the subject being treated, the subject's weight, the manner of administration and the judgment of the prescribing physician. The dosage will be in the range of about 1 microgram per kilogram per day to 100 milligram per kilogram per day.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels and the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents and the like.

For solid compositions, conventional non-toxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable-compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Wherever required, flavoring, preserving, suspending, thickening, or emulsifying agents may also be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, as emulsions, or as sustained release delivery system.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one aspect, the transdermal delivery agent can be DMSO. Transdermal delivery systems can include, such as for example, patches.

Pharmaceutical compositions containing the compounds of the invention as an active ingredient can take the form of tablets, capsules, powders, suspensions, solutions, emulsions as well as salves and creams, and can be used for parenteral (intravenous, intradermal, intramuscular, intrathecal etc.) injections, infiltration, topical application, central injection at spinal cord, oral, rectal, intravaginal and intranasal administering or for local application. Such compositions can be prepared by combining the active ingredient(s) with pharmaceutically acceptable excipients normally used for this purpose. Such excipients can comprise aqueous and non-aqueous solvents, stabilizers, suspension agents, dispersing agents, moisturizers and the like, and will be known to the skilled person in the pharmaceutical field. The composition may further contain likewise suitable additives such as for instance polyethylene glycols and, if necessary, colorants, fragrances and the like.

The pharmaceutical compositions will preferably contain at least 0.1 volume % by weight of the active ingredient. The actual concentration will depend on the human subject and the chosen administering route. In general this concentration will lie between 0.1 and 100% for the above applications and indications. The dose of the active ingredient to be administered can further vary between 1 microgram and 100 milligram per kilogram body weight per day, preferably between 1 microgram and 50 milligram per kilogram body weight per day, and most preferably between 1 microgram and 20 milligram per kilogram body weight per day. Also, all of the specific dosages which lie between the upper and lower dosages stated above are contemplated in the present invention.

The desired dose is preferably presented in the form of one, two, three, four, five, six or more sub-doses that are administered at appropriate intervals per day. The dose or sub-doses can be administered in the form of dosage units containing for instance from 0.5 to 1500 milligram, preferably from 1 to 100 milligram and most preferably from 1 to 40 milligram active constituent per dosage unit, and if the condition of the patient requires the dose can, by way of alternative, be administered as a continuous infusion.

EXAMPLES

As used herein, and unless otherwise indicated, the following abbreviations have the following meanings: Me refers to methyl ($CH_3$—), Et refers to ethyl ($CH_3CH_2$—), i-Pr refers to isopropyl (($CH_3$)$_2CH_2$—), t-Bu or tert-butyl refers to tertiary butyl (($CH_3$)$_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to tert-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), $D_2O$ refers to deuterium oxide, DMF refers to N,N-dimethylformamide, DCM refers to dichloromethane ($CH_2Cl_2$), THF refers to tetrahydrofuran, EtOAc refers to ethyl acetate, Et$_2$O refers to diethyl ether, MeCN refers to acetonitrile (CH$_3$CN), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCI refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4-diyl diether, (DHQD)$_2$PHAL refers to dihydroquinidine phthalazine-1,4-diyl diether, (DHQD)$_2$PYR refers to dihydroquinidine 2,5-diphenyl-4,6-pyrimidinediyl diether, LDA refers to lithium diisopropylamide, LiTMP refers to Lithium 2,2,6,6-tetramethylpiperdinamide, n-BuLi refers to n-butyl-Lithium, t-BuLi refers to tert-butyl lithium, IBA refers to 1-hydroxy-1,2-benziodoxol-3(1H)-one 1-oxide, OsO$_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to Sodium hexamethyldisilazide, LiHMDS refers to Lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, Ac$_2$O refers to acetic anhydride, AcCl refers to acetyl chloride, TsOH refers to p-toluenesulfonic acid, TsCl refers to p-toluenesulfonyl chloride, MBHA refers to 4-methylbenzhydrylamine, BHA refers to benzhydrylamine, ZnCl$_2$ refers to zinc (II) dichloride, BF$_3$ refers to boron trifluoride, Y(OTf)$_2$ refers to yttrium (III) trifluoromethanesulfonate, Cu(BF$_4$)$_2$ refers to copper (II) tetrafluoroborate, LAH refers to lithium aluminum hydride (LiAlH$_4$), LAD refers to lithium aluminum deuteride, NaHCO$_3$ refers to Sodium bicarbonate, K$_2$CO$_3$ refers to Potassium carbonate, NaOH refers to sodium hydroxide, KOH refers to potassium hydroxide, LiOH refers to lithium hydroxide, HCl refers to hydrochloric acid, H$_2$SO$_4$ refers to sulfuric acid, MgSO$_4$ refers to magnesium sulfate, and Na$_2$SO$_4$ refers to sodium sulfate. $^1$H NMR refers to proton nuclear magnetic resonance, $^{13}$C NMR refers to carbon-13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, R$_f$ refers to retention factor, R$_t$ refers to retention time, GC refers to gas chromatography, min is minutes, h is hours, rt or RT is room or ambient temperature, g is grams, mg is milligrams, kg is kilograms, L is liters, mL is milliliters, mol is moles and mmol is millimoles.

For all of the following examples, standard work-up and purification methods can be utilized and will be obvious to those skilled in the art. Synthetic methodologies that make up the invention are shown in Scheme 1. This Scheme is intended to describe the applicable chemistry through the use of specific examples and is not indicative of the scope of the invention.

SCHEME 1

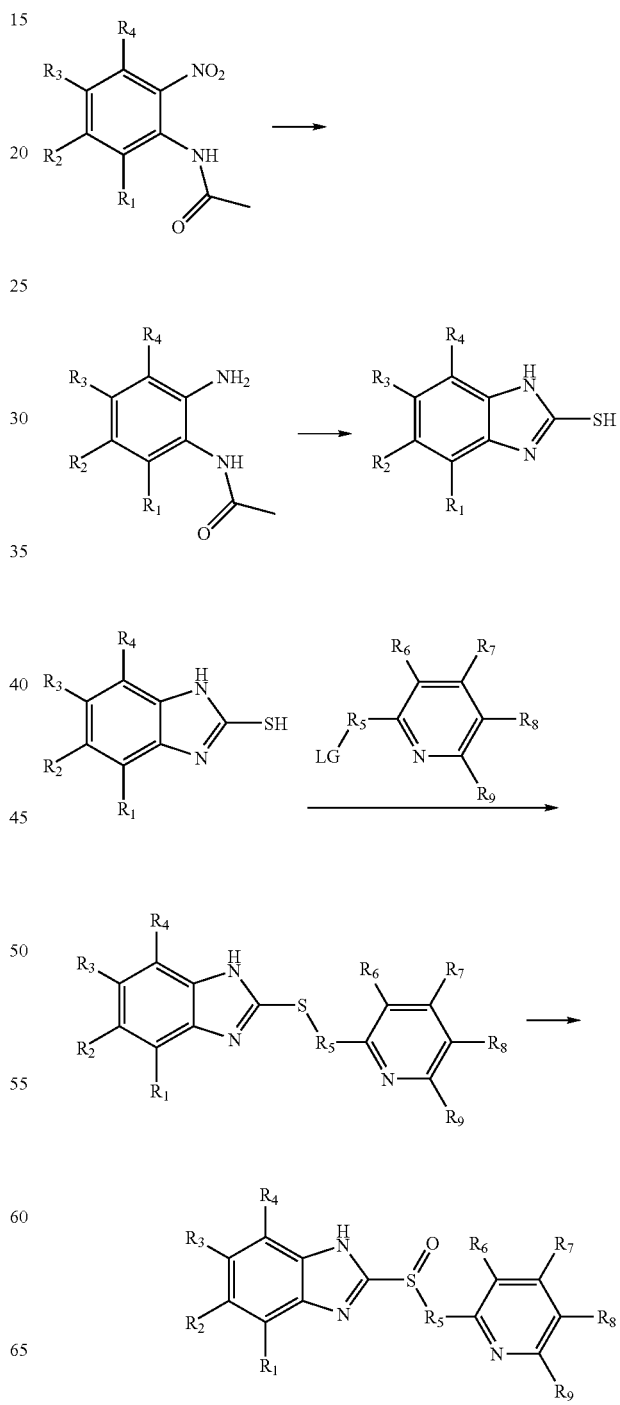

The following non-limiting examples illustrate the inventors' preferred methods for carrying out the process of the invention.

Example 1

$d_3$-4-methoxy acetanilide

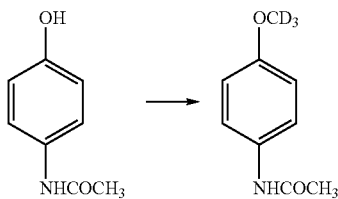

To a suspension of acetaminophen (2 g, 13.25 mmol) in water (30 mL) was added NaOH (1.06 g, 26.6 mmol) was added at ambient temperature. Upon dissolution, $d_6$-dimethyl sulfate (3.5 g, 26.5 mmol) was added and the reaction mixture was stirred for 6 h. The precipitate was filtered, washed with water and dried to give the product as a white crystalline solid. $^1$H-NMR analysis of this material showed greater than 98% deuterium incorporation.

Yield: 1.88 g (84%). $^1$H-NMR (CDCl$_3$) δ ppm: 2.18 (s, 3H); 6.84 (d, 2H); 7.2 (br s, 1H); 7.4 (d, 2H).

Example 2

$d_3$-2-nitro-4-methoxy acetanilide

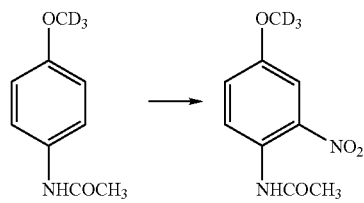

To a suspension of $d_3$-4-methoxy acetanilide (1.88 g, 11.2 mmol) in water (8 mL) and acetic acid (7 mL) was added 70% nitric acid (1.2 mL) dropwise at ambient temperature, and the reaction mixture was stirred for 6 h, and the yellow precipitate was filtered, washed with water and dried. $^1$H-NMR analysis of this material showed greater than 98% deuterium incorporation.

Yield: 1.43 g (60%). $^1$H-NMR (CDCl$_3$) δ ppm: 2.26 (s, 3H); 7.2 (d, 1H); 7.64 (s, 1H); 8.6 (d, 1H); 10.2 (br s, 1H).

Example 3

$d_3$-2-amino-4-methoxy acetanilide

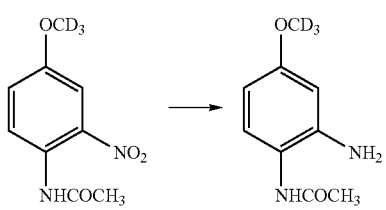

To a solution of $d_3$-2-nitro-4-methoxy acetanilide (1.46 g, 6.85 mmol) in ethanol (36 mL) was added 10% palladium carbon (300 mg, 0.28 mmol) and hydrazine hydrate (0.6 mL, 12.4 mmol) dropwise, at ambient temperature. The mixture was stirred until completion, the catalyst was filtered and the solvent was removed to give the product as a white solid. $^1$H-NMR analysis of this material showed greater than 98% deuterium incorporation.

Yield: 785 mg. (63%). $^1$H-NMR (CDCl$_3$) δ ppm: 2.2 (s, 3H); 6.34 (m, 2H), 7.0 (m, 2H).

Example 4

$d_3$-2-mercapto-5-methoxy benzimidazole

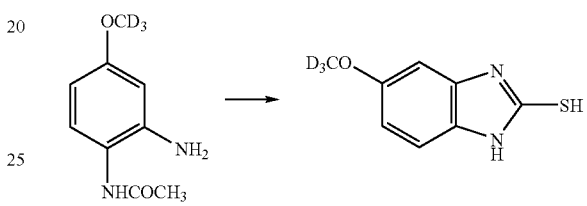

A suspension of $d_3$-2-amino-4-methoxy acetanilide (785 mg, 4.29 mmol) and EtOCS$_2$K (844 mg, 5.28 mmol) in EtOH (7 ml) and water (2 ml) was heated to 95° C. for 5 hr. The solution was cooled to ambient temperature and allowed to stand for 15 hr. The crystalline product is filtered, washed with water and dried. $^1$H-NMR analysis of this material showed greater than 98% deuterium incorporation.

Yield: 488 mg (62%). $^1$H-NMR (CDCl$_3$-CD$_3$OD) δ ppm: 2.4 (s, 1H); 6.7 (m, 2H); 7.2 (d, 1H).

Example 5

2,3,5-trimethylpyridine-1-oxide

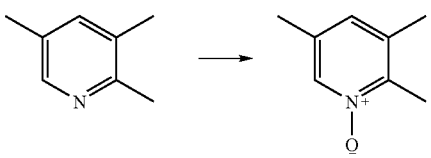

To a stirred mixture of 2,3,5-collidine (10 g, 82.5 mmol) and glacial acetic acid (40 mL) was added hydrogen peroxide (30% solution, 20 mL, dropwise) at 65° C. The bath was heated to 90° C. for 1 hour, cooled to 65° C. and additional hydrogen peroxide (30% solution, 10 mL, dropwise) was added. The reaction mixture was heated at 90° C. until completion and cooled to ambient temperature. The solvent was removed under reduced pressure and the crude residue was used directly in the next step.

$^1$H-NMR (CDCl$_3$) δ ppm: 2.24 (s, 3H); 2.26 (s, 3H); 2.5 (s, 3H); 7.06 (s, 1H); 8.2 (s, 1H).

Example 6

2,3,5-trimethyl-4-nitropyridine-1-oxide

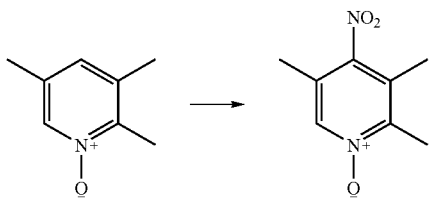

The crude residue from example 5 was placed in an ice bath and dissolved in conc. $H_2SO_4$ (14 mL). The solution was placed in a 90° C. bath and a mixture of 25 mL conc. $H_2SO_4$ and 28 mL conc. nitric acid was added dropwise over one hour, and the reaction was kept at 90° C. until completion. The solution was cooled to ambient temperature and poured onto crushed ice (~200 g). Solid NaOH (55 g) was added and the mixture was extracted with Ethyl acetate (200×3 mL); the combined organic layers were washed with water (100 mL), brine (50 mL) and dried over anhydrous $Na_2SO_4$. The solvent was removed and the yellow residue was purified by column chromatography (5% $CH_3OH$—$CH_2Cl_2$) to give the product as a yellow light sensitive solid.

Yield: 9.0 g (84%). $^1$H-NMR (CDCl$_3$) δ ppm: 2.22 (s, 3H); 2.24 (s, 3H); 2.5 (s, 3H); 8.08 (s, 1H).

Example 7

$d_{10}$-2,3,5-Trimethyl-4-nitropyridine-1-oxide

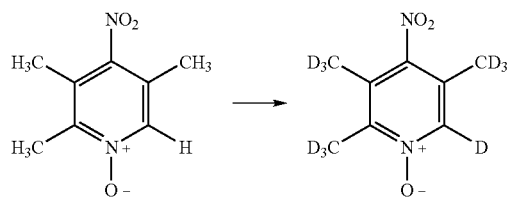

A dry heavy-walled teflon screw cap glass tube equipped with a magnetic stirrer was charged with 2,3,5-trimethyl-4-nitropyridine-1-oxide (5 g, 27.5 mmol), $K_2CO_3$ (3.8 g, 27.5 mmol) and $D_2O$ (30 mL) under nitrogen. The apparatus was sealed and the mixture was placed in an oil bath at 150° C. for 2 hours. The reaction was cooled to ambient temperature, NaCl (10 g) and brine (50 mL) were added and the mixture was extracted with ethyl acetate (5×50 mL). The organic layer was dried over $Na_2SO_4$. The solvent was removed to yield 4.2 g of a yellow solid with identical TLC behavior as the starting material ($R_f$=0.3 in 10% methanol-DCM). The above process was repeated a second time to yield 3.25 g of the product. GC-MS analysis of this material showed 98.1% deuterium incorporation.

Yield: 65%. GC-MS: [M]$^+$: 192 (81.6%, 2,3,5-trimethyl-4-nitropyridine-1-oxide-$d_{10}$), 191 (18.3%, 2,3,5-trimethyl-4-nitropyridine-1-oxide-$d_9$)

Example 8

$d_{12}$-5-methoxy-2-(4-nitro-3,5-dimethylpyridin-2-ylmethylsulfanyl)-1H-benzimidazole

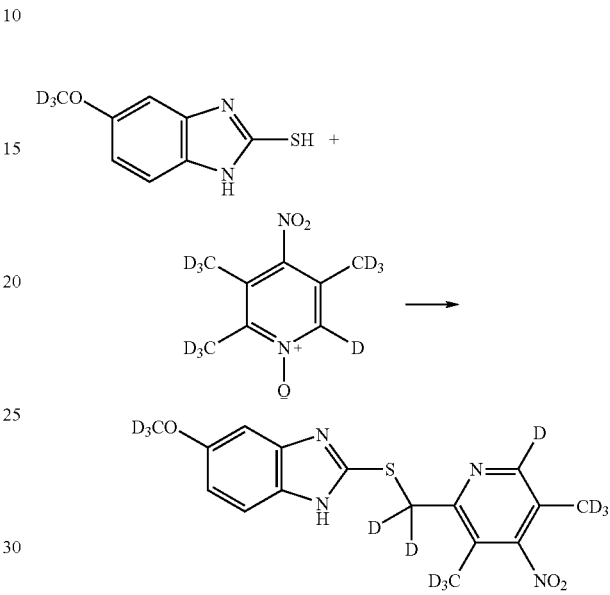

A solution of $d_{10}$-2,3,5-trimethyl-4-nitropyridine-1-oxide (384 mg, 2 mmol) and methanesulfonic anhydride (696 mg, 4 mmol) in 1,2-dichloroethane (4 ml) was heated to 95° C. for 6 hours in dry heavy-walled teflon screw cap glass tube. The reaction was cooled to 4° C. and a suspension of $d_3$-2-mercapto-5-methoxy benzimidazole (328 mg, 1.79 mmol), ethyldiisopropylamine (1.6 ml, 4.8 mmol), dimethylaminopyridine (50 mg, 0.4 mmol) in dichloromethane (4 ml) was added. The mixture was stirred for 30 hours at ambient temperature, filtered through a short pad of silica gel (10% methanol-dichloromethane). The solvent was removed and the crude residue was recrystallized from methanol-water to give the product as a yellow solid.

Yield: 412 mg (64%). $^1$H-NMR ($d_6$-acetone) δ ppm: 6.8 (d, 1H); 7.02 (s, 1H); 7.4 (d, 1H).

Example 9

$d_{15}$-5-methoxy-2-(4-methoxy-3,5-dimethylpyridin-2-ylmethylsulfanyl)-1H-benzimidazole

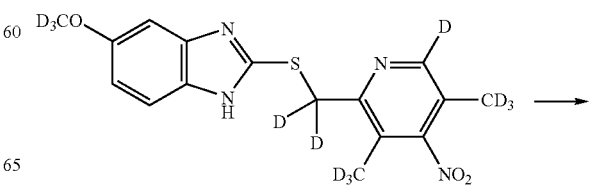

-continued

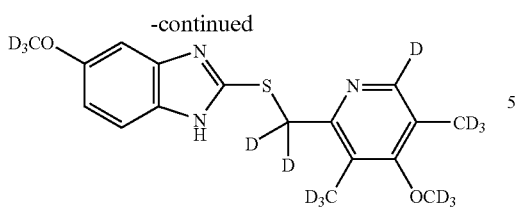

$d_{12}$-5-methoxy-2-(4-nitro-3,5-dimethylpyridin-2-ylmethylsulfanyl)-1H-benzimidazole (300 mg, 0.84 mmol) and benzyltriethylammonium chloride (20 mg, 0.1 mmol) were taken up in 4 ml of $d_4$-methanol and treated with a 4.78 M solution of $NaOCD_3$ in $d_4$-methanol (1.76 ml, 8.4 mmol) at ambient temperature. The solution was heated to reflux for 24 hours, cooled to ambient temperature, diluted with dichloromethane, washed with brine, dried over magnesium sulfate. The solvent was removed under reduced pressure to yield the crude product which was used directly in the next step.

Yield: 282 mg (98%). $^1$H-NMR ($d_6$-acetone) δ ppm: 6.79 (m, 1H); 7.05 (m, 1H); 7.4 (m, 1H).

Example 10

$d_{15}$-5-methoxy-2-(4-methoxy-3,5-dimethyl-pyridin-2-ylmethane-sulfinyl)-1H-benzimidazole ($d_{15}$-omeprazole)

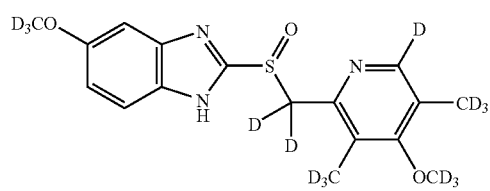

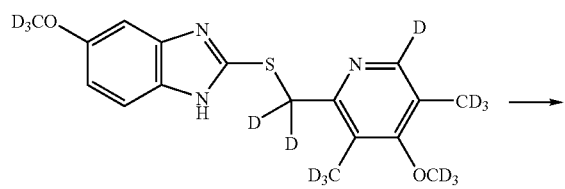

$d_{12}$-5-methoxy-2-(4-methoxy-3,5-dimethylpyridin-2-ylmethylsulfanyl)-1H-benzimidazole (30 mg, 0.087 mmol) was dissolved in 1.5 ml of chloroform, cooled to −40° C. and treated dropwise with a solution of meta-chloroperbenzoic acid (15 mg, 1 equiv) in 0.5 ml of chloroform. The reaction was maintained at that temperature for 30 minutes, poured into saturated sodium bicarbonate and extracted with ethyl acetate. The organic layer was dried over sodium sulfate, the solvent was removed and the crude residue was purified by silica gel chromatography to yield the product ($d_{15}$-omeprazole) as a white solid.

Yield: 10 mg (32%). $^1$H-NMR ($d_6$-acetone) δ ppm: 6.95 (m, 1H); 7.18 (m, 1H); 7.58 (m, 1H).

Example 11

$d_{13}$-5-methoxy-2-(4-methoxy-3,5-dimethylpyridin-2-ylmethane-sulfinyl)-1H-benzimidazole ($d_{13}$-omeprazole)

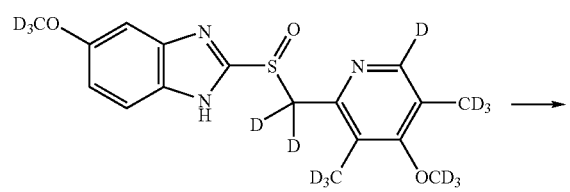

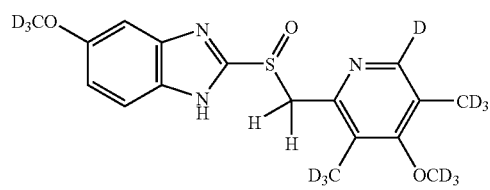

$d_{15}$-Omeprazole (5 mg, 0.014 mmol) was taken up in 0.5 ml of methanol and added dropwise to a 0.1M solution of sodium carbonate in $H_2O$ (pH=11.4) at ambient temperature; the solution was stirred for 4 days, diluted with dichloromethane, washed with brine and dried over anhydrous magnesium sulfate. The solvent was removed under reduced pressure to yield the product as a white solid.

Yield: 4 mg (80%). $^1$H-NMR ($d_6$-acetone) δ ppm: 4.7 (s, 2H), 6.95 (d, 1H); 7.18 (d, 1H); 7.58 (d, 1H).

Example 12

$d_{10}$-5-methoxy-2-(4-methoxy-3,5-dimethylpyridin-2-ylmethylsulfanyl)-1H-benzimidazole

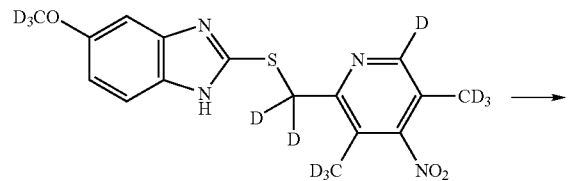

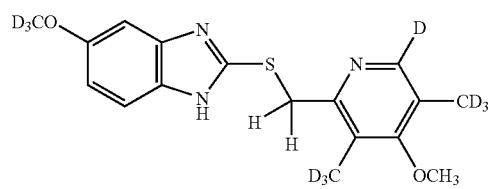

Prepared according to example 9, by substituting CD₃ONa—CD₃OH with CH₃ONa—CH₃OH.

Example 13 d₁₀-5-methoxy-2-(4-methoxy-3,5-dimethylpyridin-2-ylmethane-sulfinyl)-1H-benzimidazole (d₁₀-omeprazole)

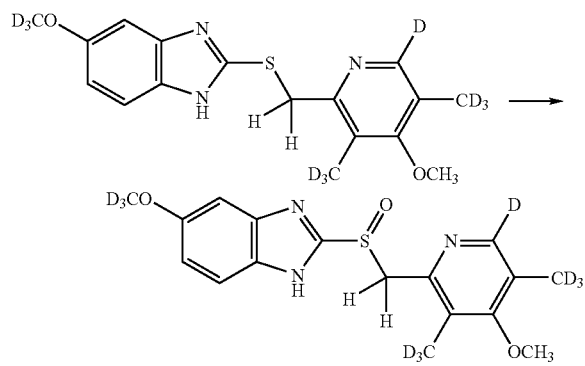

Prepared according to example 10.

Example 14 d₁₂-5-methoxy-2-(4-methoxy-3,5-dimethylpyridin-2-ylmethane-sulfinyl)-1H-benzimidazole (d₁₂-omeprazole)

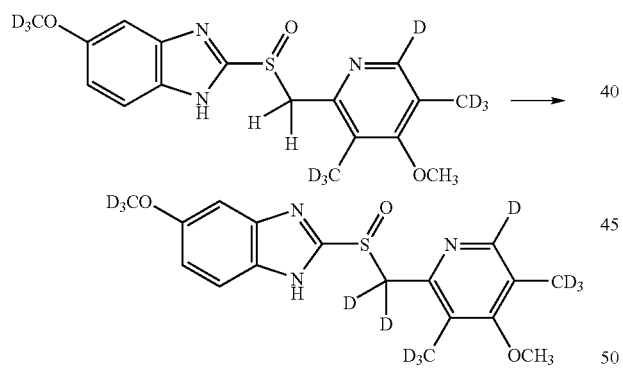

Prepared according to example 11, by substituting D₂O for water and CD₃OD for methanol.

Example 15 d₉-5-methoxy-2-(4-nitro-3,5-dimethylpyridin-2-ylmethylsulfanyl)-1H-benzimidazole

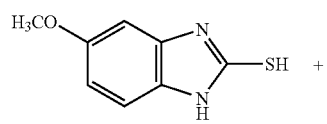

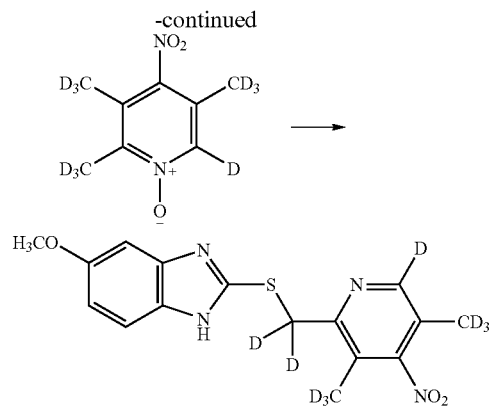

Prepared according to example 8.

Example 16 d₁₂-5-methoxy-2-(4-methoxy-3,5-dimethylpyridin-2-ylmethylsulfanyl)-1H-benzimidazole

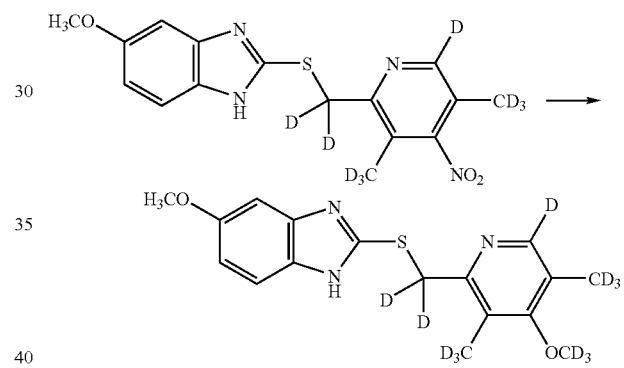

Prepared according to example 9.

Example 17 d₇-5-methoxy-2-(4-methoxy-3,5-dimethylpyridin-2-ylmethylsulfanyl)-1H-benzimidazole

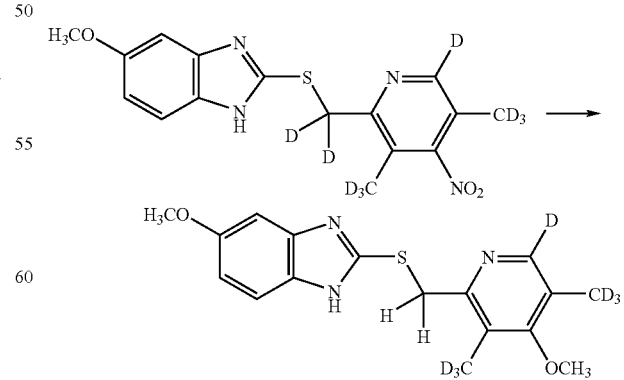

Prepared according to example 9, by substituting CD₃ONa—CD₃OH with CH₃ONa—CH₃OH.

Example 18 d$_{12}$-5-methoxy-2-(4-methoxy-3,5-dimethylpyridin-2-ylmethane-sulfinyl)-1H-benzimidazole (d$_{12}$-omeprazole)

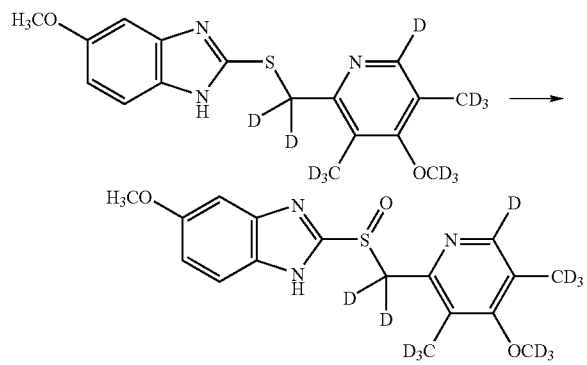

Prepared according to example 10.

Example 19 d$_7$-5-methoxy-2-(4-methoxy-3,5-dimethylpyridin-2-ylmethane-sulfinyl)-1H-benzimidazole (d$_7$-omeprazole)

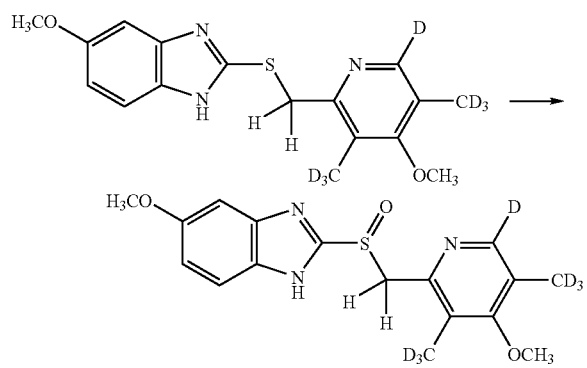

Prepared according to example 10.

Example 20 d$_{10}$-5-methoxy-2-(4-methoxy-3,5-dimethylpyridin-2-ylmethane-sulfinyl)-1H-benzimidazole (d$_{10}$-omeprazole)

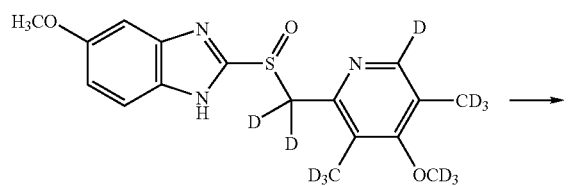

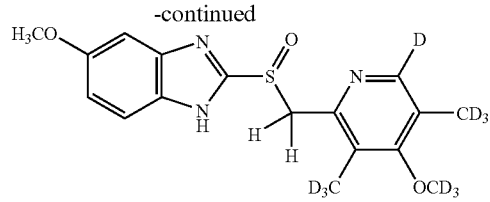

Prepared according to example 11.

Example 21 d$_9$-5-methoxy-2-(4-methoxy-3,5-dimethylpyridin-2-ylmethane-sulfinyl)-1H-benzimidazole (d$_9$-omeprazole)

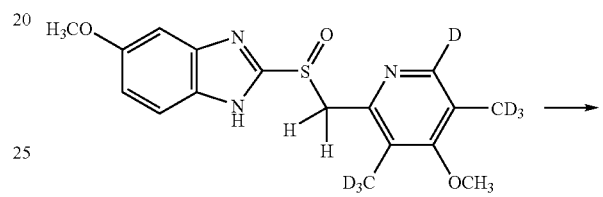

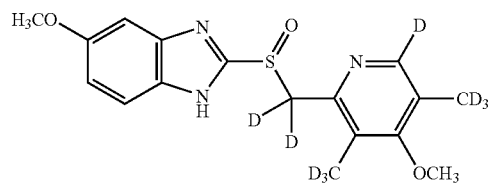

Prepared according to example 11, by substituting D$_2$O for water and CD$_3$OD for methanol.

Example 22 d$_3$-5-methoxy-2-(4-nitro-3,5-dimethylpyridin-2-ylmethylsulfanyl)-1H-benzimidazole

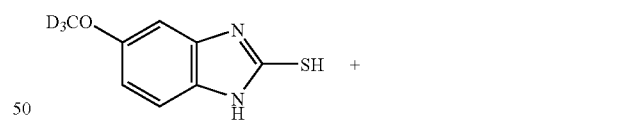

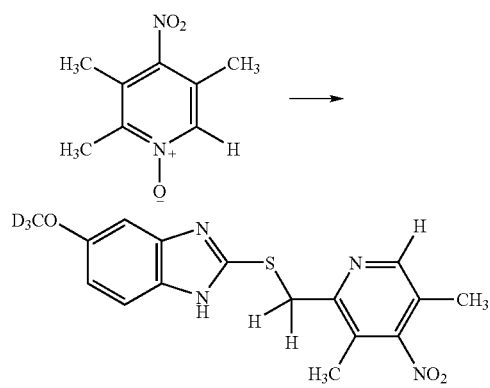

Prepared according to example 8.

Example 23 d₈-5-methoxy-2-(4-methoxy-3,5-dimethylpyridin-2-ylmethylsulfanyl)-1H-benzimidazole

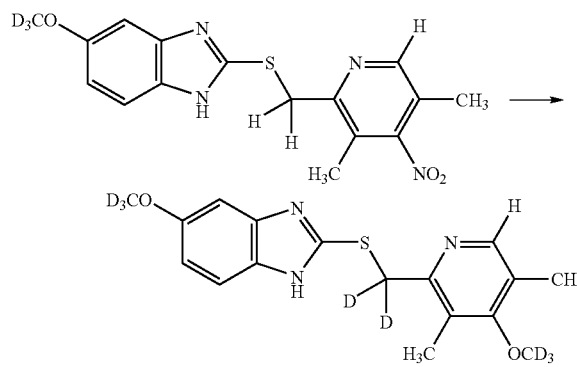

Prepared according to example 9.

Example 24 d₃-5-methoxy-2-(4-methoxy-3,5-dimethylpyridin-2-ylmethylsulfanyl)-1H-benzimidazole

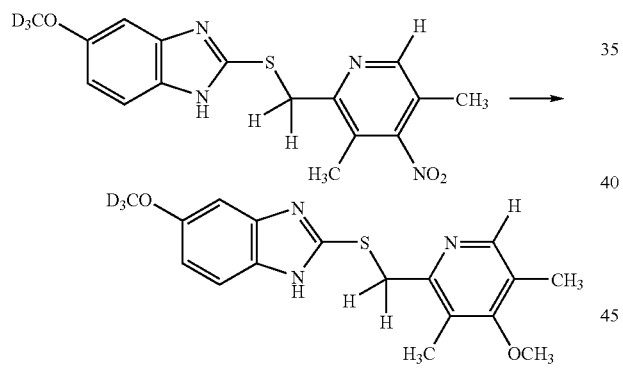

Prepared according to example 9, by substituting CD₃ONa—CD₃OH with CH₃ONa—CH₃OH.

Example 25 d₈-5-methoxy-2-(4-methoxy-3,5-dimethylpyridin-2-ylmethane-sulfinyl)-1H-benzimidazole (d₈-omeprazole)

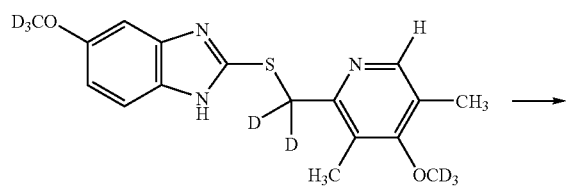

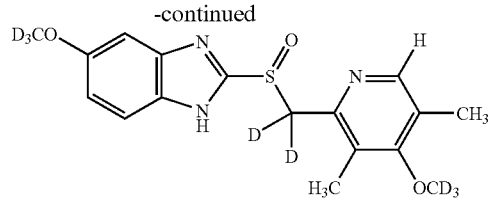

Prepared according to example 10.

Example 26 d₃-5-methoxy-2-(4-methoxy-3,5-dimethylpyridin-2-ylmethane-sulfinyl)-1H-benzimidazole (d₃-omeprazole)

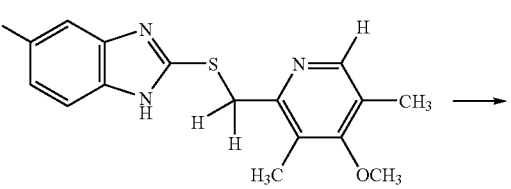

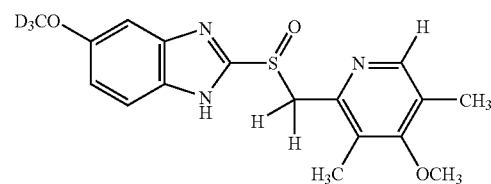

Prepared according to example 10.

Example 27 d₆-5-methoxy-2-(4-methoxy-3,5-dimethylpyridin-2-ylmethane-sulfinyl)-1H-benzimidazole (d₆-omeprazole)

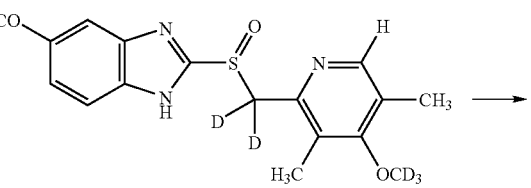

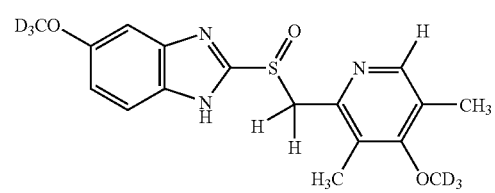

77

Prepared according to example 11.

Example 28

$d_5$-5-methoxy-2-(4-methoxy-3,5-dimethylpyridin-2-ylmethane-sulfinyl)-1H-benzimidazole ($d_5$-omeprazole)

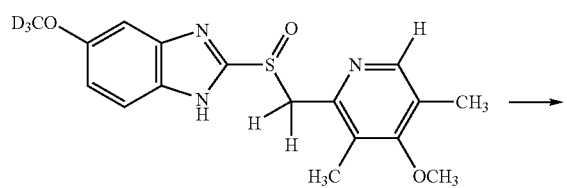

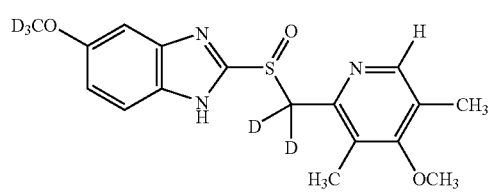

Prepared according to example 11, by substituting $D_2O$ for water and $CD_3OD$ for methanol.

Example 29

5-methoxy-2-(4-nitro-3,5-dimethylpyridin-2-ylmethylsulfanyl)-1H-benzimidazole

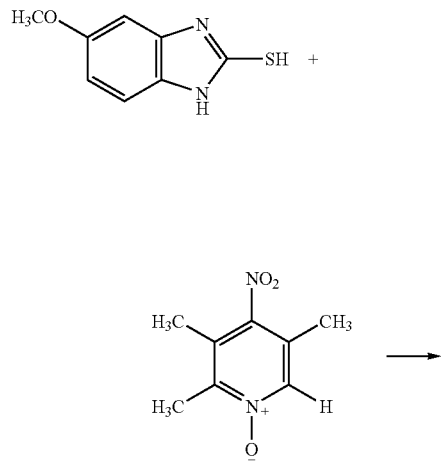

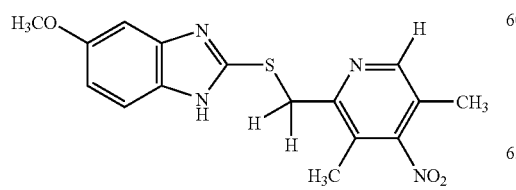

78

Prepared according to example 8.

Example 30

$d_5$-5-methoxy-2-(4-methoxy-3,5-dimethylpyridin-2-ylmethylsulfanyl)-1H-benzimidazole

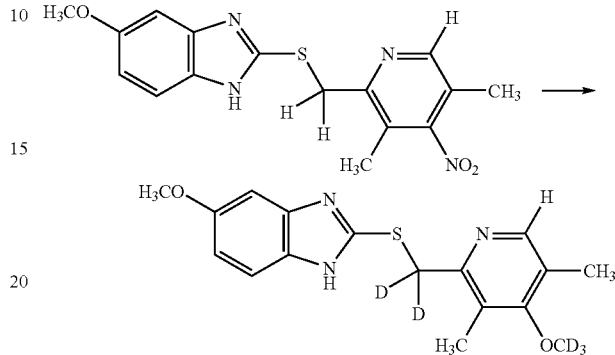

Prepared according to example 9.

Example 31

5-methoxy-2-(4-methoxy-3,5-dimethylpyridin-2-ylmethylsulfanyl)-1H-benzimidazole

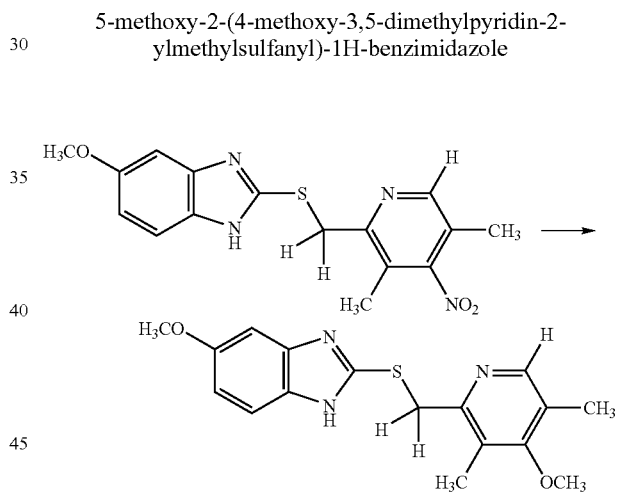

Prepared according to example 9, by substituting $CD_3ONa$—$CD_3OH$ with $CH_3ONa$—$CH_3OH$.

Example 32

$d_5$-5-methoxy-2-(4-methoxy-3,5-dimethylpyridin-2-ylmethane-sulfinyl)-1H-benzimidazole ($d_5$-omeprazole)

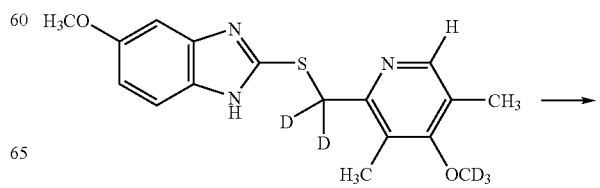

-continued

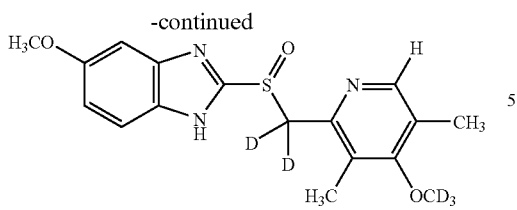

Prepared according to example 10.

Example 33

Omeprazole

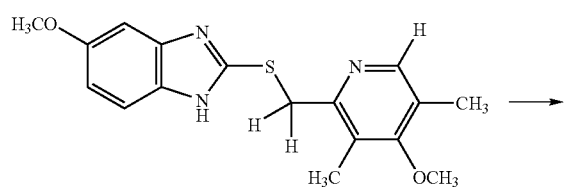

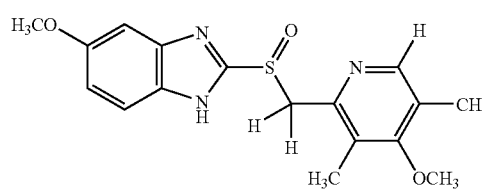

Prepared according to example 10.

Example 34 d$_3$-5-methoxy-2-(4-methoxy-3,5-dimethylpyridin-2-ylmethane-sulfinyl)-1H-benzimidazole (d$_3$-omeprazole)

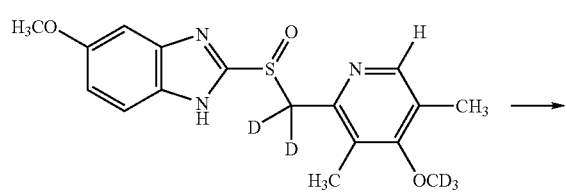

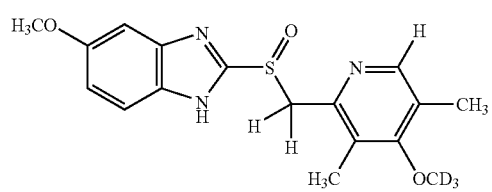

Prepared according to example 11.

Example 35 d$_2$-5-methoxy-2-(4-methoxy-3,5-dimethylpyridin-2-ylmethane-sulfinyl)-1H-benzimidazole (d$_2$-omeprazole)

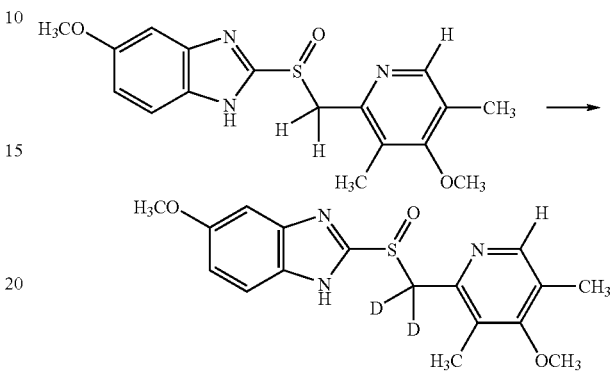

Prepared according to example 11, by substituting D$_2$O for water and CD$_3$OD for methanol.

Example 36

5-methoxy-2-(4-methoxy-3,5-dimethylpyridin-2-ylmethane-sulfinyl)-1H-benzimidazole sodium salt (omeprazole sodium salt)

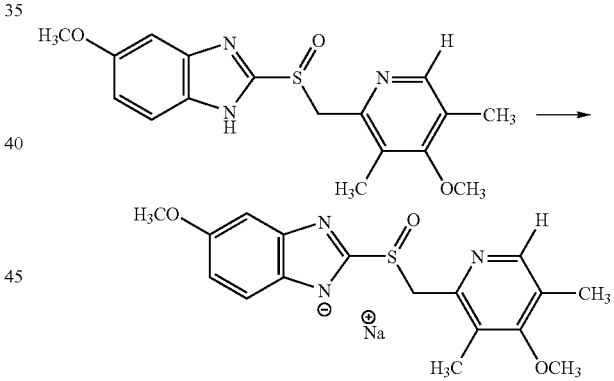

The procedure was carried out as described in Raju et al, *Organic Process Research & Development* 2006, 10, 33-35, which is hereby incorporated by reference in its entirety. Sodium hydroxide (753 mg, 18.8 mmol, 1.14 equiv) was crushed, poured into a mixture of methanol (6 mL) and isopropyl alcohol (54 mL) and stirred vigorously at ambient temperature until homogeneous. The solution was filtered through Celite and the Celite was washed with isopropyl alcohol (7 mL). To the resultant filtrate, omeprazole (5.88 g, 17.1 mmol, 1 equiv) was added at ambient temperature and the mixture was stirred for 1-2 hours. The precipitate was filtered and washed with isopropyl alcohol (6 mL), and cyclohexane (10 mL). The white crystalline salt was stirred for 1-2 hours at ambient temperature in a mixture of cyclohexane (30 mL) and water (0.5 mL), filtered, washed with cyclohexane (15 mL) and dried under reduced pressure to afford 5.73 g of omeprazole sodium salt (88% yield).

Example 37

(S)-5-methoxy-2-(4-methoxy-3,5-dimethylpyridin-2-ylmethane-sulfinyl)-1H-benzimidazole mandalate salt (esomeprazole mandalate salt)

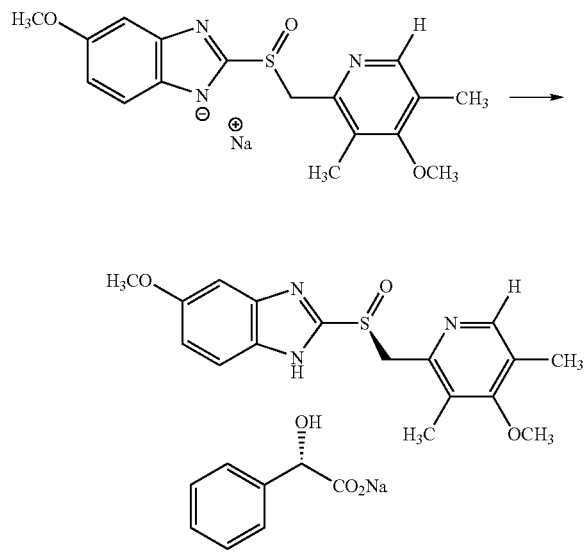

The procedure was carried out as described in Raju et al, *Organic Process Research & Development* 2006, 10, 33-35, which is hereby incorporated by reference in its entirety. To a suspension of omeprazole sodium salt (5.53 g, 15.1 mmol, 1 equiv) in acetone (60 mL), were added a solution of diethyl-D-tartrate (3.1 g, 15.1 mol, 1 equiv) in acetone (3 mL), titanium (IV) isopropoxide (2.14 g, 7.55 mmol, 0.5 equiv) and triethylamine (4.75 g, 45.3 mmol, 3 equiv) at 35-40° C. To the resulting homogeneous solution was added L-(+)-mandelic acid (2.64 g, 17.4 mmol, 1.15 equiv). The mixture was cooled to ambient temperature and stirred for about 1-2 hours. The precipitate was filtered, washed with acetone (30 mL), and dried under reduced pressure to afford esomeprazole mandalate salt.

Example 38

(S)-5-methoxy-2-(4-methoxy-3,5-dimethylpyridin-2-ylmethane-sulfinyl)-1H-benzimidazole (esomeprazole)

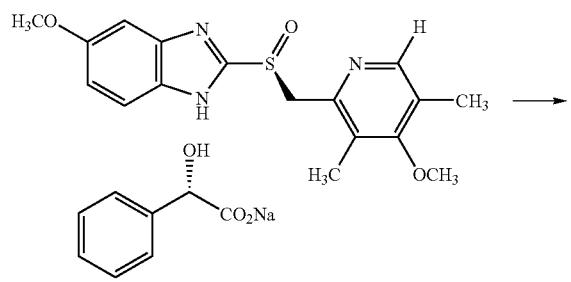

-continued

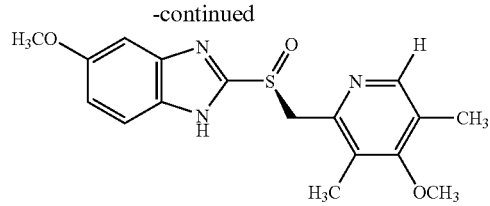

The procedure was carried out as described in Raju et al, *Organic Process Research & Development* 2006, 10, 33-35, which is hereby incorporated by reference in its entirety. Esomeprazole mandalate salt (7.5 g) was suspended in a mixture of dichloromethane (80 mL) and 5% sodium bicarbonate (80 mL) and stirred for 15-30 minutes. The organic phase was separated, and the solvent was removed under reduced pressure to afford 7.3 g of esomperazole.

Example 39

$d_{13}$-(S)-5-methoxy-2-(4-methoxy-3,5-dimethylpyridin-2-ylmethane-sulfinyl)-1H-benzimidazole ($d_{13}$-esomeprazole)

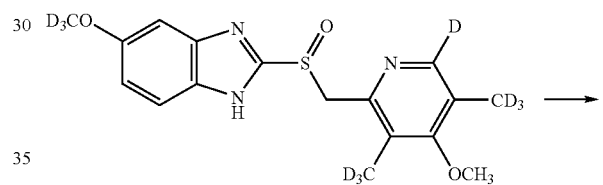

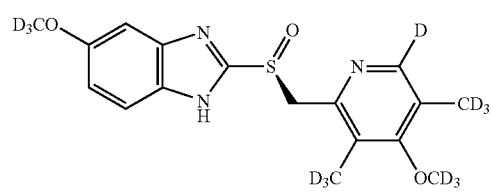

Prepared according to examples 36, 37, and 38.

Example 40

(S)-5-methoxy-2-(4-methoxy-3,5-dimethylpyridin-2-ylmethane-sulfinyl)-1H-benzimidazole Magnesium Salt (esomeprazole magnesium salt)

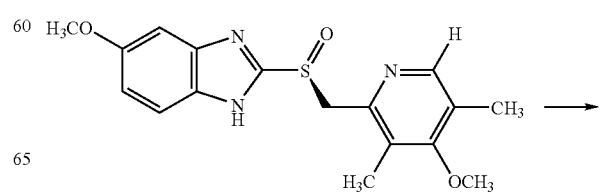

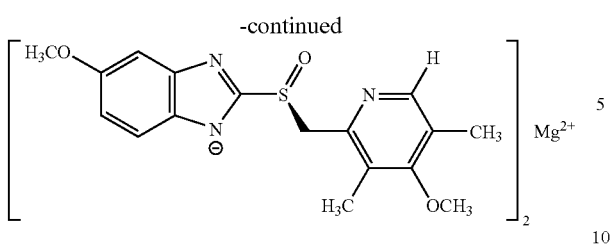

The procedure is carried out as described in Raju et al, Organic Process Research & Development 2006, 10, 33-35, which is hereby incorporated by reference in its entirety. A solution of magnesium methoxide was prepared by adding magnesium turnings (1.31 g, 0.054 mol) and dichloromethane (5 mL) to methanol (150 mL) and stirring under nitrogen atmosphere for 2-3 hours, at 40-45° C. The solution was cooled to 5-10° C. and added to a stirred mixture of esomeprazole (42.0 g, 0.121 mol) and methanol (150.0 mL), and stirring was maintained for 3 hours. Water (2.0 mL) was added and stirring was continued for 1 hour and the solution was filtered. The mother liquor was distilled under reduced pressure at 35° C. Acetone (400 mL) was added and the mixture was stirred for 1 hour at 25-35° C. The precipitate was filtered and washed with acetone (200 mL), dissolved in methanol (222 mL) and water (8 mL) and stirred for about 30 minutes at 25-30° C. and filtered. The filtrate was suspended in water and stirred at 0-5° C. for about 45 minutes, filtered, washed with water (300 mL) and dried under reduced pressure to yield esomeprazole magnesium salt.

Example 41

$d_{13}$-(S)-5-methoxy-2-(4-methoxy-3,5-dimethylpyridin-2-ylmethane-sulfinyl)-1H-benzimidazole Magnesium Salt ($d_{13}$-esomeprazole magnesium salt)

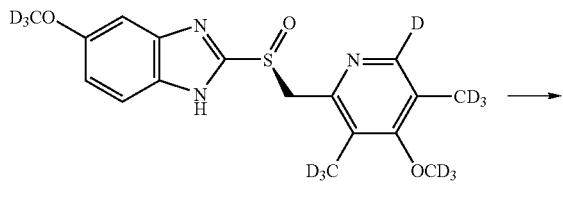

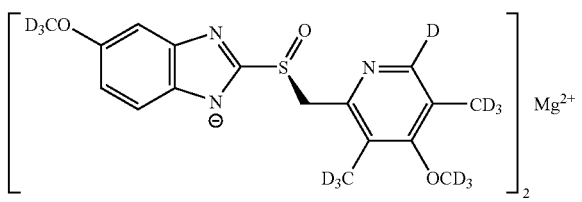

Prepared according to example 40.

Example 42

(R)-5-methoxy-2-(4-methoxy-3,5-dimethylpyridin-2-ylmethane-sulfinyl)-1H-benzimidazole sodium salt ((R)-omeprazole sodium salt)

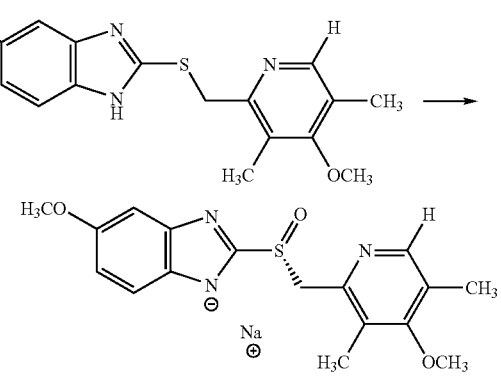

The procedure is carried out as described in Cotton et al, Tetrahedron: Asymmetry 2000, 11(18), 3819-3825, which is hereby incorporated by reference in its entirety. Water (2.4 mmol), (R,R)-diethyl tartrate (11.4 mmol) and titanium tetraisopropoxide (5.6 mmol) were added to a suspension of 5-methoxy-2-(4-methoxy-3,5-dimethyl-pyridin-2-ylmethyl-sulfanyl)-1H-benzoimidazole (18.8 mmol) in toluene (25 mL) at 54° C. The mixture was stirred for 50 minutes at 54° C., cooled to 30° C. and N,N-diisopropylethyl-amine (5.6 mmol) and cumene hydroperoxide (84% in cumene, 18.2 mmol) were added. The mixture was stirred for 1 hour, and extracted three times with aqueous ammonium hydroxide. Methyl isobutyl ketone (9 mL) was added to the combined aqueous extracts, and the pH was adjusted with acetic acid. The organic layer was treated with 50% aqueous sodium hydroxide (13.2 mmol) and acetonitrile (70 mL). The solution was concentrated during which the product gradually precipitated to give (R)-omeprazole sodium as a white solid. $^1$H NMR (DMSO-$d_6$) δ 2.15 (s, 3H), 2.20 (s, 3H), 3.68 (s, 3H), 3.71 (s, 3H), 4.5 (m, 2H), 6.56 (m, 1H), 7.00 (d, 1H), 7.34 (d, 1H), 8.30 (s, 1H).

Example 43

$d_{13}$-(R)-5-methoxy-2-(4-methoxy-3,5-dimethylpyridin-2-ylmethane-sulfinyl)-1H-benzimidazole sodium salt ($d_{13}$-(R)-omeprazole sodium salt)

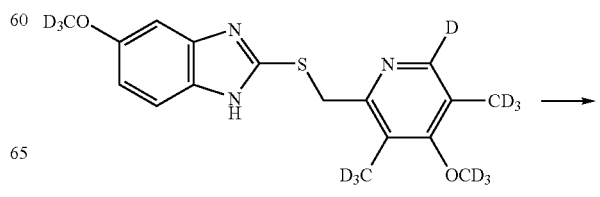

-continued

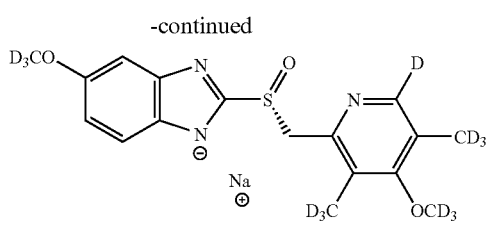

Prepared according to example 42.

Example 44

2-(3-Methyl-4-nitro-pyridin-2-ylmethylsulfanyl)-1H-benzoimidazole

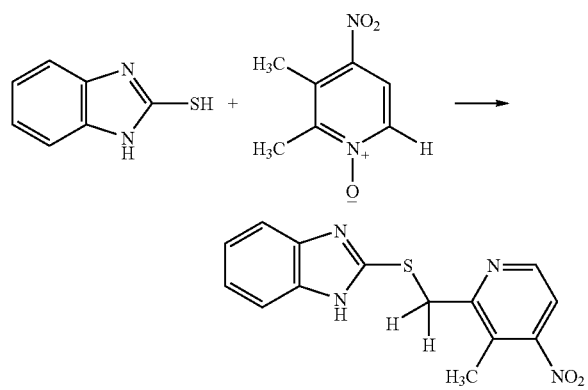

Prepared according to example 8.

Example 45

$d_2$-2-[3-Methyl-4-(2,2,2-trifluoroethoxy)-pyridin-2-ylmethylsulfanyl]-1H-benzoimidazole

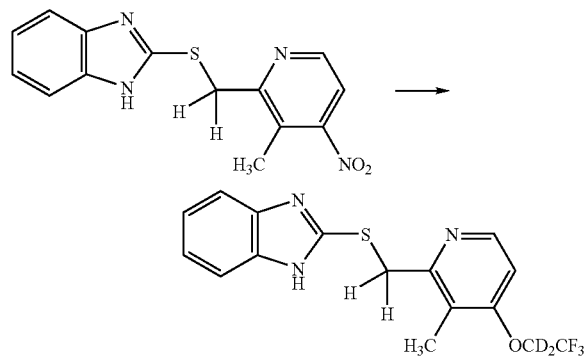

Prepared according to example 9, by substituting $CF_3CD_2ONa$—$CF_3CD_2OH$ (Cambridge Isotope Laboratories) for $CD_3ONa$—$CD_3OD$.

Example 46

$d_2$-2-[3-Methyl-4-(2,2,2-trifluoroethoxy)-pyridin-2-ylmethanesulfinyl]-1H-benzoimidazole ($d_2$-lansoprazole)

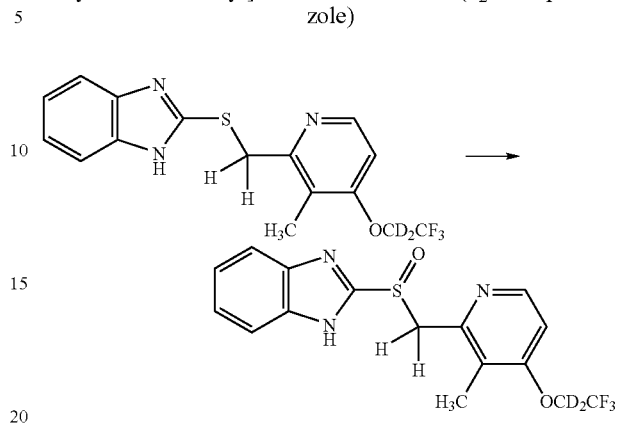

Prepared according to example 10.

Example 47

$d_4$-2-[3-Methyl-4-(2,2,2-trifluoroethoxy)-pyridin-2-ylmethanesulfinyl]-1H-benzoimidazole ($d_4$-lansoprazole)

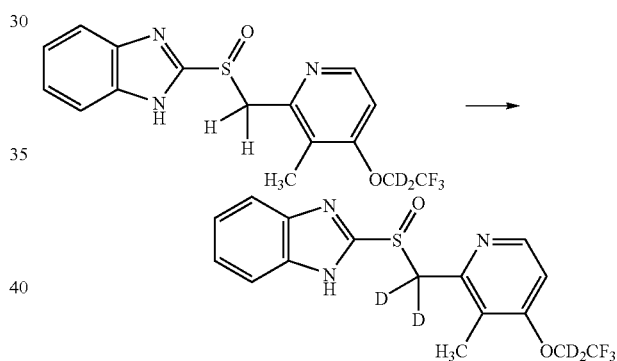

Prepared according to example 11, by substituting $D_2O$ for water and $CD_3OD$ for methanol.

Example 48

$d_2$-2-[3-Methyl-4-(2,2,2-trifluoroethoxy)-pyridin-2-ylmethanesulfinyl]-1H-benzoimidazole ($d_2$-lansoprazole)

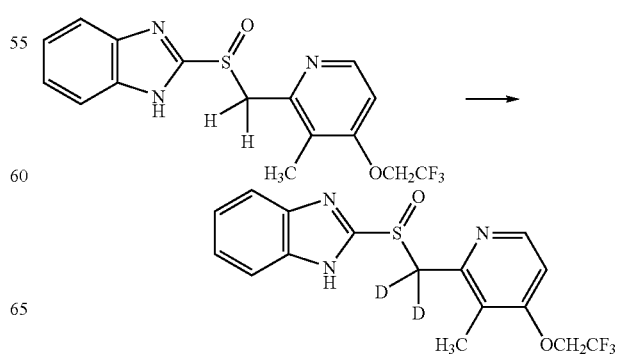

Prepared according to example 11, by substituting D₂O for water and CD₃OD for methanol.

Example 49 d₆-3-Methoxy-1-propanol

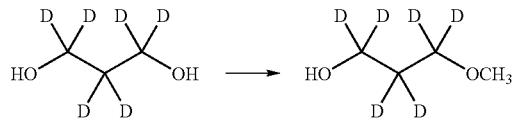

The procedure is carried out as described in Kulkarni et al, *Synthesis* 2004, 4, 595-599, which is hereby incorporated by reference in its entirety. A mixture of d₆-1,2-propanediol (Sigma-Aldrich) (1 mmol), CH₃I (1.25 mmol) and HgO (1.5 mmol) in dichloromethane was stirred at ambient temperature for 30 hours. The mixture was diluted with Et₂O, decanted and concentrated under reduced pressure to give the crude product which was purified by silica gel chromatography.

Example 50 d₉-3-Methoxy-1-propanol

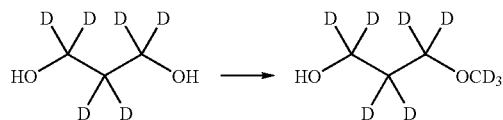

Prepared according to example 44, by substituting CD₃I for CH₃I.

Example 51 d₃-3-Methoxy-1-propanol

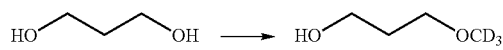

Prepared according to example 44, by substituting CD₃I for CH₃I.

Example 52 d₆-2-[4-(3-Methoxy-propoxy)-3-methyl-pyridin-2-ylmethylsulfanyl]-1H-benzoimidazole

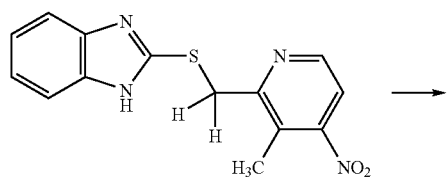

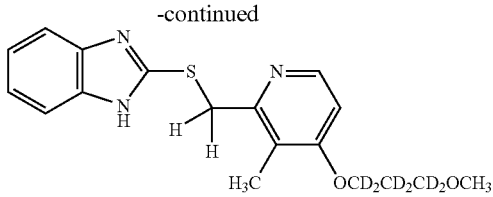

Prepared according to example 9, by substituting CH₃OCD₂CD₂CD₂ONa—CH₃OCD₂CD₂CD₂OH for CD₃ONa—CD₃OD.

Example 53 d₆-2-[4-(3-Methoxy-propoxy)-3-methyl-pyridin-2-ylmethanesulfinyl]-1H-benzoimidazole (d₆-rabeprazole)

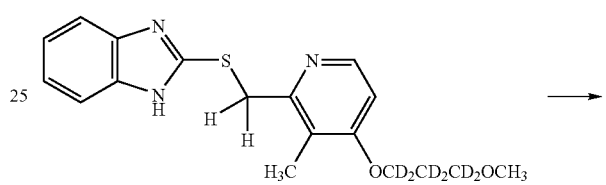

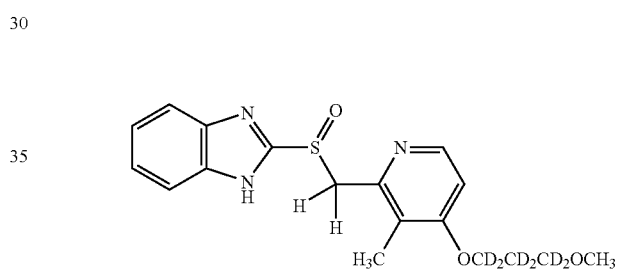

Prepared according to example 10.

Example 54 d₈-2-[4-(3-Methoxy-propoxy)-3-methyl-pyridin-2-ylmethanesulfinyl]-1H-benzoimidazole (d₈-rabeprazole)

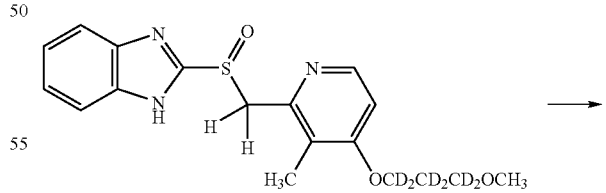

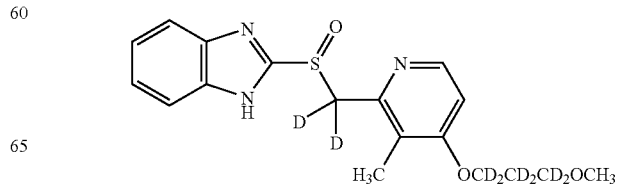

Prepared according to example 11, by substituting $D_2O$ for water and $CD_3OD$ for methanol.

Example 55

$d_9$-2-[4-(3-Methoxy-propoxy)-3-methyl-pyridin-2-ylmethalsulfanyl]-1H-benzoimidazole

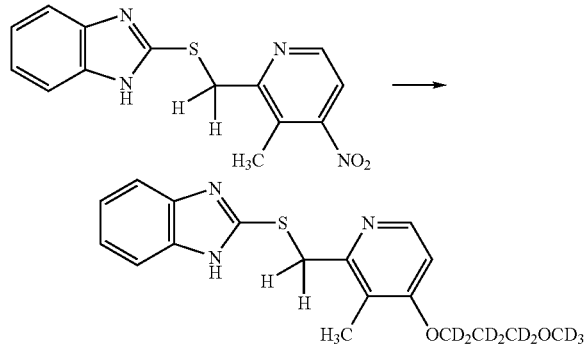

Prepared according to example 9, by substituting $CD_3OCD_2CD_2CD_2ONa$—$CD_3OCD_2CD_2CD_2OH$ for $CD_3ONa$—$CD_3OD$.

Example 56

$d_9$-2-[4-(3-Methoxy-propoxy)-3-methyl-pyridin-2-ylmethanesulfinyl]-1H-benzoimidazole ($d_9$-rabeprazole)

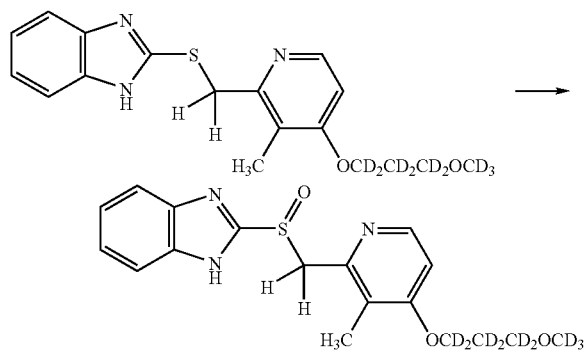

Prepared according to example 10.

Example 57

$d_{11}$-2-[4-(3-Methoxy-propoxy)-3-methyl-pyridin-2-ylmethanesulfinyl]-1H-benzoimidazole ($d_{11}$-rabeprazole)

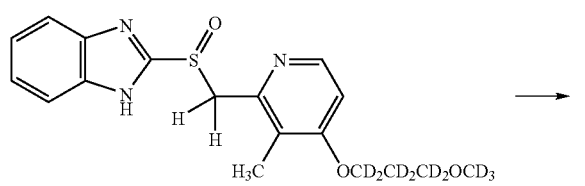

-continued

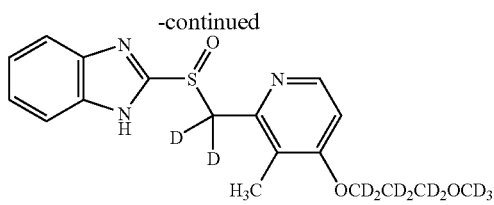

Prepared according to example 11, by substituting $D_2O$ for water and $CD_3OD$ for methanol.

Example 58

$d_3$-2-[4-(3-Methoxy-propoxy)-3-methyl-pyridin-2-ylmethylsulfanyl]-1H-benzoimidazole

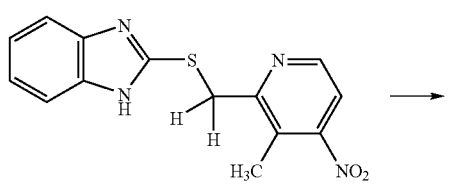

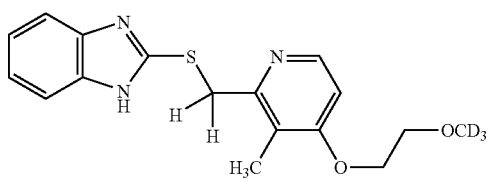

Prepared according to example 9, by substituting $CD_3OCH_2CH_2CH_2ONa$—$CD_3OCH_2CH_2CH_2OH$ for $CD_3ONa$—$CD_3OD$.

Example 59

$d_3$-2-[4-(3-Methoxy-propoxy)-3-methyl-pyridin-2-ylmethanesulfinyl]-1H-benzoimidazole ($d_3$-rabeprazole)

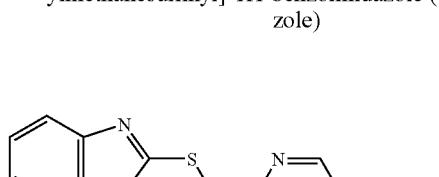

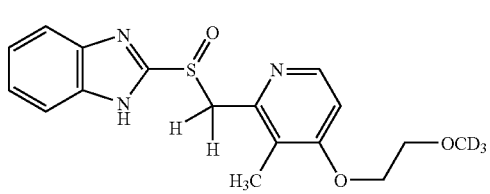

Prepared according to example 10.

Example 60

$d_5$-2-[4-(3-Methoxy-propoxy)-3-methyl-pyridin-2-ylmethanesulfinyl]-1H-benzoimidazole ($d_5$-rabeprazole)

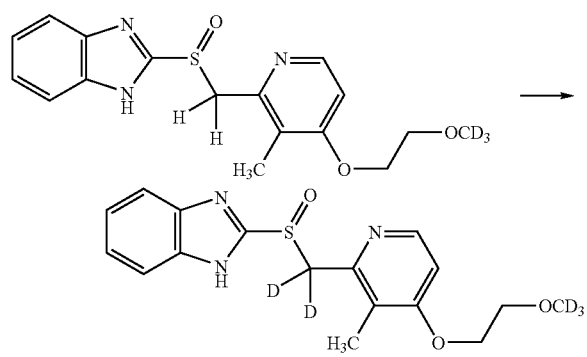

Prepared according to example 11, by substituting $D_2O$ for water and $CD_3OD$ for methanol.

Example 61

$d_2$-2-[4-(3-Methoxy-propoxy)-3-methyl-pyridin-2-ylmethanesulfinyl]-1H-benzoimidazole ($d_2$-rabeprazole)

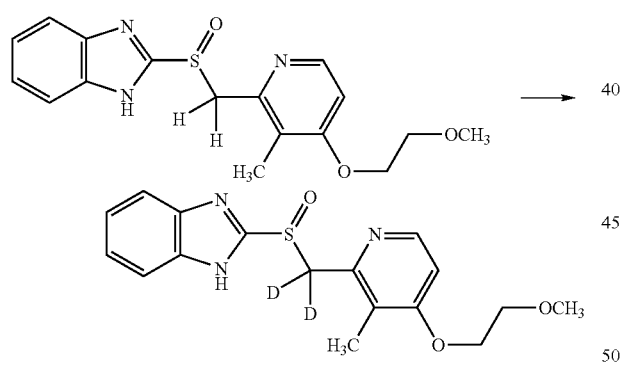

Prepared according to example 11, by substituting $D_2O$ for water and $CD_3OD$ for methanol.

Example 62

2-(4-Chloro-3-methoxy-pyridin-2-ylmethylsulfanyl)-5-difluoro-methoxy-1H-benzoimidazole

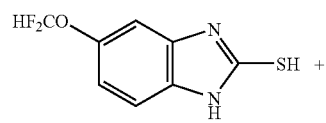

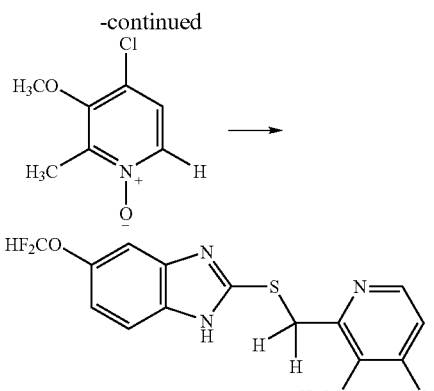

Prepared according to example 8.

Example 63

$d_5$-5-Difluoromethoxy-2-(3,4-dimethoxy-pyridin-2-ylmethylsulfanyl)-1H-benzoimidazole

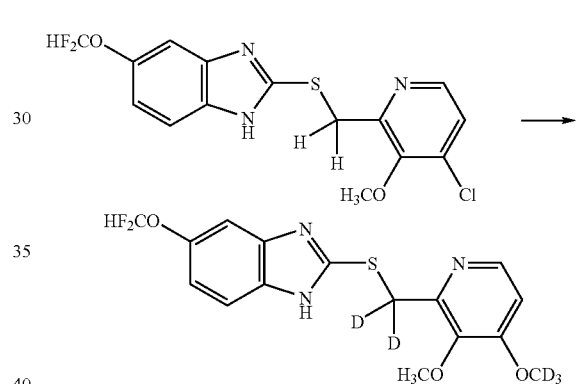

Prepared according to example 9.

Example 64

$d_5$-5-Difluoromethoxy-2-(3,4-dimethoxy-pyridin-2-ylmethanesulfinyl)-1H-benzoimidazole ($d_5$-pantoprazole)

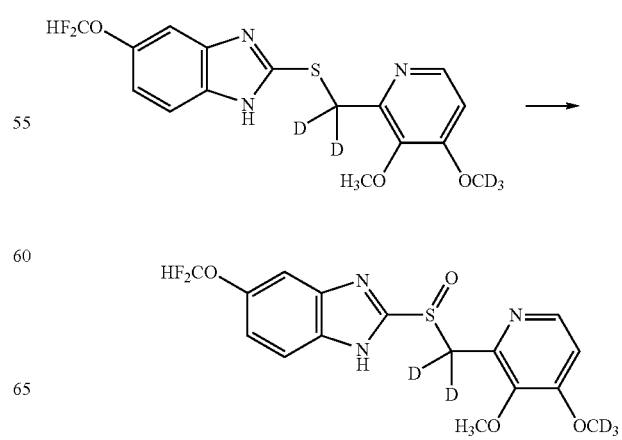

Prepared according to example 10.

Example 65

$d_3$-5-Difluoromethoxy-2-(3,4-dimethoxy-pyridin-2-ylmethanesulfinyl)-1H-benzoimidazole ($d_3$-pantoprazole)

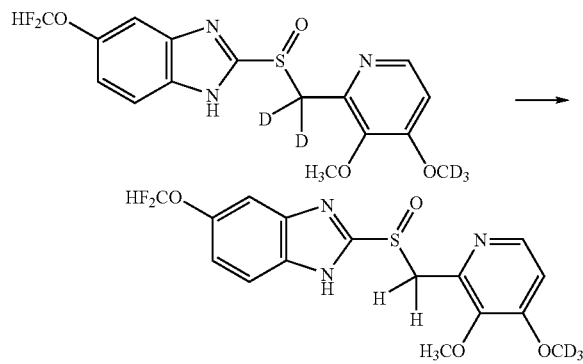

Prepared according to example 11.

Example 66

$d_2$-5-Difluoromethoxy-2-(3,4-dimethoxy-pyridin-2-ylmethanesulfinyl)-1H-benzoimidazole ($d_2$-pantoprazole)

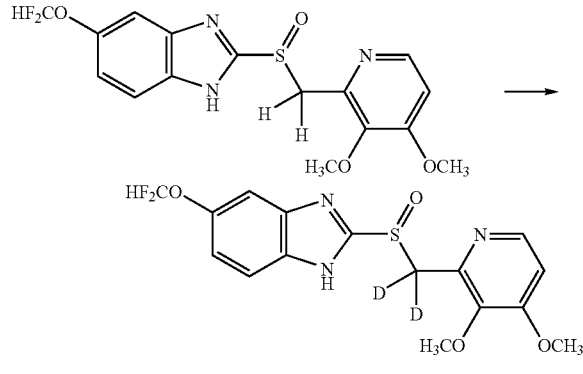

Prepared according to example 11, by substituting $D_2O$ for water and $CD_3OD$ for methanol.

Example 67

Human Liver Microsomal Stability Assay

Human liver microsomal stability assays were conducted at 1 mg per mL protein concentration with an NADPH-generating system (1.3 mM NADPH, 3.3 mM glucose 6-phosphate and 0.4 U per mL glucose 6-phosphate dehydrogenase) and 3.3 mM $MgCl_2$. Test compounds were added as acetonitrile solutions (final assay concentration of acetonitrile should be <1%) and incubated at 37° C. with shaking. Aliquots (150 µL) were removed at 0, 15, 30, 60, and 120 minutes, and ice cold acetonitrile (300 µL) was added to stop the reactions. Samples were centrifuged at 4000 RPM for 5 minutes to precipitate all proteins. Supernatants were transferred to microcentrifuge tubes and stored for LC/MS/MS analysis of the degradation half-life of the test compounds. It has thus been found that the compounds of formula (1) that are illustrated in Examples 10, 11, 13, 14, 18, 19, 20, 21, 25, 26, 27, 28, 32, 34, 39 41, and 43 above show an increase of 10% or more in the degradation half-life, as compared to the non-isotopically enriched drug. For example, the degradation half-life of $d_{15}$-omeprazole, $d_{13}$-omeprazole, $d_{13}$-(R)-omeprazole and $d_{13}$-esomeprazole is increased by 20-60% as compared to non-isotopically enriched omeprazole.

Example 68

Rat Gastric Activity, Pylorus Ligation

Compounds of formula (1) according to the present invention were evaluated for possible antisecretory activity in pylorus-ligated rats. A reduction of 50% or more in gastric acidity relative to the vehicle control group is considered significant in this experiment. Wistar derived male rats weighing 210±10 g were fasted overnight. Under propofol anesthesia (15 mg/kg i.v.), the abdominal cavity was exposed and a ligature was made just below the pylorus sphincter. $d_{15}$-Omeprazole (30 mg/kg) and vehicle (0.2% $NaHCO_3$/ 0.25% MC/2% Tween 80) were each administered orally (PO) 30 minutes before the ligation in a volume of 10 ml/kg body weight. Animals were sacrificed 4 hours later and the gastric contents were collected. After centrifugation, the volume of each sample was measured and acidity was determined by titration.

| | | | % inhibition relative to vehicle controls | | |
|---|---|---|---|---|---|
| Test Article | Route | Dose | Volume (mL/4 hours) | Acidity (µEq/mL) | Total Acid Output (µEq/4 hours) |
| $d_{15}$-omeprazole | PO | 30 mg/kg | 55% | 89% | 95% |

Example 69

In Vitro Metabolism Using Human Cytochrome $P_{450}$ Enzymes

The cytochrome $P_{450}$ enzymes are expressed from the corresponding human cDNA using a baculovirus expression system (BD Biosciences). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula 1, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g. acetonitrile, 20% trichloroacetic acid, 94% acetonitrile/ 6% glacial acetic acid, 70% perchloric acid, 94% acetonitrile/ 6% glacial acetic acid) and centrifuged (10,000 g) for 3 minutes. The supernatant is analyzed by HPLC/MS/MS.

| Cytochrome P$_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Example 70

In Vitro Inhibition of Dog Kidney H$^+$/K$^+$-ATPase Activity

The procedure is carried out as described in Yoda et al Biochem. Biophys. Res. Comm. 1979, 40, 880, which is hereby incorporated by reference in its entirety. Compounds of Formula 1 or the corresponding non-isotopically enriched compounds or standards or controls are incubated with dog kidney H$^+$/K$^+$-ATPase enzyme (20 micrograms) in HEPES buffer (50 millimolar, pH 7.4) in presence of (millimolar) 140 NaCl, 10 KCl, 3 ATP-Mg, 0.5 EDTA, and PSBs (0-300 micromolar). At the end of the incubation the inorganic phosphate released from ATP is determined.

Example 71

In Vitro Inhibition of Pig Stomach Gastric Vesicle H$^+$/K$^+$-ATPase Activity

The procedure is carried out as described in Ljungstrom et al Biochim. Biophys. Acta 1984, 769, 209-219, which is hereby incorporated by reference in its entirety. Membrane vesicles containing H$^+$/K$^+$-ATPase are prepared from pig stomach. The ATPase activity is measured at 37° C. as the release of inorganic phosphate from ATP. In detail, compounds of Formula 1 or the corresponding non-isotopically enriched compounds or standards or controls at a single concentration of 10 micromolar, or for determination of IC$_{50}$ values in concentrations of 0.01-100 micromolar, are preincubated in enzyme-containing buffers pH 6.0. After preincubation (37° C., 30 min), the medium of pH 6.0 is adjusted with a HEPES-Tris buffer to pH 7.4. The enzyme reaction is started by the addition of Tris-ATP. The total reaction volume is 1 milliliter, containing 20 micrograms of vesicular protein, 4 millimolar MgCl$_2$, 10 millimolar KCl, 20 micrograms Nigericin, 2 millimolar Tris-ATP, 10 millimolar Hepes, and additionally 2 millimolar Pipes for the preincubation medium at pH 6.0. After 4 min the reaction is stopped by the addition of 10 microliters of 50% trichloroacetic acid. The denatured protein is spun down, and the P$_i$ content is determined as described (Le Bel, 1978). The hydrolysis of ATP should not exceed 15%. Inhibition is calculated as percent inhibition against maximal stimulation, and IC$_{50}$ is calculated by probit analysis.

Example 72

[$^{14}$C]Aminopyrine Accumulation in Isolated Rabbit Gastric Glands

The procedure is carried out as described in Berglindh et al. Acta Physiol. Scand. 1976, 96, 150-169, which is hereby incorporated by reference in its entirety. Rabbits (2-3 kilogram) are sacrificed by cervical fracture/dislocation during anesthesia. The gastric mucosa in the corpus part is scraped off and minced with a pair of scissors. Mucosa pieces are incubated in a collagenase-containing medium (1 milligrams per milliliter) for 30-45 min at 37° C. The medium composition (in millimolar) is as follows: 100.0 NaCl, 5.0 KCl, 0.5 NaH$_2$PO$_4$, 1.0 Na$_2$HPO$_4$, 1.0 CaCl$_2$, 1.5 MgCl$_2$, 20.0 NaHCO$_3$, 20.0 HEPES, 2 milligrams per milliliter glucose, and 1 milligrams per milliliter rabbit albumin. The pH is adjusted to 7.4 with 1 M Tris. The glands are filtered through a nylon mesh to remove coarse fragments and rinsed three times with incubation medium. The glands are diluted to a final concentration of 2-4 mg dry weight/milliliter. The ability of gastric glands to form acid is measured based on aminopyrine (AP) accumulation (Berglindh, 1976). Samples of 1.0-milliliter gland suspension are equilibrated in 1.0 milliliter of medium containing 0.1 microcurie per milliliter $^{14}$C-AP at 37° C. in a shaking water bath together with compounds of Formula 1 or the corresponding non-isotopically enriched compounds or standards or controls. After 20 min, 1 millimolar dbcAMP is added, followed by a 45-min incubation period. The glands are then separated from the medium by brief centrifugation, and aliquots of supernatant and the digested gland pellet are used for measurements in a liquid scintillation counter. The AP accumulation is calculated as the ratio between AP in intraglandular water and AP in the incubation medium (Sack, 1982). All determinations are made in triplicate. IC$_{50}$ is calculated by probit analysis where 0% corresponds to basal and 100% to maximal stimulated AP ratio.

Example 73

Inhibition of Acid Secretion in Isolated Rabbit Gastric Glands

White New Zealander Rabbit fundic glands are obtained by high-pressure perfusion of the circulation of the stomach and subsequent collagenase treatment of pieces of fundic mucosa. After the glands have been washed several times, they are placed in 20-milliliter vials with dibutyryl cyclic AMP (1 millimolar) and the test compound (3×10$^{-8}$ to 10$^{-4}$ molar) in the presence of [$^{14}$C]-aminopyrine (0.125 micromolar) and are incubated at 37° C. The incubate is agitated (150 oscillations per minute) for 30 minutes and the reaction stopped by centrifugation (10 seconds at 20,000 g). The ability of the glands to maintain a pH gradient to the medium (pH 7.4) on stimulation with dibutyryl cyclic AMP is measured by means of the concentration ratio of [$^{14}$C]-aminopyrine between glands and medium as described in Berglindh et al. *Acta Physiol. Scand.* 1976, 96, 150-169.

Example 74

Inhibition of *Helicobacter pylori* Urease Activity

Bacteria incubated for 3 days at 37° C. under microaerophilic conditions (85% $N_2$, 10% $CO_2$, and 5% $O_2$) are gently scraped off from the Columbia blood agar plates and washed with PBS (137 millimolar NaCl, 5.1 millimolar $Na_2$-$HPO_4$, 2.7 millimolar KCl, and 0.88 millimolar $KH_2PO_4$) adjusted to the pH, which is to be used in the assay. The suspension is centrifuged at 2773 g for 10 min at ambient temperature, and the bacteria are collected. After two additional washings, the suspension is adjusted to $A_{560}$=0.3. The concentration of purified Jack bean Urease used (18 micrograms per milliliter, 1.28 U/mL) gave the same Urease activity as the bacterial suspension. Compounds of Formula 1 or the corresponding non-isotopically enriched compounds or standards or controls are dissolved in MeOH or DMSO and when necessary sonicated for some minutes. Aliquots are added to the test solutions to final concentrations of 1, 10, and 100 micromolar (with the exception of Flurofamide where the concentrations used are 1, 10, and 100 nanomolar), and the organic solvent component amounted to 51%. The samples are incubated for 30 min at 37° C. in a water bath with gentle shaking. The reaction is started by adding 1 part 200 millimolar urea solution to 1 part test solution and stopped 10 min later by adding 25 parts reagent A (10 gram of phenol and 50 milligrams of $Na_2Fe(CN)_5NO$ dissolved in 1 liter of water) and 25 parts reagent B (5 gram of NaOH and 8.4 milliliter of NaOCl (Sigma-Aldrich) dissolved in 1 liter of water). The samples are incubated for a further 15 min to allow color development, after which 200 microliters aliquots are transferred to 96-well microtiter plates. The absorbance at 650 nm is determined at ambient temperature using $(NH_3)_2SO_4$ as standard.

Example 75

Anti-Helicobacter Pylori Activity in Mice

SPF mice are challenged with bacteria three times during a 6-day period, and 3 weeks after inoculation animals are treated orally according to different regimens for 4 weeks. Six different regimens are selected as follows: an uninfected no treatment control, an infected no treatment group to check for spontaneous elimination of the infection, an infected group receiving vehicle only, a triple therapy group used as a positive eradication control, and, finally, the three groups to be studied, using a compound of Formula 1, the corresponding non-isotopically enriched compound or standard or control and a therapeutic dose Flurofamide.

Methocel vehicle (0.1 milliliter) adjusted to pH 6 with citric acid is used and given twice daily. Compounds are given either dissolved or suspended in the vehicle, and the amounts stated are per mouse, mean body weight of 30 gram, and day. Stock solutions or suspensions are stored frozen.

Triple therapy is made up by 0.185 milligrams of bismuth, 0.675 milligrams of metronidazole, and 1.500 milligrams of tetracycline and is administered once daily for 2 weeks followed by bismuth alone once daily for another 2 weeks. In this group of animals, vehicle alone is administered at the second daily dosing occasion.

Compounds of Formula 1, the corresponding non-isotopically enriched compounds or standards or controls (125 micromole per kg) or Flurofamide (230 micromole per kg) are each dosed twice daily for 4 weeks. Animals are sacrificed 24 h or 5 weeks after cessation of the treatment to measure suppression and eradication, respectively. The assessment is done by checking mouse stomach specimens for Urease activity, and the rate of both suppression and eradication for each regimen is expressed as the number of Urease positive animals divided by the number of animals checked×100% as described in Dick-Hegedus et al *Scand. J. Gastroenterol.* 1991, 26, 909-915 Hazell et al *Am. J. Gastroenterol.* 1987, 82, 292-296, both of which are incorporated by reference in their entireties.

Example 76

Elevation of Serum Gastrin Levels in Pylorus-Ligated Rats

This study is performed in female Wistar rats as described Shay et al *Gastroenterology* 1954, 26, 906-913 and Herling et al *Eur. J Pharmacol.* 1988, 156, 341-350, both of which are incorporated by reference in their entireties. Food is withdrawn 16 h before the start of the study, and water is available ad libitum. Following pylorus ligation (performed under anesthesia), the compounds of Formula 1 or the corresponding non-isotopically enriched compounds or standards or controls are administrated intraperitoneally (ip). Compounds of Formula 1 or the corresponding non-isotopically enriched compounds or standards or controls are suspended in Tylose (1%) and administered at a volume of 2 milliliter per kilogram at a dose of 5 milligrams per kilogram. Gastric acid secretion is stimulated by a subcutaneous (sc) injection of Desglugastrin at a dose of 400 micrograms per kilogram. This latter injection is repeated 1 h later. Three hours after the start of the experiment, the animals are sacrificed, the stomach is excised, and the accumulated gastric juice is collected and its volume measured. Acid concentration is measured by electrotitration against 100 millimolar NaOH to an endpoint of pH 7. Total acid output (millimole of $H^+$/3 hours) is calculated. Percent inhibition of the treated rat group is calculated against the control group.

Example 77

Inhibition of Gastric Acid Secretion in Stomach-Lumen-Perfused Rats

Gastric acid secretion in anesthetized male Sprague-Dawley rats is determined as described Barrett *J Pharm. Pharmacol.* 1966, 18, 633-639 and Herling et al *Eur. J Pharmacol.* 1988, 156, 341-350, both of which are incorporated by reference in their entireties. The animals are fasted for 18 h prior to the experiment and receive water ad libitum. They are anesthetized with 30% (w/v) urethane (5 milligrams per kilogram im) and tracheotomized. The esophagus and pylorus are ligated, and a double lumen perfusion cannula is inserted and fixed in the fore-stomach. The stomach is perfused continuously with warm (37° C.) saline at a rate of 1 milliliter per minute. The perfusate is collected at 15-minute periods and its acid concentration measured by electrotitration against 100 millimolar NaOH to an endpoint of pH 7, and acid output (micromolar of $H^+$/15 minute) is calculated. To stimulate acid secretion, histamine (10 milligrams per kilogram per hour) is administered after a basal period of 45 minutes by iv infusion into the jugular vein, and observation is continued until acid output reaches a stable plateau (Herling, 1986). Compounds of Formula 1 or the corresponding non-isotopically enriched compounds or standards or controls are administered iv (25%

DMSO, 1 milliliter per rat). Maximal inhibition is calculated as percent change versus pre-dose value and presented as mean+/−SEM.

Example 78

Inhibition of Gastric Acid Secretion in Heidenhain-Pouch Dogs

Male Beagle dogs are equipped with a Heidenhain-pouch as described De Vito et al *J. Appl. Physiol.* 1959, 14, 138-139 and Herling et al *Eur. J. Pharmacol.* 1988, 156, 341-350, both of which are incorporated by reference in their entireties. For intraduodenal (id) administration studies, three dogs received an additional cannula in the flexura duodenojejunalis. The dogs are trained to stay in a Pawlow stand. Food is withdrawn 18 h prior to the experiment and water is available ad libitum. Gastric acid secretion is induced with an iv infusion of 0.05 milligrams per kilogram per h of histamine, which produces a maximal stimulation. Gastric juice is collected from the pouch at 30-min intervals, and acidity is measured by titration against 100 millimolar NaOH to an endpoint of pH 7, and acid output (millimole $H^+$/30 minute) is calculated. Compounds of Formula 1 or the corresponding non-isotopically enriched compounds or standards or controls (in 25% DMSO) are administered at doses of 0.3 milligrams per kilogram iv or 1 milligrams per kilogram id at a volume of 20 milliliter per dog as soon as acid secretion stabilizes. Maximal inhibition is calculated as percent change against pre-dose value and presented as mean=/− SEM. $ED_{50}$ values and confidence limits (95%) are calculated according to Lichtfield and Wilcoxon, Lichtfield et al *J. Pharmacol. Exp. Ther.* 1949, 96, 99-113, which is hereby incorporated by reference in its entirety.

Example 79

Determination of Serum Gastrin Levels in Rats

Female Wistar rats are treated orally for 10 weeks with 30 milligrams per kilogram per day of compounds of Formula 1 or the corresponding non-isotopically enriched compounds or standards or controls. At days 1 to 3, rats receive said compound by intraperitoneal (ip) administration, to cause gastric acid inhibition and therefore to reduce the acidic degradation of subsequent orally administered test compounds to 10 weeks. Said compounds are suspended in potato starch mucilage (20 milligrams per milliliter) and administered at a volume of 2 milliliter per kilogram. A control group is also included in the experiment. Blood samples are collected retroorbitally during anesthesia. Serum Gastrin levels (picogram per milliliter) are determined by using a commercially available RIA kit and presented as means+/− SEM. Significant differences (p<0.05) are calculated by Students t-test.

Example 80

Human Metabolism Studies

A mixture containing an equal amount of a compound of Formula 1 and the corresponding non-isotopically enriched compound or standard or control are administered to the subjects either orally or by intravenous infusion. Blood specimens are drawn before dosing and at 0, 2, 5, 15, 20, and 45 minutes, and 1, 1.5, 2, 2.5, 3, 4, 6, 8, 12, 24 and 48 hours post dose. Serum is decanted immediately, and stored at −10° C. Serum concentrations of said compound and the corresponding non-isotopically enriched compound or standard or control are analyzed by HPLC/MS/MS.

REFERENCES CITED

The disclosures of each of the following references are incorporated by reference herein in their entireties.

U.S. Patent Documents
U.S. Pat. No. 4,069,346 Feb. 14, 1977 McCarty.
U.S. Pat. No. 5,386,032 Jan. 31, 1995 Brandstrom.
U.S. Pat. No. 5,589,491 Dec. 31, 1996 Nakanishi.
U.S. Pat. No. 5,599,794 Feb. 4, 1997 Eek.
U.S. Pat. No. 5,629,305 May 13, 1997 Eek.
U.S. Pat. No. 5,690,960 Nov. 25, 1997 Bengtsson.
U.S. Pat. No. 5,714,505 Feb. 3, 1998 Hasselkus.
U.S. Pat. No. 5,731,002 Mar. 24, 1998 Olovson.
U.S. Pat. No. 5,817,338 Oct. 6, 1998 Bergstrand.
U.S. Pat. No. 5,846,514 Dec. 8, 1998 Foster.
U.S. Pat. No. 5,877,192 Mar. 2, 1999 Lindberg.
U.S. Pat. No. 5,900,424 May 4, 1999 Kallstrom.
U.S. Pat. No. 5,948,789 Sep. 7, 1999 Larsson.
U.S. Pat. No. 5,958,955 Sep. 28, 1999 Gustavsson.
U.S. Pat. No. 6,013,281 Jan. 11, 2000 Lundberg.
U.S. Pat. No. 6,090,827 Jul. 18, 2000 Erickson.
U.S. Pat. No. 6,132,770 Oct. 17, 2000 Lundberg.
U.S. Pat. No. 6,132,771 Oct. 17, 2000 Depui.
U.S. Pat. No. 6,136,344 Oct. 24, 2000 Depui.
U.S. Pat. No. 6,221,335 Apr. 24, 2001 Foster.
U.S. Pat. No. 6,245,913 Jun. 12, 2001 Singh.
U.S. Pat. No. 6,284,271 Sep. 4, 2001 Lundberg.
U.S. Pat. No. 6,303,788 Oct. 16, 2001 Cotton.
U.S. Pat. No. 6,333,342 Dec. 25, 2001 Foster.
U.S. Pat. No. 6,334,997 Jan. 1, 2002 Foster.
U.S. Pat. No. 6,365,184 Apr. 2, 2002 Depui.
U.S. Pat. No. 6,342,507 Jan. 29, 2002 Foster.
U.S. Pat. No. 6,476,058 Nov. 5, 2002 Foster.
U.S. Pat. No. 6,503,921 Jan. 7, 2003 Naicker.
U.S. Pat. No. 6,593,339 Jul. 15, 2003 Eek.
U.S. Pat. No. 6,605,303 Aug. 12, 2003 Karehill.
U.S. Pat. No. 6,605,593 Aug. 12, 2003 Naicker.
U.S. Pat. No. 6,610,323 Aug. 26, 2003 Lundberg.
U.S. Pat. No. 6,613,739 Sep. 2, 2003 Naicker.
U.S. Pat. No. 6,623,759 Sep. 23, 2003 Heese.
U.S. Pat. No. 6,710,053 Mar. 23, 2004 Naicker.
U.S. Pat. No. 6,818,200 Nov. 16, 2004 Foster.
U.S. Pat. No. 6,884,429 Apr. 26, 2005 Koziak.

OTHER REFERENCES

Center for Drug Evaluation and Research, application number 21-153/21-154 for Esomeprazole Magnesium (Nexium).

Altermatt, Cancer 1988, 62(3), 462-466, "Heavy water delays growth of human carcinoma in nude-mice".

Altermatt, *International Journal of Cancer* 1990, 45(3), 475-480, "Heavy-water enhances the antineoplastic effect of 5-fluoro-Uracil and Bleomycin in nude mice bearing human carcinoma".

Barrett *J. Pharm. Pharmacol.* 1966, 18, 633-639, "Specific stimulation of gastric acid secretion by a pentapeptide derivative of Gastrin"

Baselt, *Disposition of Toxic Drugs and Chemicals in Man*, 2004, 7th Edition.

Berglindh et al *Acta Physiol. Scand.* 1976, 97, 401-414, "Effects of secretagogues on oxygen consumption, aminopyrine accumulation and morphology in isolated gastric glands"

Berglindh et al. *Acta Physiol. Scand.* 1976, 96, 150-169, "A method for preparing isolated glands from the rabbit gastric mucosa"

Brandstrom, *Acta Chemica Scandinavica* 1989, 43, 595-611, "Chemical reactions of Omeprazole analogues. VI. The reaction of Omeprazole in the absence of 2-mercaptoethanol"

Browne, *Synthesis and Applications of Isotopically Labelled Compounds, Proceedings of the International Symposium,* 7th, Dresden, Germany, Jun. 18-22, 2000, 519-532, "Stable Isotopes in Pharmaceutical Research and Development".

Browne, *Pharmacochemistry Library,* 1997, 26, "Stable isotopes in pharmaceutical research".

Browne, *Pharmacochemistry Library,* 1997, 26, 13-18, "Isotope effect: implications for pharmaceutical investigations".

Browne, *Clinical Pharmacology & Therapeutics,* 1981, 29(4), 511-15, "Kinetic equivalence of stable-isotope-labeled and unlabeled phenytoin".

Browne, *Journal of Clinical Pharmacology* 1982, 22(7), 309-15, "Pharmacokinetic equivalence of stable-isotope-labeled and unlabeled drugs. Phenobarbital in man".

Browne, *Synth. Appl. Isot. Labeled Compd, Proc. Int. Symp.* 1983, Meeting Date 1982, 343-8, "Applications of stable isotope tracer methods to human drug interaction studies".

Browne, *Therapeutic Drug Monitoring* 1984, 6(1), 3-9, "Applications of stable isotope methods to studying the clinical pharmacology of antiepileptic drugs in newborns, infants, children, and adolescents".

Cotton et al., *Tetrahedron. Asymmetry,* 2000, 11(18), 3819-3825, "Asymmetric Synthesis of Esomeprazole."

Crowe, *Journal of Labelled Compounds and Radiopharmaceuticals,* 1986, 23(1), 21-33, "The Preparation of $^{14}$C, $^{35}$S and $^{13}$C Labelled forms of Omeprazole".

De Vito et al *J. Appl. Physiol.* 1959, 14, 138-139, "Techniques in Heidenhain Pouch experiments"

Dick-Hegedus et al *Scand. J. Gastroenterol.* 1991, 26, 909-915, "Use of a mouse model to examine anti-Helicobacter pylori agents"

Ding et al *Journal of Neurochemistry* 1995, 65(2), 682-690, "Mechanistic Positron Emission Tomography Studies of 6-[$^{18}$F]Fluorodopamine in Living Baboon Heart: Selective Imaging and Control of Radiotracer Metabolism Using the Deuterium Isotope Effect".

Foster, *Trends in Pharmacological Sciences* 1984, 5(12), 524-527.

Garland, *Synth. Appl. Isot. Labeled Compd. Proc. Int. Symp.* $2^{nd}$, 1986, Meeting Date 1985, 283-284.

Hazell et al *Am. J. Gastroenterol.* 1987, 82, 292-296, "Detection of Campylobacter pylori as a marker of bacterial colonisation and gastritis"

Herling et al *Eur. J. Pharmacol.* 1988, 156, 341-350, "Effects of Verapamil on gastric acid secretion in-vitro and in-vivo"

Herling et al. *Eur. J. Pharmacol.* 1986, 125, 233-239, "The stimulatory effect of Forskolin on gastric acid secretion in rats"

Hoffmann, *Drug Metabolism and Disposition* 1986, 14(3), 341-348, "Identification of the main urinary metabolites of Omeprazole after an oral dose to rats and dogs".

Kaufman, *Phys. Rev.* 1954, 93, 1337-1344, "The natural distribution of tritium".

Ko et al *British Journal of Clinical Pharmacology* 2000, 49(4), 343-351, "In Vitro Inhibition of the Cytochrome P450 (CYP450) System by the Antiplatelet Drug Ticlopidine: Potent Effect on CYP2C19 and CYP2D6".

Kritchevsky, *Annals of the New York Academy of Science* 1960, vol. 84, article 16, "Deuterium isotope effects in chemistry and biology".

Kuehler, *J. Med. Chem.* 1995, 38, 4906-4916, "Structure-Activity Relationship of Omeprazole and Analogs as *Helicobacter pylori* Urease Inhibitors".

Kubo, *Chem. Pharm. Bull.* 1990, 38(10), 2853-2858, "Synthesis of 2-[[(4-fluoroalkoxy-2-pyridyl)methyl]sulfinyl]-1H-benzimidazoles as antiulcer agents".

Kulkarni et al, *Synthesis,* 2004, 4, 595-599, "Sythnesis of the Marine Compound (2R,5Z,9Z)-2-Methoxyhexacosa-5,9-Dienoid Acid Via a Lipase-Catalyzed Resolution and a Novel O-Alkylation Protocol"

Kushner, *Can. J. Physiol. Pharmacol.* 1999, 77, 79-88, "Pharmacological uses and perspectives of heavy water and deuterated compounds".

Lamprect, *European Journal of Cell Biology* 1990, 51(2) 303-312, "Mitosis arrested by deuterium oxide-light microscopic, immunofluorescence and ultrastructural characterization".

Le Bel et al *Anal. Biochem.* 1978, 85, 86-89, "Convenient method for the ATPase assay"

Lewis, *J. Am. Chem. Soc.* 1968, 90, 4337, "The influence of tunneling on the relation between tritium and deuterium isotope effects. The exchange of 2-nitropropane-2-T".

Li et al *Rapid Communications in Mass Spectrometry* 2005, 19(14), 1943-1950, "Simultaneously Quantifying Parent Drugs and Screening for Metabolites in Plasma Pharmacokinetic Samples Using Selected Reaction Monitoring Information-Dependent Acquisition on a Qtrap Instrument".

Lichtfield et al *J. Pharmacol. Exp. Ther.* 1949, 96, 99-113, "A simplified method of evaluating dose-effect experiments"

Lindberg, *J. Med. Chem.* 1986, 29, 1327-1329, "The mechanism of action of the antisecretory agent Omeprazole"

Ljungström et al *Biochim. Biophys. Acta* 1984, 769, 209-219, "Characterization of proton-transporting membranes from resting pig gastric mucosa"

March, *Advanced Organic Chemistry,* 1992, 4th edition, 226-230

Pohl, *Drug Metabolism Reviews* 1985, Volume Date 1984, 15(7), 1335-1351

Roecker, *J. Am. Chem. Soc.* 1987, 109, 746, "Hydride transfer in the oxidation of alcohols by $[(bpy)_2(py)Ru(Q)]^{2+}$. A $k_H/k_D$ kinetic isotope effect of 50"

Raju et al. *Organic Process Research & Development,* 2006, 10, 33-35, "Preparation of Optically Pure Esomeprazole and Its Related Salt"

Sack et al *Am. J. Physiol.* 1982, 243, G313-G319, "Aminopyrine accumulation by mammalian gastric glands: an analysis of the technique"

Schroeter, *European Journal of Cell Biology* 1992, 58(2), 365-370, "Deuterium oxide arrests the cell-cycle of PTK2 cells during interphase".

Shay et al *Gastroenterology* 1954, 26, 906-913, "Quantitative method for measuring spontaneous gastric secretion in the rat"

Stenhoff, *Journal of Chromatography B* 1999, 734, 191-201, "Determination of the enantiomers of Omeprazole in blood plasma by normal-phase liquid chromatography and detection by atmospheric pressure ionization tandem mass spectrometry"

Tolonen, *European Journal of Pharmaceutical Sciences* 2005, 25, 155-162, "A simple method for differentiation of monoisotopic drug metabolites with hydrogen-deuterium exchange liquid chromatography/electrospray mass spectrometry"

Thomson, *International Series of Monographs on Pure and Applied Biology, Modern trends in Physiological Sciences,* 1963, "Biological Effects of deuterium"

Urey, *Phys. Rev.* 1932, 39, 164 "A hydrogen isotope of mass 2"

Yoda et al *Biochem. Biophys. Res. Comm.* 1979, 40, 880 "On the reversibility of binding of cardiac steroids to a partially purified $Na^+/K^+$-activated ATPase from beef brain"

Although the invention has been described with reference to the above example, it will be understood that modifications and variations are encompassed within the spirit and scope of the invention. Accordingly, the invention is limited only by the following claim.

What is claimed is:

1. A compound of Formula 1

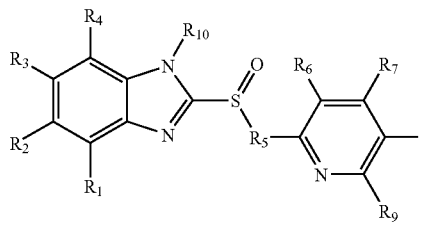

Formula 1 or a single enantiomer, a mixture of the (+)-enantiomer and the (−)-enantiomer, an individual diastereomer, a mixture of diastereomers, or a pharmaceutically acceptable salt thereof, wherein:

$R_1$, $R_4$, $R_9$ and $R_{10}$ are each independently hydrogen or deuterium;

$R_2$, $R_3$, $R_6$ and $R_8$ are each independently selected from the group consisting of hydrogen, deuterium, $C_1$-$C_6$ alkyl, and $C_1$-$C_6$ alkyloxy;

$R_5$ is selected from the group consisting of —$CH_2$—, —CHD— and —$CD_2$—; and $R_7$ is selected from the group consisting of hydrogen, deuterium, —$NO_2$, $C_1$-$C_6$ alkyl, and $C_1$-$C_6$ alkyloxy;

if $R_1$, $R_3$, and $R_4$ are deuterium, $R_2$ is —$OCH_3$, $R_6$ is $CH_3$, $R_7$ is $OCH_3$, and $R_8$ is —$CH_3$, then at least one of $R_5$, $R_9$, and $R_{10}$ has deuterium enrichment of at least about 1%;

if $R_1$, $R_2$, $R_3$, and $R_4$ are deuterium, is $R_6$ is —$CH_3$, and $R_7$ is —$OCH_2CF_3$, then at least one of $R_8$, $R_9$, and $R_{10}$ has deuterium enrichment of at least about 1%;

if $R_2$ is —$OCHF_2$, $R_6$ is —$OCH_3$, and $R_7$ is —$OCD_3$, then at least one of $R_1$, $R_3$, $R_4$, $R_5$, $R_8$, $R_9$, and $R_{10}$ has deuterium enrichment of at least about 1%;

provided that said compound of Formula 1 contains at least one deuterium atom; and provided that deuterium enrichment in said compound of Formula 1 is at least about 1%.

2. The compound of claim 1, wherein said compound contains about 90% or more by weight of the (−)-enantiomer of said compound and about boo or less by weight of (+)-enantiomer of said compound.

3. The compound of claim 1, wherein said compound contains about 90% or more by weight of the (+)-enantiomer of said compound and about boo or less by weight of (−)-enantiomer of said compound.

4. The compound of claim 1, wherein said alkyl is selected from the group consisting of methyl, ethyl, n-propyl, iso-propyl, n-butyl, sec-butyl, and tert-butyl.

5. The compound of claim 1, wherein said alkyloxy is selected from the group consisting of methoxy, ethoxy, n-propoxy, iso-propoxy, n-butoxy, sec-butoxy, and tert-butoxy.

6. A compound selected from the group consisting of:

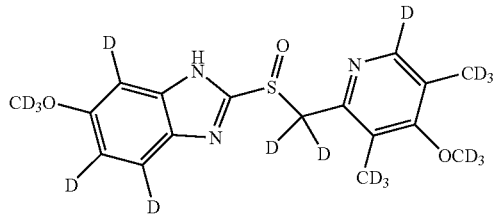

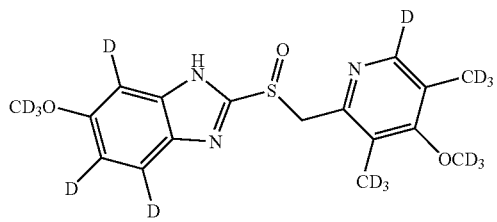

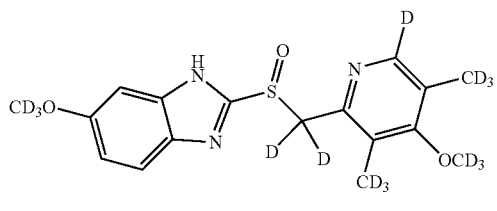

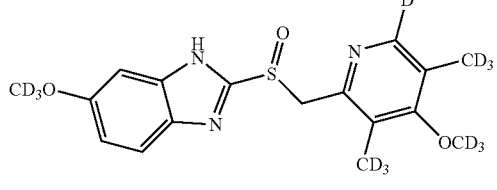

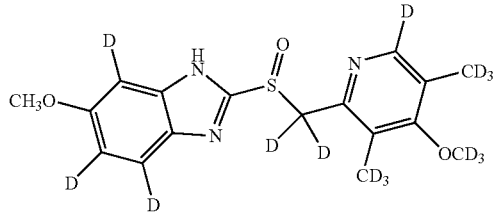

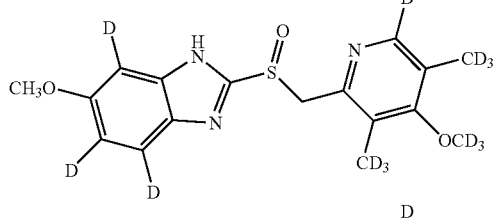

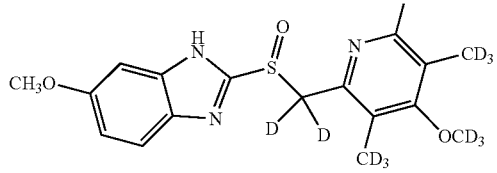

-continued
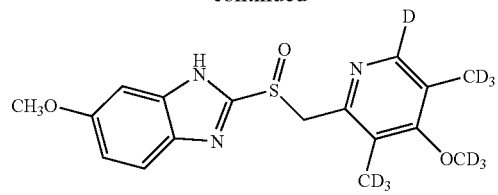
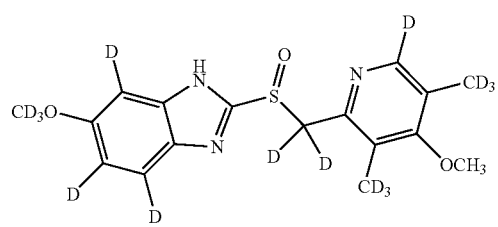
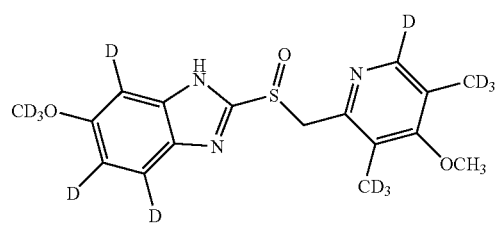
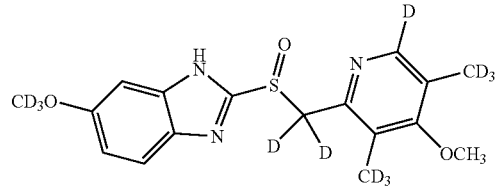
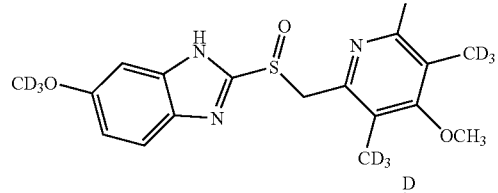
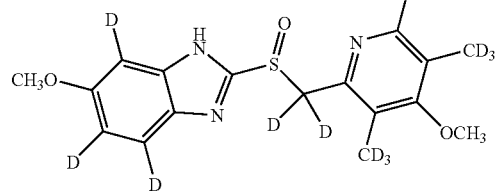
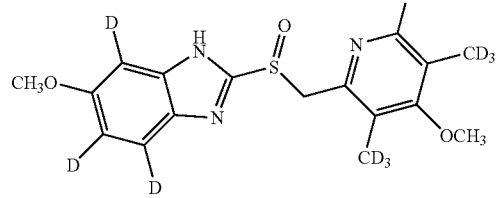
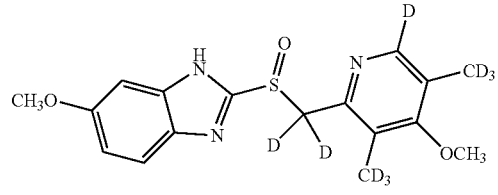
-continued
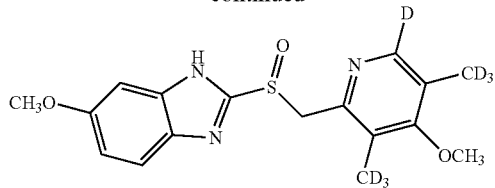
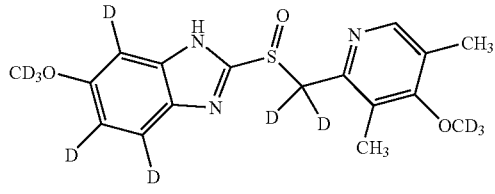
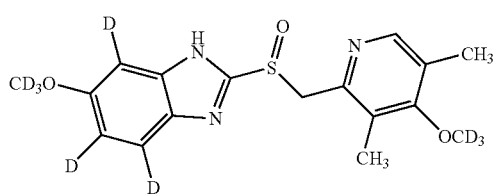
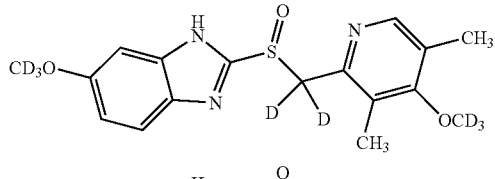
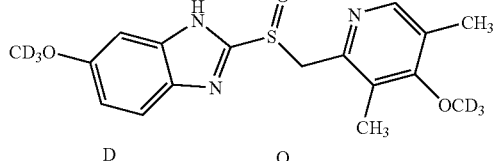
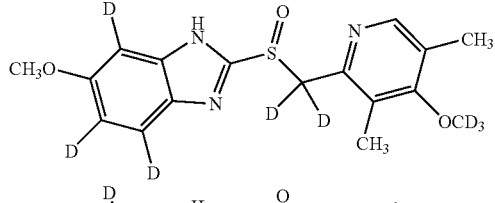
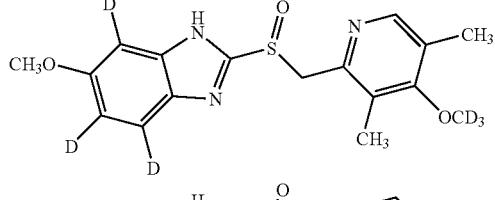
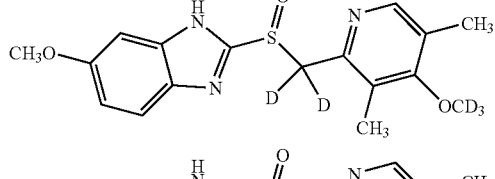
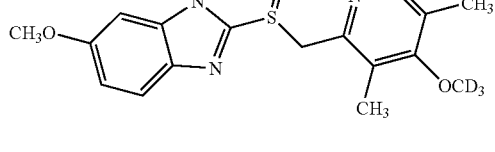

-continued
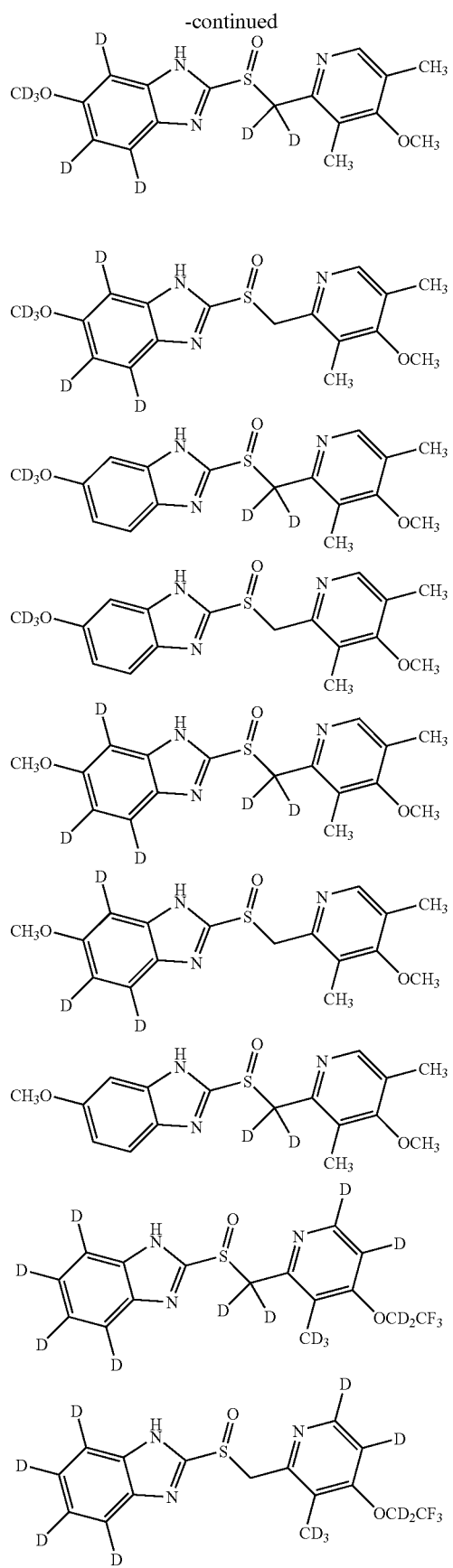
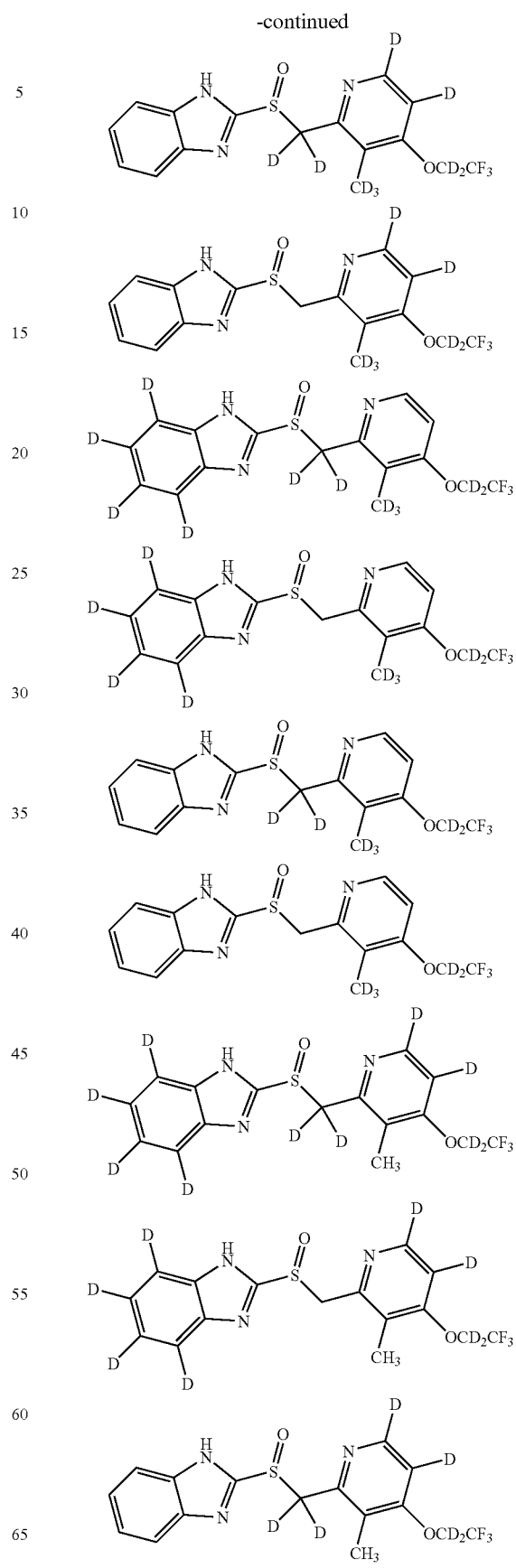

-continued
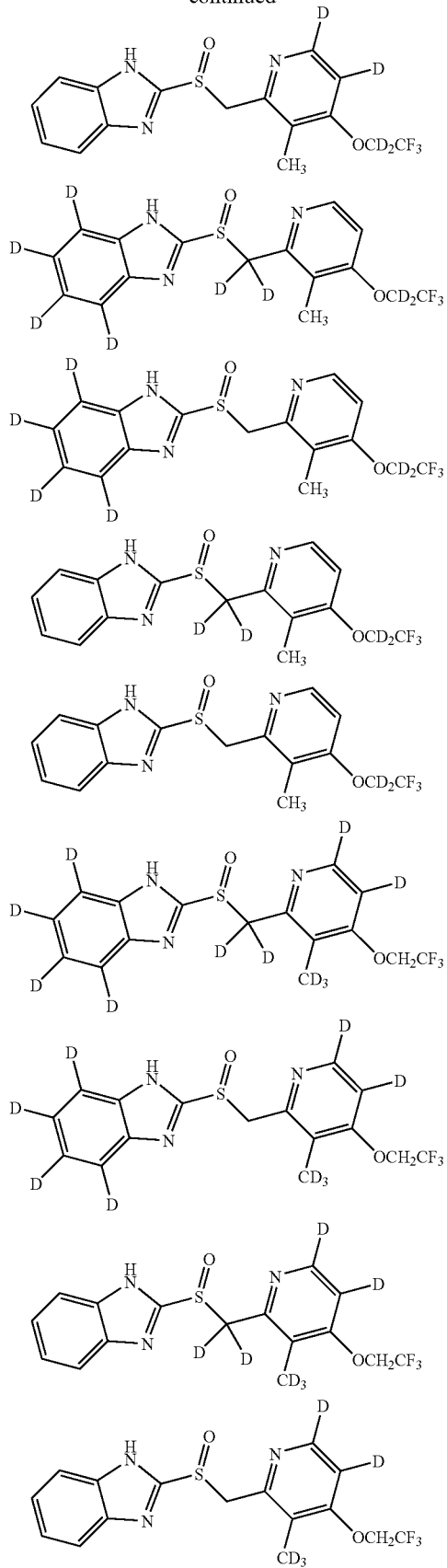
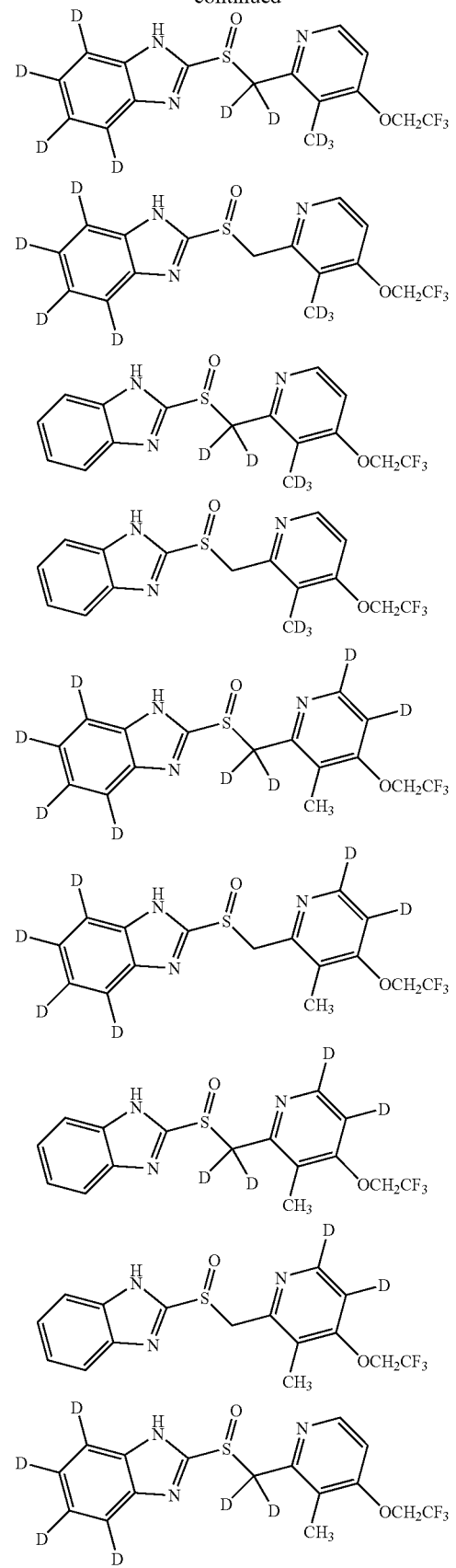

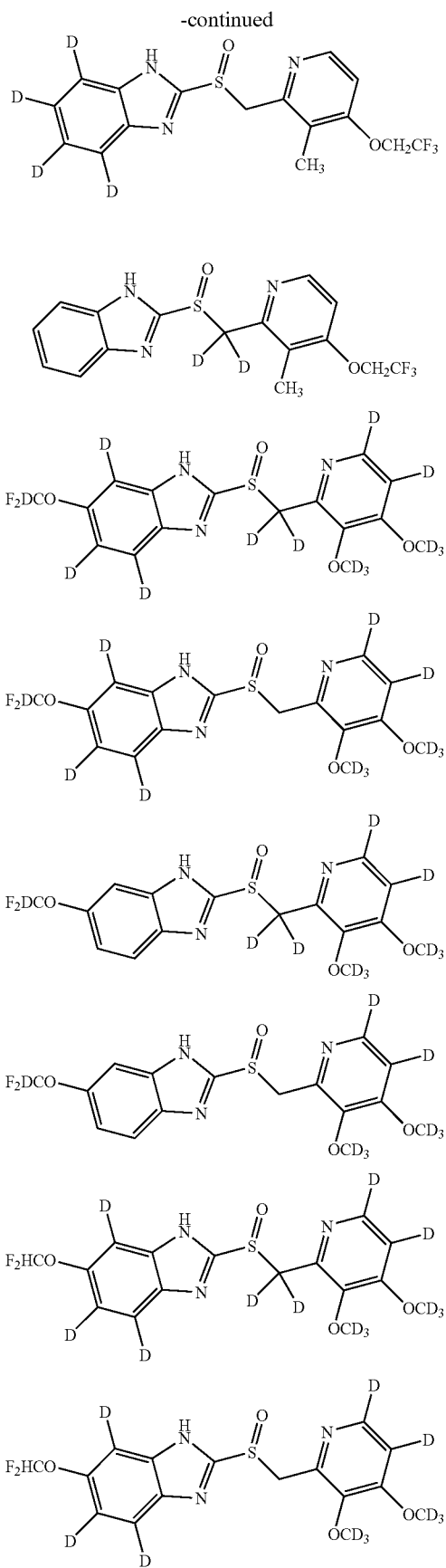
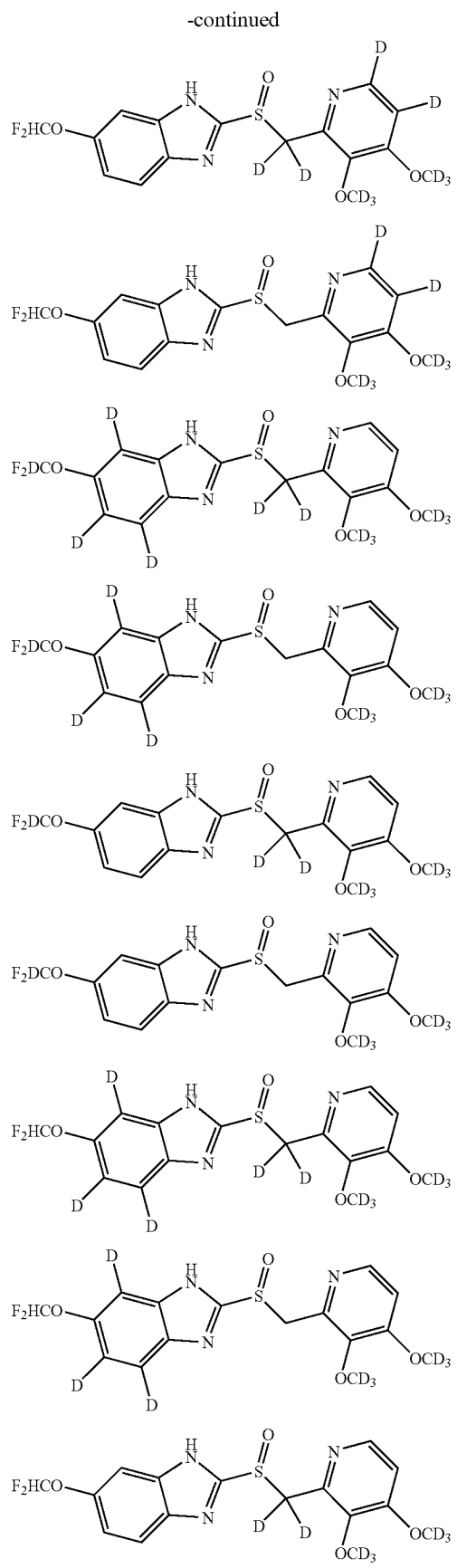

-continued
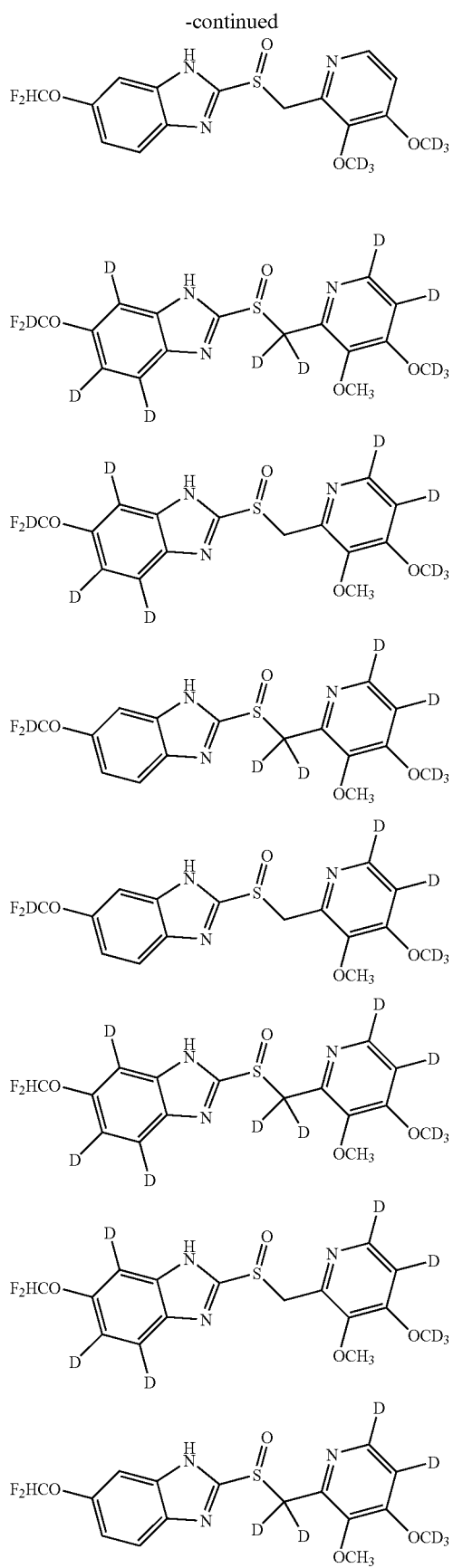
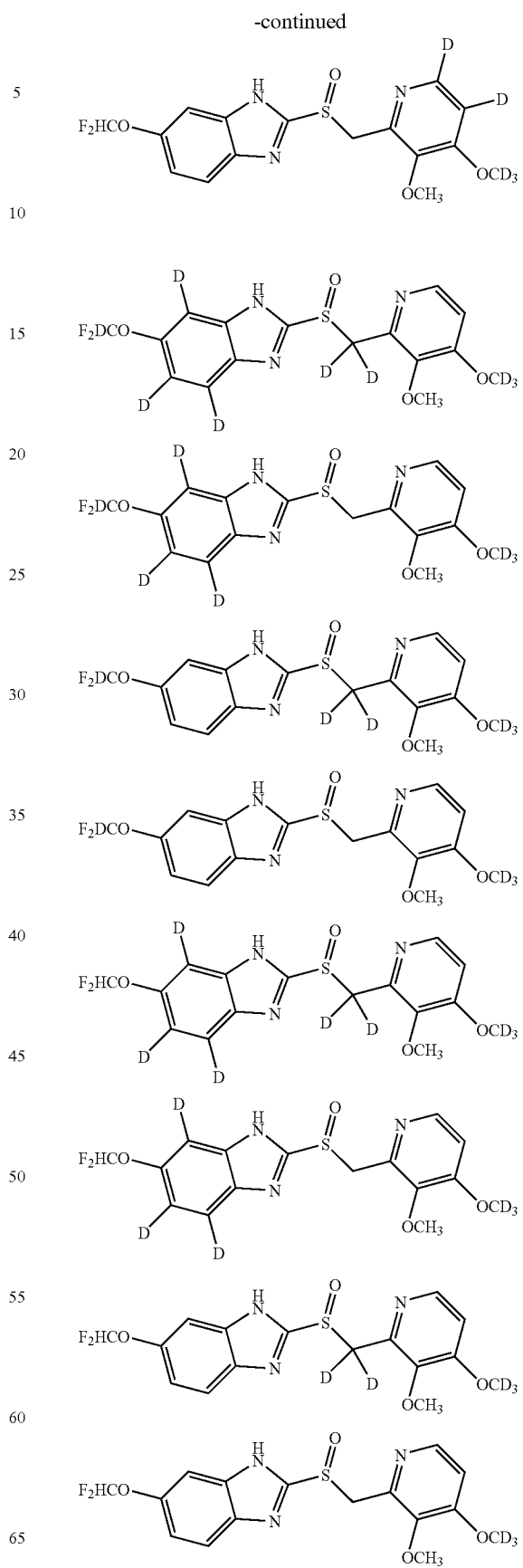

-continued
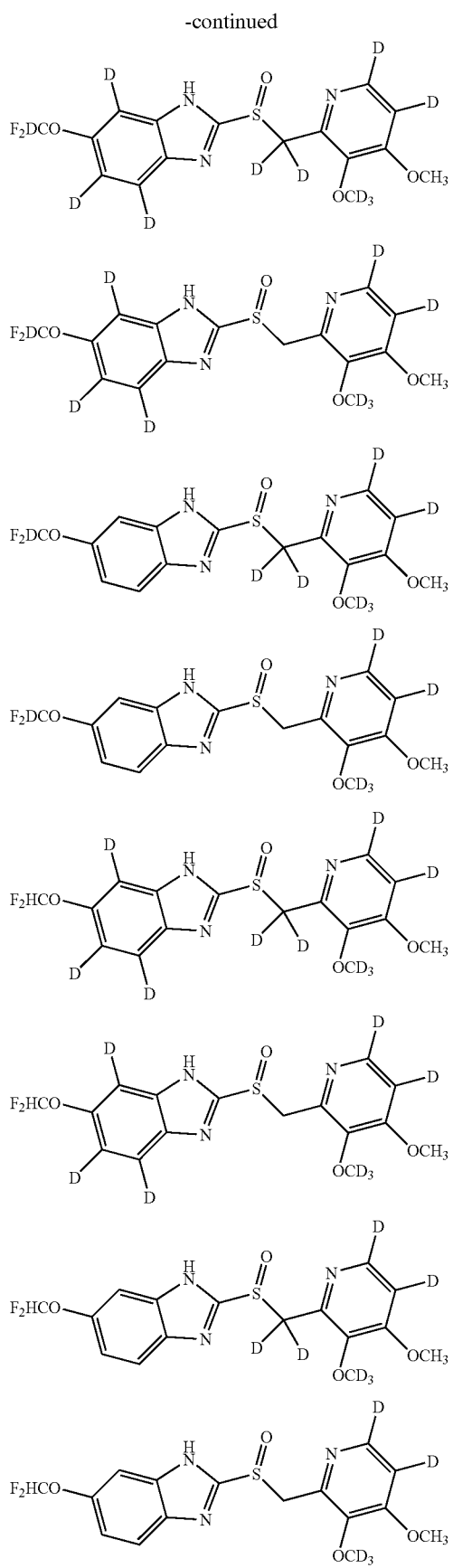
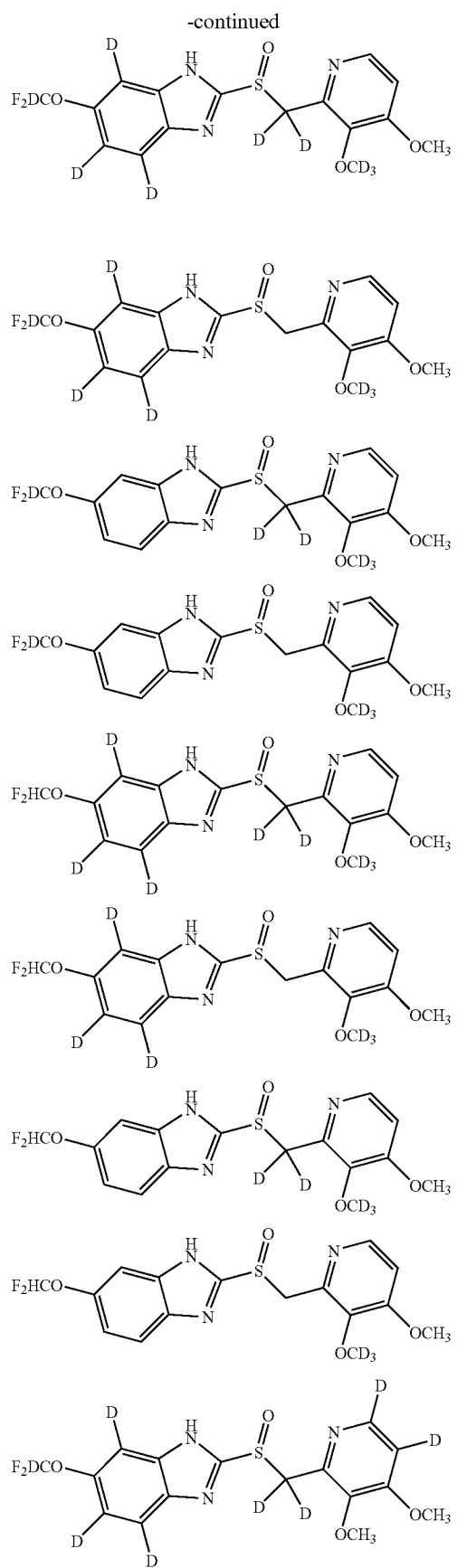

-continued
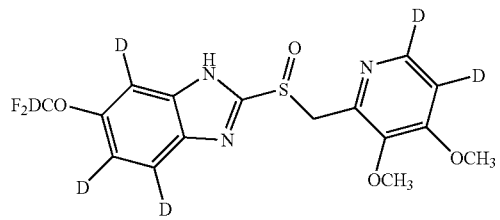
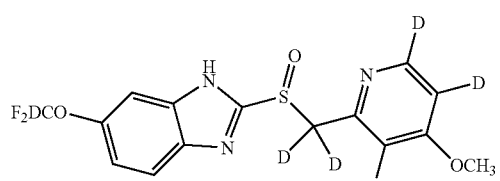
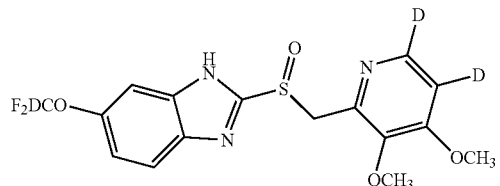
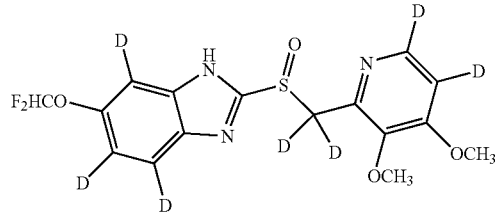
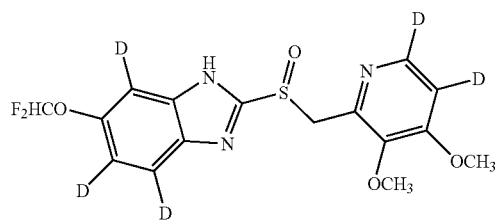
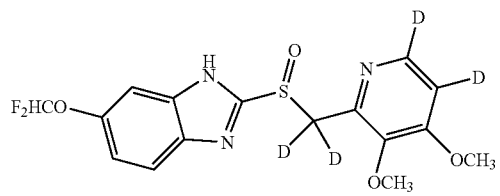
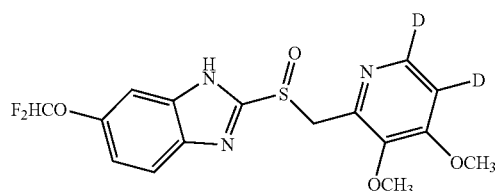
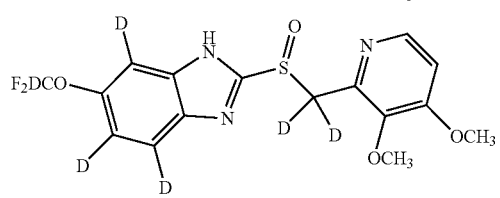
-continued
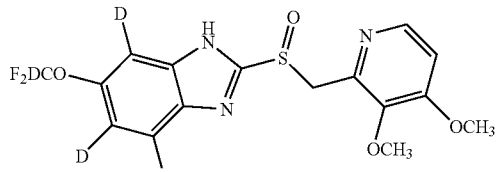
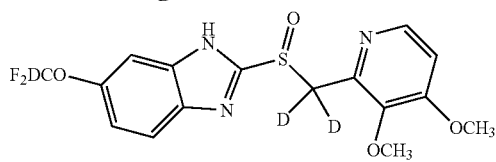
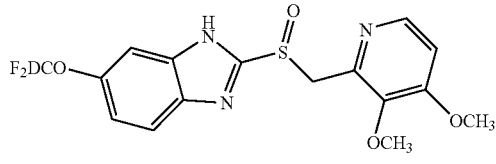
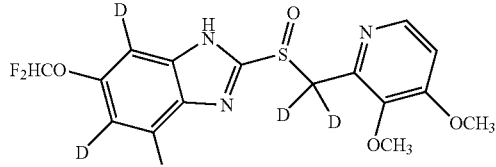
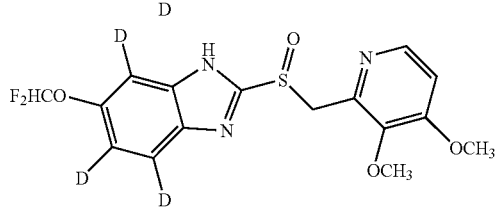
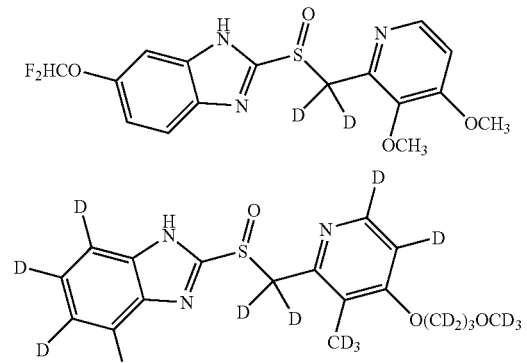
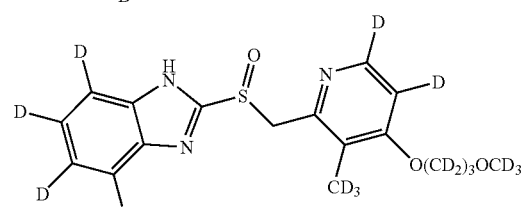
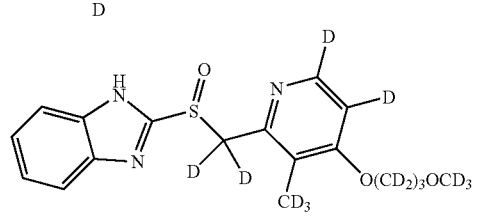

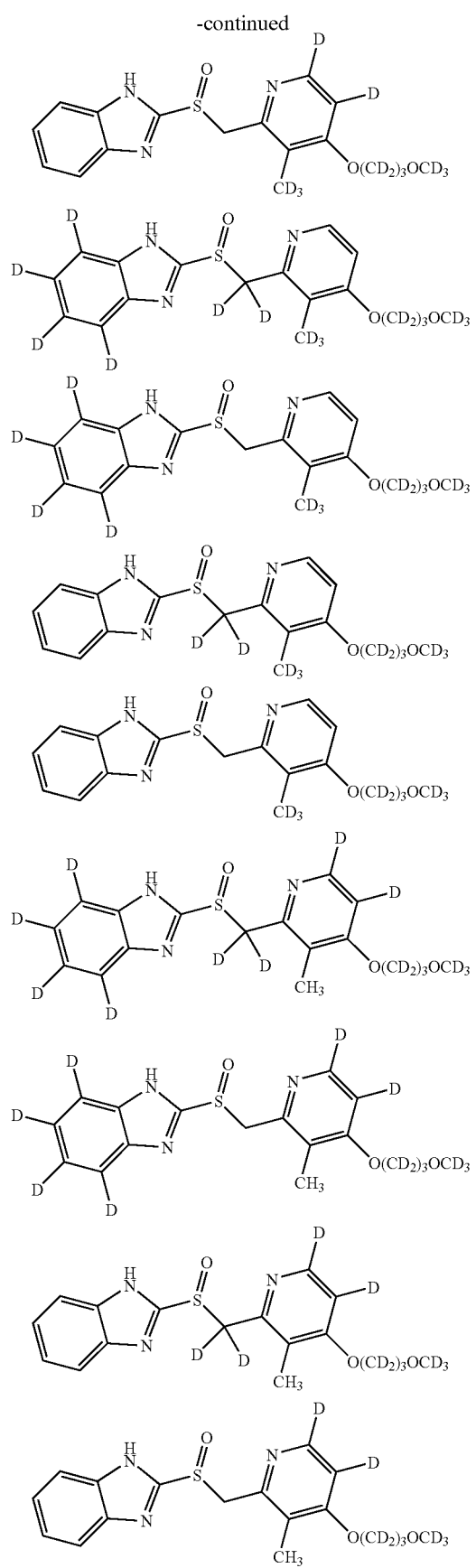
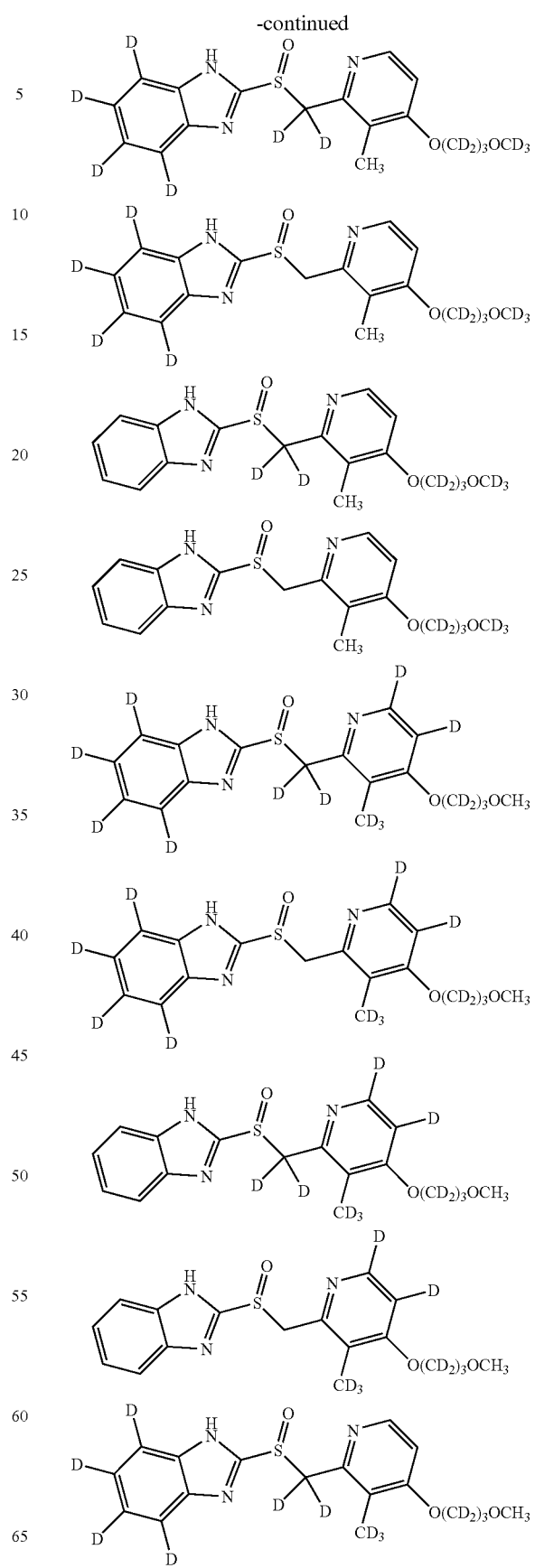

121
-continued
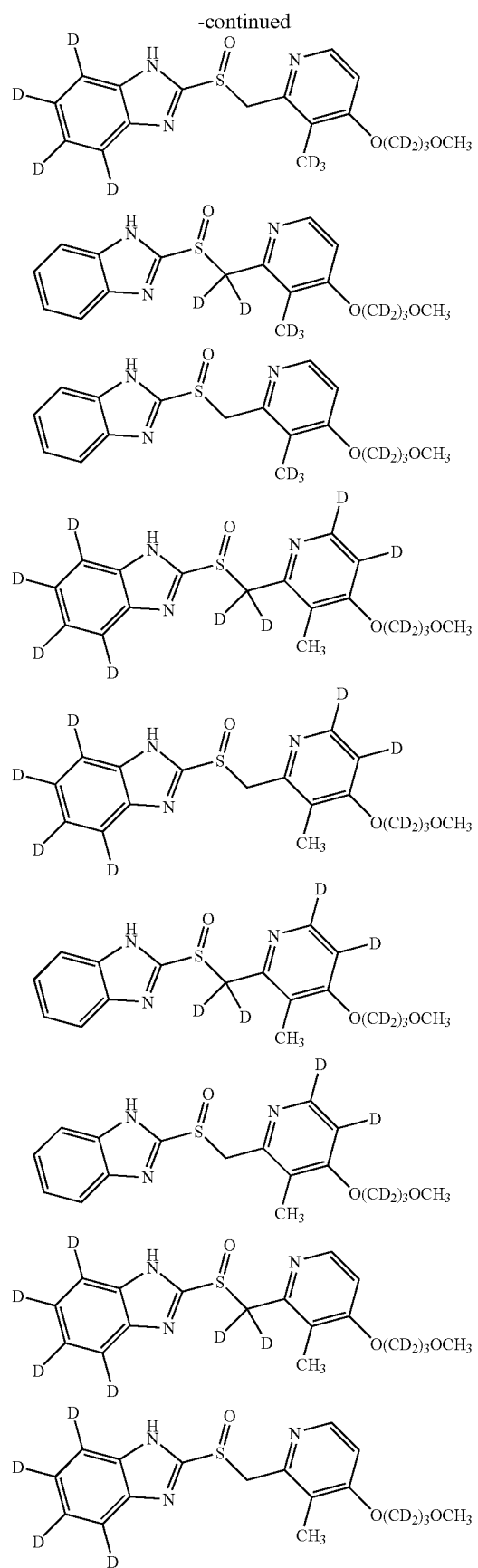
122
-continued
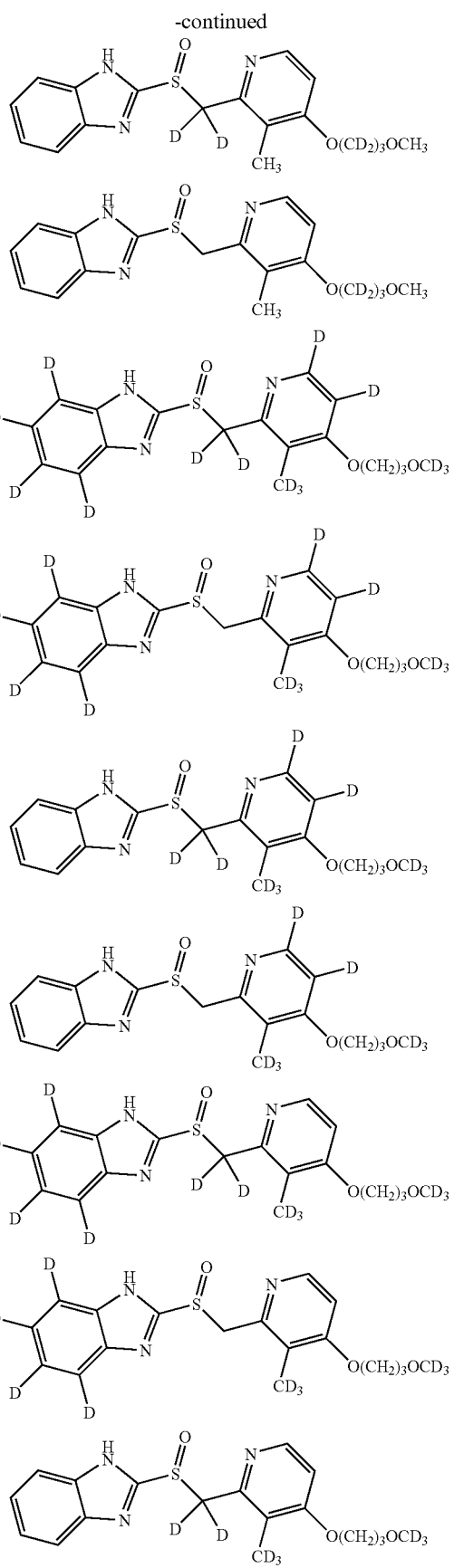

-continued
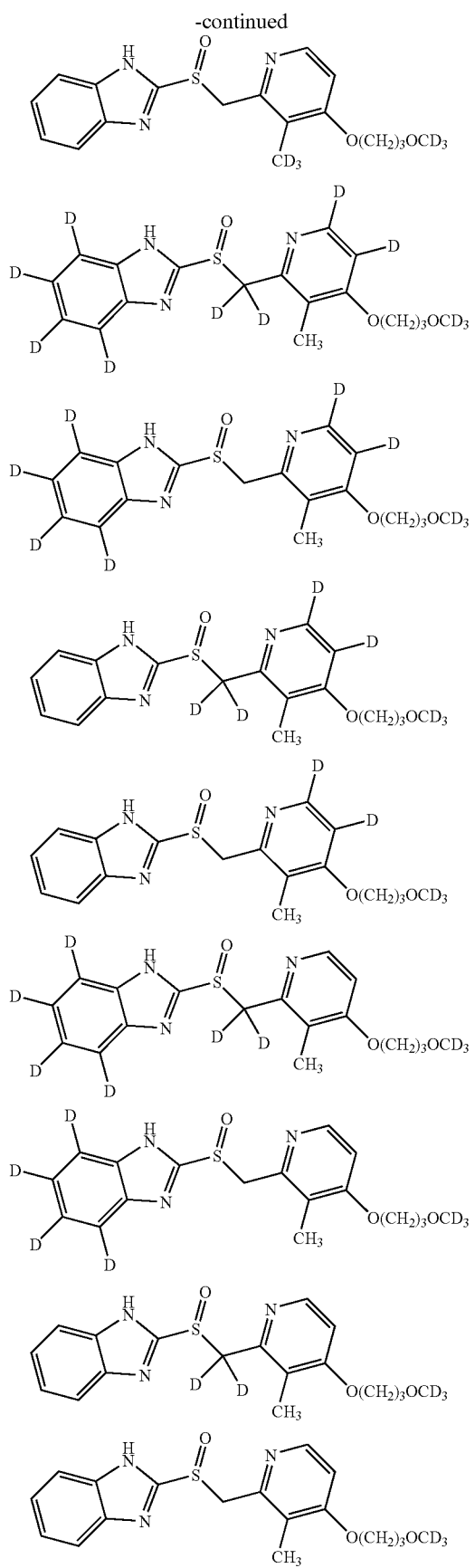
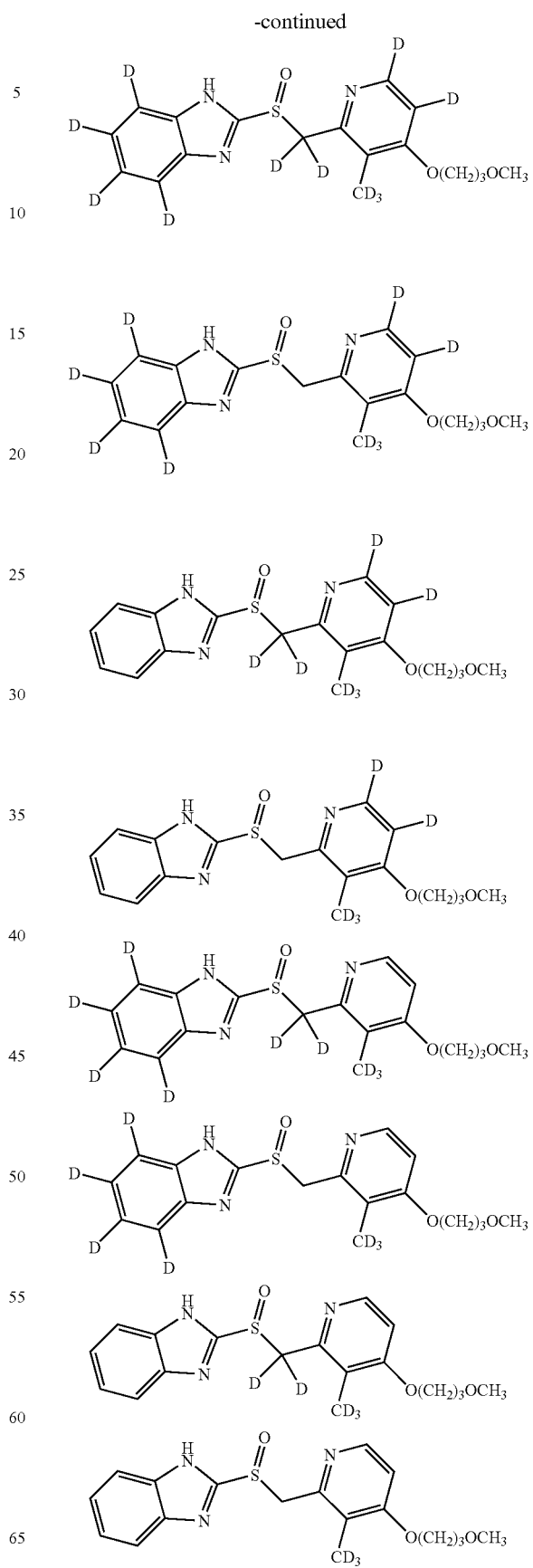

-continued

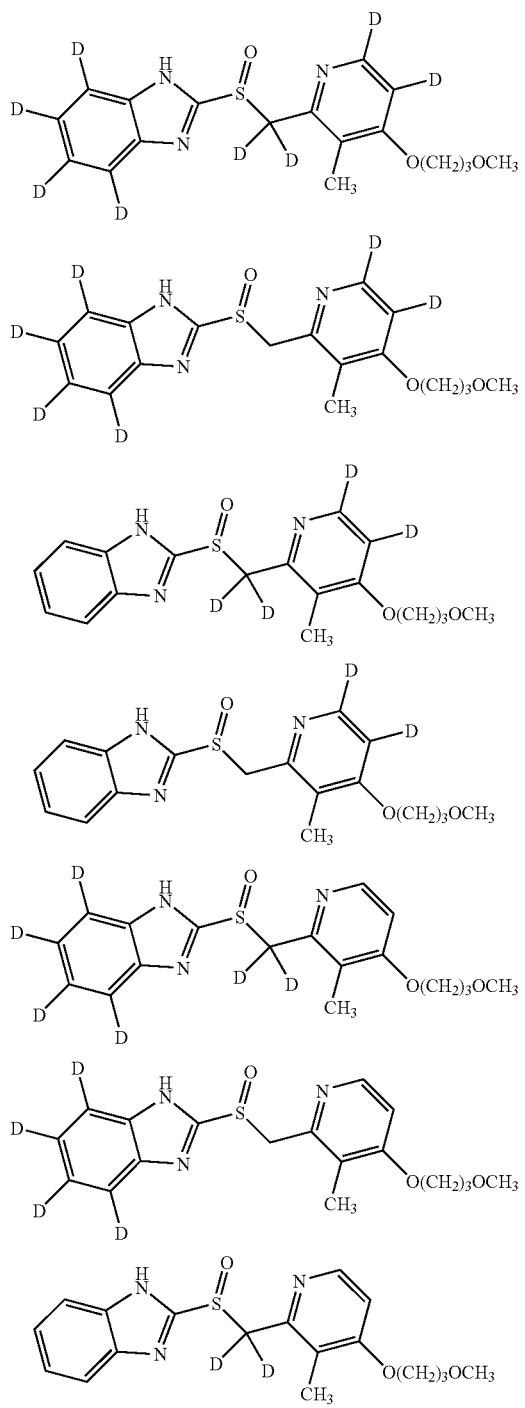

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt thereof.

7. A compound selected from the group consisting of:

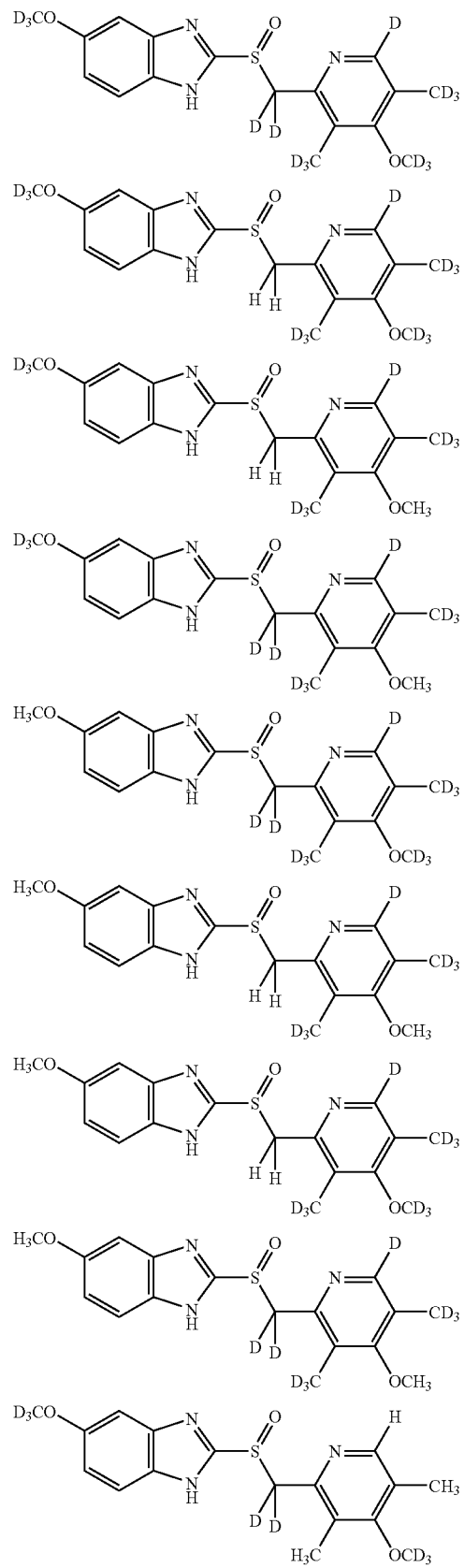

-continued

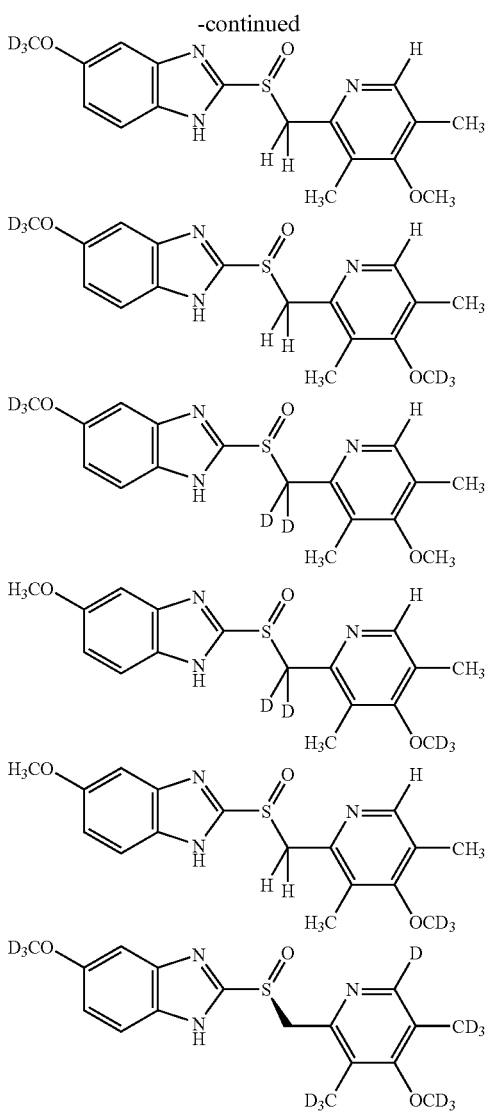

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt thereof.

8. A compound selected from the group consisting of:

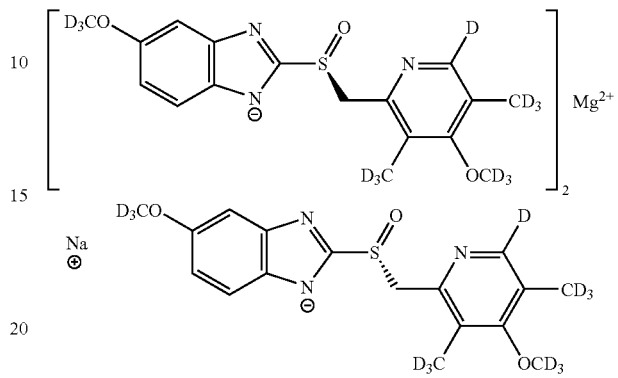

or a single enantiomer, a mixture of the (+)-enantiomer and the (−)-enantiomer, a mixture of about 90% or more by weight of the (−)-enantiomer and about boo or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt thereof.

9. A pharmaceutical composition comprising a therapeutically effective amount of a compound according to claim 1, compound together with a with a pharmaceutically acceptable carrier.

10. The pharmaceutical composition of claim 9, wherein said composition is suitable for oral, parenteral, or intravenous infusion administration.

11. The pharmaceutical composition of claim 10, wherein said oral administration comprises administering a tablet or a capsule.

12. The pharmaceutical composition of claim 9, wherein said compound of claim 1 is administered in a dose 0.5 milligram to 80 milligram total daily.

* * * * *

UNITED STATES PATENT AND TRADEMARK OFFICE
CERTIFICATE OF CORRECTION

Page 1 of 1

PATENT NO.         : 7,598,273 B2
APPLICATION NO.    : 11/544407
DATED              : October 6, 2009
INVENTOR(S)        : Thomas G. Gant and Sepehr Sarshar It is certified that error appears in the above-identified patent and that said Letters Patent is hereby corrected as shown below:

In the Claims

At column 103, line 59, delete "boo" and insert --10%-- therefor.
At column 103, line 63, delete "boo" and insert --10%-- therefor.
At column 128, line 26, delete "boo" and insert --10%-- therefor.

At column 125, line 50, insert --and-- before the last structure appearing in claim 6.
At column 125, line 55, insert a --,-- after the last structure appearing in claim 6.
At column 127, line 36, insert --and-- before the last structure appearing in claim 7.
At column 127, line 43, insert a --,-- after the last structure appearing in claim 7.
At column 128, line 15, insert --and-- after the first structure appearing in claim 8.
At column 128, line 23, insert a --,-- after the last structure appearing in claim 8.
At column 128, line 35, delete "with a" (second occurrence).

Signed and Sealed this
Eleventh Day of March, 2014

Michelle K. Lee
*Deputy Director of the United States Patent and Trademark Office*